(12) United States Patent
Ma et al.

(10) Patent No.: US 12,275,683 B2
(45) Date of Patent: *Apr. 15, 2025

(54) NITROGEN-CONTAINING COMPOUND, ELECTRONIC ELEMENT AND ELECTRONIC DEVICE

(71) Applicant: Shaanxi Lighte Optoelectronics Material Co., Ltd., Xi'an (CN)

(72) Inventors: Tiantian Ma, Xi'an (CN); Jian Li, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 742 days.

This patent is subject to a terminal disclaimer.

(21) Appl. No.: 17/619,396

(22) PCT Filed: Sep. 1, 2020

(86) PCT No.: PCT/CN2020/112826
§ 371 (c)(1),
(2) Date: Dec. 15, 2021

(87) PCT Pub. No.: WO2021/082714
PCT Pub. Date: May 6, 2021

(65) Prior Publication Data
US 2022/0306567 A1  Sep. 29, 2022

(30) Foreign Application Priority Data

Oct. 31, 2019  (CN) .......................... 201911054824.6
Apr. 10, 2020  (CN) .......................... 202010279890.X

(51) Int. Cl.
*C07C 211/54* (2006.01)
*C07D 209/82* (2006.01)
(Continued)

(52) U.S. Cl.
CPC .......... *C07C 211/54* (2013.01); *C07D 209/82* (2013.01); *C07D 213/38* (2013.01);
(Continued)

(58) Field of Classification Search
CPC . C07C 211/54; C07C 2602/42; C07C 211/60; H10K 85/631
See application file for complete search history.

(56) References Cited

U.S. PATENT DOCUMENTS

| 6,777,111 B1 | 8/2004 | Tanaka | |
|---|---|---|---|
| 2006/0127698 A1* | 6/2006 | Tokailin | C09K 11/06 428/917 |
| 2023/0111469 A1* | 4/2023 | Park | H10K 85/631 313/503 |

FOREIGN PATENT DOCUMENTS

| CN | 110156746 A | 8/2019 |
|---|---|---|
| CN | 110183332 A | 8/2019 |

(Continued)

OTHER PUBLICATIONS

Machine Translation of CN110183332B (Year: 2020).*
(Continued)

*Primary Examiner* — Jenna N Chandhok
(74) *Attorney, Agent, or Firm* — Tucker Ellis LLP

(57) ABSTRACT

The present application provides a nitrogen-containing compound as represented by formula I, an electronic element, and an electronic device, which relates to the technical field of organic materials. The nitrogen-containing compound can improve the performance of the electronic element.

(I)

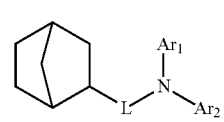

12 Claims, 2 Drawing Sheets

(51) Int. Cl.
| | |
|---|---|
| *C07D 213/38* | (2006.01) |
| *C07D 215/06* | (2006.01) |
| *C07D 307/91* | (2006.01) |
| *C07D 333/76* | (2006.01) |
| *C07D 401/12* | (2006.01) |
| *C07D 403/12* | (2006.01) |
| *C07D 405/12* | (2006.01) |
| *C07D 409/04* | (2006.01) |
| *C07D 409/12* | (2006.01) |
| *C07D 471/04* | (2006.01) |
| *C07D 519/00* | (2006.01) |
| *H10K 30/00* | (2023.01) |
| *H10K 50/15* | (2023.01) |
| *H10K 50/18* | (2023.01) |
| *H10K 85/60* | (2023.01) |

(52) U.S. Cl.
CPC ......... *C07D 215/06* (2013.01); *C07D 307/91* (2013.01); *C07D 333/76* (2013.01); *C07D 401/12* (2013.01); *C07D 403/12* (2013.01); *C07D 405/12* (2013.01); *C07D 409/04* (2013.01); *C07D 409/12* (2013.01); *C07D 471/04* (2013.01); *C07D 519/00* (2013.01); *H10K 85/631* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 30/00* (2023.02); *H10K 50/15* (2023.02); *H10K 50/18* (2023.02)

(56) References Cited

FOREIGN PATENT DOCUMENTS

| | | | | |
|---|---|---|---|---|
| CN | 110317141 A | | 10/2019 | |
| CN | 110845394 A | * | 2/2020 | |
| CN | 110183332 B | * | 4/2020 | ........... C07C 211/54 |
| CN | 111018721 A | | 4/2020 | |
| CN | 111153880 A | | 5/2020 | |
| CN | 111393308 A | | 7/2020 | |
| KR | 20180107968 A | | 10/2018 | |

OTHER PUBLICATIONS

International Search Report from corresponding International Application No. PCT/CN2020/112826, mailed on Dec. 3, 2020, 6 pages.

* cited by examiner

NITROGEN-CONTAINING COMPOUND, ELECTRONIC ELEMENT AND ELECTRONIC DEVICE

CROSS REFERENCE TO RELATED APPLICATIONS

This application claims priority to Chinese Patent Application No. CN201911054824.6, filed on Oct. 31, 2019, and Chinese Patent Application No. 202010279890.X, filed on Apr. 10, 2020, the disclosures of which are incorporated herein by reference in their entirety as part of this application.

TECHNICAL FIELD

The present application relates to the technical field of organic materials, and in particular relates to a nitrogen-containing compound, an electronic element and an electronic device.

BACKGROUND

With the development of electronic technology and advances in material science, the application scope of electronic components used to realize electroluminescence or photoelectric conversion is becoming more and more extensive. Such electronic components, such as organic electroluminescent devices or photoelectric conversion devices, generally include a cathode and an anode which are disposed oppositely, and a functional layer disposed between the cathode and the anode. The functional layer consists of multiple layers of organic or inorganic films and generally includes an energy conversion layer, a hole transport layer located between the energy conversion layer and the anode, and an electron transport layer located between the energy conversion layer and the cathode.

For example, when the electronic component is an organic electroluminescent device, the electronic component generally includes an anode, a hole transport layer, an organic light-emitting layer as an energy conversion layer, an electron transport layer, and a cathode which are stacked in sequence. When voltage is applied to the anode and the cathode, both electrodes generate an electric field, under the action of the electric field, electrons on the cathode side move towards the organic light-emitting layer and holes on the anode side also move towards the organic light-emitting layer, the electrons and the holes are combined to form excitons in the organic light-emitting layer, and the excitons are in an excited state to release energy outwards, thereby causing the organic light-emitting layer to emit light outwards.

In the prior art, some new electroluminescent materials are described in U.S. application Ser. No. 09/632,348 (now U.S. Pat. No. 6,777,111). However, there remains a need to continue to develop new materials to further improve the performance of electronic elements.

The above information of the background of the present application is merely used to enhance an understanding of the background of the present application, and thus it may include information that does not constitute the prior art known to those of ordinary skill in the art.

SUMMARY

The present application aims to provide a nitrogen-containing compound, an electronic element and an electronic device for improving the performance of electronic elements.

In order to achieve the above purpose, the present application adopts the following technical solutions:

According to a first aspect of the present application, there is provided a nitrogen-containing compound having a structural formula represented by formula I:

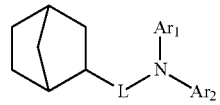

formula I wherein,

L is selected from a single bond, a substituted or unsubstituted arylene having 6-30 carbon atoms, or a substituted or unsubstituted heteroarylene having 1-30 carbon atoms;

$Ar_1$ and $Ar_2$ are the same or different and are independently selected from a substituted or unsubstituted aryl having 6-31 carbon atoms, or a substituted or unsubstituted heteroaryl having 2-30 carbon atoms;

wherein substituents of L, $Ar_1$ and $Ar_2$ are independently selected from deuterium, nitro, hydroxy, alkyl, cycloalkyl, alkenyl, alkynyl, alkoxy, alkylthio, arylsilyl, aryl optionally substituted with 0, 1, 2, 3, 4, or 5 substituent(s) selected from deuterium, fluorine, cyano and methyl, and heteroaryl optionally substituted with 0, 1, 2, 3, 4, or 5 substituent(s) selected from deuterium, fluorine, cyano or methyl.

According to a second aspect of the present application, provided is an electronic element, comprising an anode and a cathode which are oppositely disposed, and a functional layer disposed between the anode and the cathode; the functional layer contains the nitrogen-containing compounds described above.

According to a third aspect of the present application, provided is an electronic device, including the electronic element as described above.

The nitrogen-containing compound of the present application introduces norbornyl as a substituent, which can greatly reduce energy loss caused by molecular rotation, vibration, conformational change, etc. compared with substituents such as branched alkyl, so that the nitrogen-containing compound has good stability and heat resistance. Not only that, the nitrogen-containing compound introduces norbornyl between the branches of triarylamine, which can finely adjust the bonding angle and the degree of conjugation between the amine and each aryl group, thereby reducing the operating voltage of the organic electroluminescent device, improving the luminous efficiency and the lifetime, and the effects of increasing the open circuit voltage of the photoelectric conversion device, improving the photoelectric conversion efficiency, and prolonging the lifetime of the photoelectric conversion device can also be achieved, thereby improving the performance of the electronic element using the nitrogen-containing compound. The nitrogen-containing compound of the present application introduces norbornyl to adjust the performance of electronic elements, which overcomes the defects of manufacturing difficulties and high cost caused by the introduction of adamantyl, and is capable of reducing manufacturing costs of electronic elements.

BRIEF DESCRIPTION OF THE DRAWINGS

The above and other features and advantages of the present application will become more apparent by describ

Figure 1:
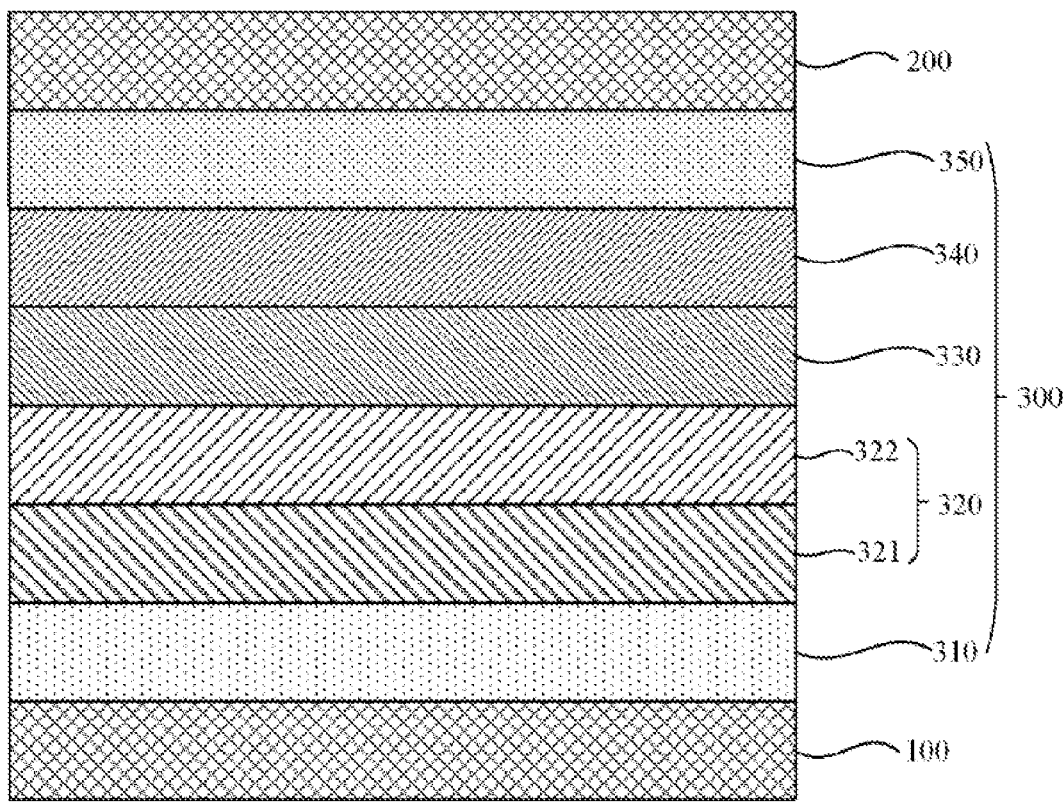
- FIG. 1 is a structural schematic diagram of an organic electroluminescent device according to the embodiments of the present application.

The main element reference signs in the drawings are illustrated below:

100, anode; 200, cathode; 300, functional layer; 310, hole injection layer; 320, hole transport layer; 321, first hole transport layer; 322, second hole transport layer; 330, organic electroluminescent layer; 340, electron transport layer; 350, electron injection layer; 360, photoelectric conversion layer; 400, first electronic device; 500, second electronic device.

DETAILED DESCRIPTION

Exemplary embodiments will now be described more fully with reference to the accompanying drawings. Exemplary embodiments can, however, be implemented in many forms and should not be construed as limited to the examples set forth herein; on the contrary, these embodiments are provided so that the present application will be thorough and complete, and will fully convey the concept of the exemplary embodiments to those skilled in the art. The described features, structures, or characteristics may be combined in any suitable manner in one or more embodiments. In the following description, numerous specific details are provided to provide a thorough understanding of embodiments of the present application.

The present application provides a nitrogen-containing compound, having a structural formula represented by formula I:

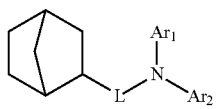

formula I

L is selected from a single bond, a substituted or unsubstituted arylene having 6-30 carbon atoms, or a substituted or unsubstituted heteroarylene having 1-30 carbon atoms;

$Ar_1$ and $Ar_2$ are the same or different and are independently selected from a substituted or unsubstituted aryl having 6-31 carbon atoms, or a substituted or unsubstituted heteroaryl having 2-30 carbon atoms;

wherein substituents of L, $Ar_1$ and $Ar_2$ are independently selected from deuterium, nitro, hydroxy, alkyl, cycloalkyl, alkenyl, alkynyl, alkoxy, alkylthio, arylsilyl, aryl optionally substituted with 0, 1, 2, 3, 4, or 5 substituent(s) selected from deuterium, fluorine, cyano and methyl, and heteroaryl optionally substituted with 0, 1, 2, 3, 4, or 5 substituent(s) selected from deuterium, fluorine, cyano or methyl.

Where, "aryl having 6-20 carbon atoms optionally substituted with 0, 1, 2, 3, 4, or 5 substituent(s) selected from deuterium, fluorine, cyano and methyl" means that aryl may be substituted with one or more of deuterium, fluorine, cyano and methyl or may not be substituted with deuterium, fluorine, cyano or methyl, and when the number of substituents on aryl is greater than or equal to 2, the substituents may be the same or different.

Optionally, the substituents of L, $Ar_1$ and $Ar_2$ are independently selected from deuterium, nitro, hydroxy, alkyl, cycloalkyl, alkenyl, alkynyl, alkoxy, alkylthio and arylsilyl.

In the present disclosure, the number of carbon atoms of L, $Ar_1$ and $Ar_2$ refers to the number of all carbon atoms. For example, if L is selected from substituted arylene having 12 carbon atoms, the number of all carbon atoms of the arylene group and its substituents is 12. For example: if $Ar_1$ is

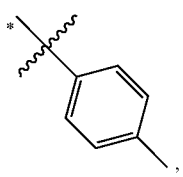

then the number of all the carbon atoms is 7; if L is

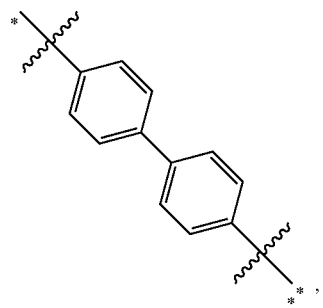 [SMILES: *c1ccc(-c2ccc(*)cc2)cc1]

the number of all the carbon atoms is 12.

In the present disclosure, aryl refers to an optional functional group or substituent derived from an aromatic hydrocarbon ring. Aryl may be monocyclic aryl or polycyclic aryl, in other words, aryl may be monocyclic aryl, or fused aryl, which is formed by two or more monocyclic aryl conjugatedly connected through by a carbon-carbon bond, formed by monocyclic aryl and fused aryl conjugatedly connected by a carbon-carbon bond, or formed by two or more fused aryl conjugatedly connected by a carbon-carbon bond. That is, two or more aromatic groups conjugatedly conjugatedly connected through a carbon-carbon bond may also be considered as aryl in the present disclosure. Where, aryl does not contain heteroatoms such as B, N, O, S, or P. For example, in the present disclosure, biphenyl, terphenyl, and the like are aryl. Examples of aryl may include phenyl, naphthyl, fluorenyl, anthracenyl, phenanthrenyl, biphenyl, terphenyl, benzo[9,10]phenanthrenyl, pyrenyl, dimethylfluorenyl, indenyl, terphenyl, benzoindenyl, dibenzoindenyl, naphthyl-substituted phenyl, phenyl-substituted naphthyl, phenanthrenyl-substituted phenyl, phenyl-substituted phenanthrenyl, phenyl-substituted 9,9-dimethylfluorenyl, phenyl-substituted 9,9-diphenylfluorenyl, or phenyl-substituted spirobifluorenyl, but are not limited thereto.

In the present disclosure, substituted aryl means that one or more hydrogen atoms in the aryl are substituted with other groups. For example, at least one hydrogen atom is substituted with a deuterium atom, hydroxy, nitro, branched alkyl, linear alkyl, cycloalkyl, alkoxy, aryl or heteroaryl, or other groups. It can be understood that substituted aryl having 18 carbon atoms means that the total number of carbon atoms of aryl and the substituents on the aryl is 18.

In the present disclosure, specific examples of aryl as a substituent include, but are not limited to, phenyl, naphthyl, phenanthrenyl, anthracenyl, dimethylfluorenyl, spirobifluorenyl, diphenylfluorenyl, biphenyl, terphenyl, benzoindenyl and dibenzoindenyl.

In the present disclosure, unsubstituted aryl refers to aryl having 6-31 carbon atoms, such as phenyl, naphthyl, fluorenyl, pyrenyl, spirobifluorenyl, anthracenyl, phenanthrenyl, chrysenyl, biphenyl, benzoanthryl, perylenyl, indenyl, terphenyl, benzoindenyl, dibenzoindenyl, and the like. The substituted aryl having 6-30 carbon atoms means that at least one hydrogen atom is substituted with a deuterium atom, F, Cl, I, CN, hydroxy, nitro, aryl, heteroaryl, or the like. Substituted aryl such as methyl-substituted phenyl, deuterium-substituted phenyl, methyl-substituted naphthyl, naphthyl-substituted phenyl, phenyl-substituted naphthyl, phenanthrenyl-substituted phenyl, phenyl-substituted phenanthrenyl, phenyl-substituted 9,9-dimethylfluorenyl, phenyl-substituted 9,9-diphenylfluorenyl, phenyl-substituted spirobifluorenyl.

In the present disclosure, unsubstituted aralkyl refers to aralkyl having 7-31 carbon atoms; for example: benzyl and the like. Substituted aralkyl having 7-31 carbon atoms means that at least one hydrogen atom is substituted with a deuterium atom, F, Cl, I, CN, hydroxy, nitro, or the like.

In the present disclosure, "heteroaryl" refers to a group in which at least one carbon atom on aryl is substituted with heteroatoms N, O, P, S, and Si. That is, heteroaryl may be monocyclic heteroaryl or polycyclic heteroaryl, in other words, heteroaryl may be a single aromatic ring system or multiple aromatic ring systems conjugated by carbon-carbon bonds, and either aromatic ring system is an aromatic monocyclic ring or an aromatic fused ring.

In the present disclosure, unsubstituted heteroaryl may refer to heteroaryl having 2-30 carbon atoms. For example, pyridyl, pyrazinyl, pyrimidinyl, pyridazinyl, triazinyl, quinolinyl, indolyl, carbazolyl, dibenzofuranyl, dibenzothienyl, dibenzoselenophenyl, phenanthrolinyl, quinazolinyl, and the like. Substituted heteroaryl having 2-30 carbon atoms means that at least one hydrogen atom is substituted with a deuterium atom, F, Cl, I, CN, hydroxyl, nitro, methyl, aryl, heteroaryl, or the like. For example: N-phenylcarbazolyl, phenyl-substituted dibenzofuranyl, phenyl-substituted dibenzothienyl, phenyl-substituted N-phenylcarbazolyl, methyl-substituted pyridyl, phenyl-substituted pyridyl, phenanthrolinyl-substituted phenyl, pyridyl-substituted phenyl, phenyl-substituted pyridyl, and the like.

In the present disclosure, specific examples of heteroaryl as a substituent include, but are not limited to, carbazolyl, N-phenylcarbazolyl, dibenzofuranyl, dibenzothienyl, pyridyl, quinolinyl, quinazolinyl, and phenanthrolinyl.

In the present disclosure, halogen refers to fluorine, chlorine, bromine, and iodine.

In the present disclosure, the interpretation for aryl may be applied to arylene, and the interpretation for heteroaryl may also be applied to heteroarylene.

The nitrogen-containing compound of the present application has good hole transport efficiency, and thus may be applied as a material for transporting holes in an electronic element for realizing photoelectric conversion or electro-optical conversion, for example, in an organic electroluminescent device or a photoelectric conversion device. For example, the nitrogen-containing compound of the present application may be applied between an anode of an organic electroluminescent device and an organic electroluminescent layer as an energy conversion layer in order to transport holes in the anode to the organic electroluminescent layer. Optionally, the nitrogen-containing compound of the present application may be applied to any one or more of a hole injection layer, a hole transport layer and an electron blocking layer of an organic electroluminescent device.

As another example, the nitrogen-containing compound of the present application may be applied between an anode of a photoelectric conversion device and a photoelectric conversion layer as an energy conversion layer in order to transport holes in the photoelectric conversion layer to the anode.

In the present disclosure, preferably, the substituents of $Ar_1$, $Ar_2$, and L are the same or different and are independently selected from deuterium, alkyl having 1-3 carbon atoms, aryl having 6-25 carbon atoms, or heteroaryl having 3-20 carbon atoms.

In one embodiment of the present disclosure, L is selected from a substituted or unsubstituted arylene having 6-25 carbon atoms.

In the present disclosure, substituent of L is selected from the group consisting of deuterium, alkyl having 1-10 carbon atoms, cycloalkyl having 3-15 carbon atoms, or aryl having 6-12 carbon atoms. Specifically, substituent of L includes, but is not limited to, deuterium, methyl, ethyl, n-propyl, isopropyl, phenyl, or naphthyl.

In one embodiment of the present disclosure, the L is a substituted or unsubstituted V, and the unsubstituted V is selected from the group consisting of the following groups:

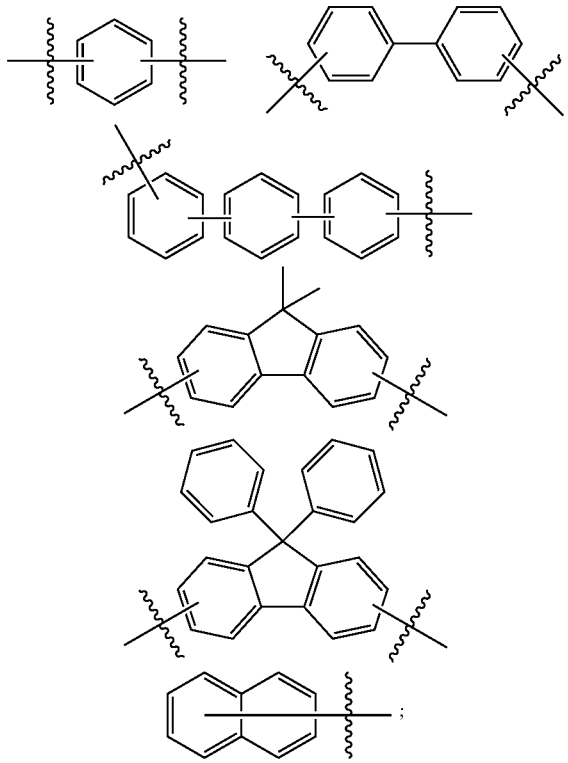

the substituted V has one or more substituent(s) thereof, and the substituent(s) are each independently selected from deuterium, fluorine, cyano, methyl, tert-butyl, phenyl, naphthyl, phenanthrenyl and anthracenyl; and when the number of substituents on the V is greater than 1, the substituents are identical or different.
In one embodiment of the present disclosure, the L is selected from the group consisting of the following groups:
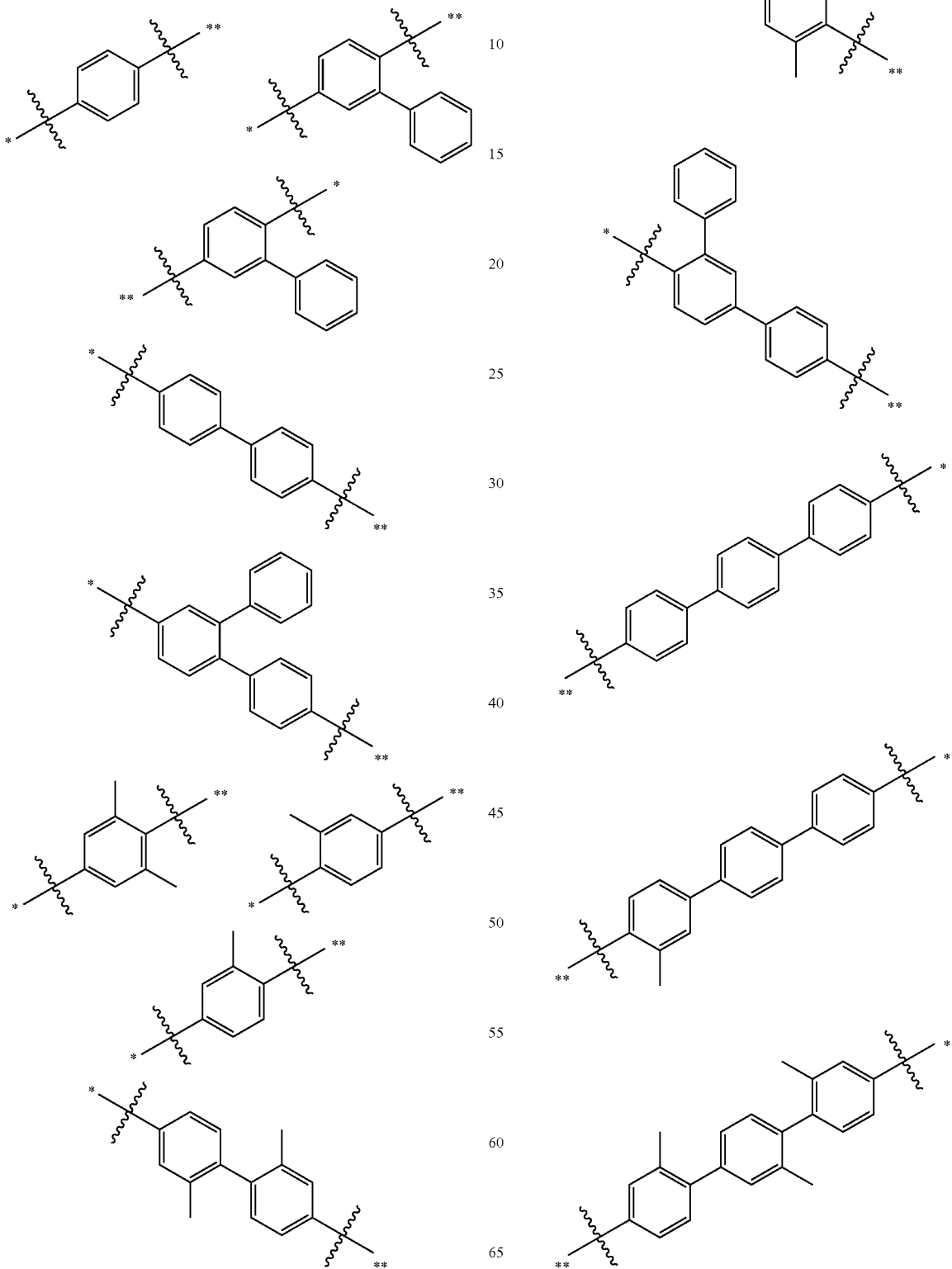

-continued

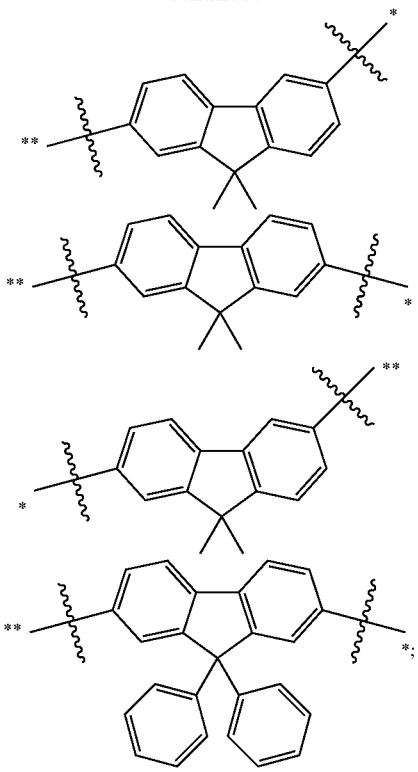

where, * is a linking point of L connected to

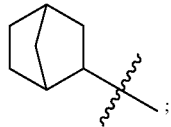 [SMILES: *C1CC2CCC1C2]

and ** is a linking point of L connected to

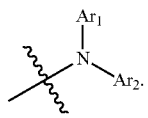

In one embodiment of the present disclosure, L is a single bond.

In one embodiment of the present disclosure, $Ar_1$ and $Ar_2$ are independently selected from a substituted or unsubstituted aryl having 6-31 carbon atoms or a substituted or unsubstituted heteroaryl having 2-30 carbon atoms.

Preferably, the $Ar_1$ and $Ar_2$ are independently selected from unsubstituted aryl having 6-31 carbon atoms, substituted aryl having 7-31 carbon atoms, unsubstituted heteroaryl having 4-18 carbon atoms, or substituted heteroaryl having 6-15 carbon atoms.

In the present disclosure, substituents of $Ar_1$ and $Ar_2$ are selected from the group consisting of deuterium, alkyl having 1-3 carbon atoms, cycloalkyl having 3-15 carbon atoms, aryl having 6-25 carbon atoms, and heteroaryl having 3-15 carbon atoms. Specifically, the substituents of $Ar_1$ and $Ar_2$ include, but are not limited to, deuterium, methyl, ethyl, n-propyl, isopropyl, phenyl, naphthyl, pyridyl, dibenzothienyl, dibenzofuranyl, quinolinyl, carbazolyl, or phenanthrolinyl.

In one embodiment of the present disclosure, the $Ar_1$ and $Ar_2$ are independently selected from a substituted or unsubstituted W, and the unsubstituted W is selected from the group consisting of the following groups:

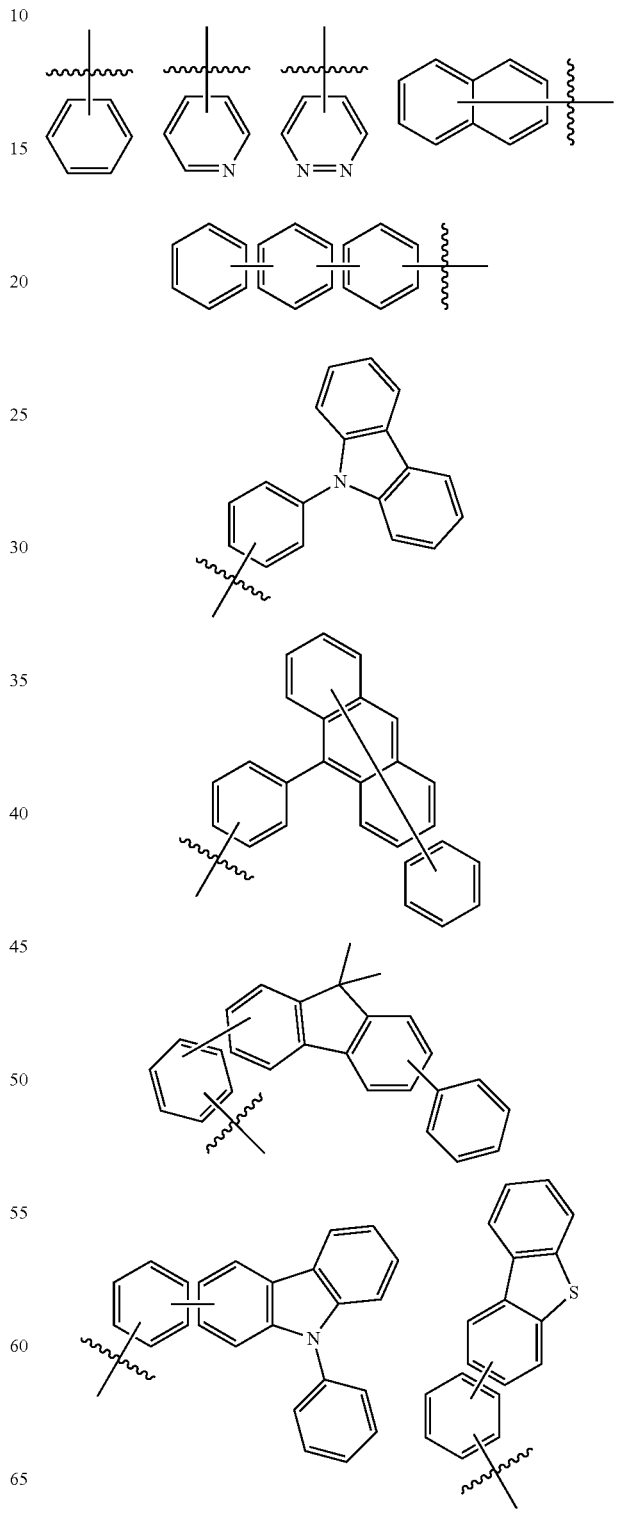

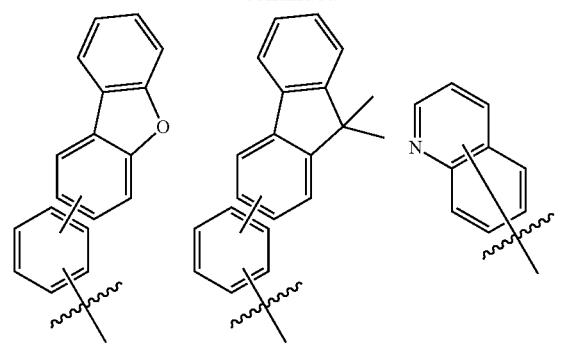
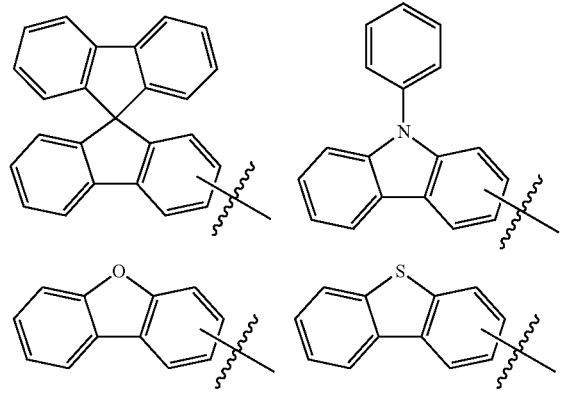
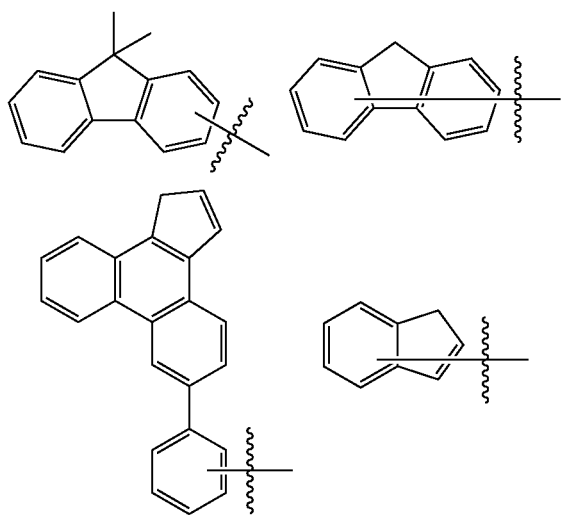
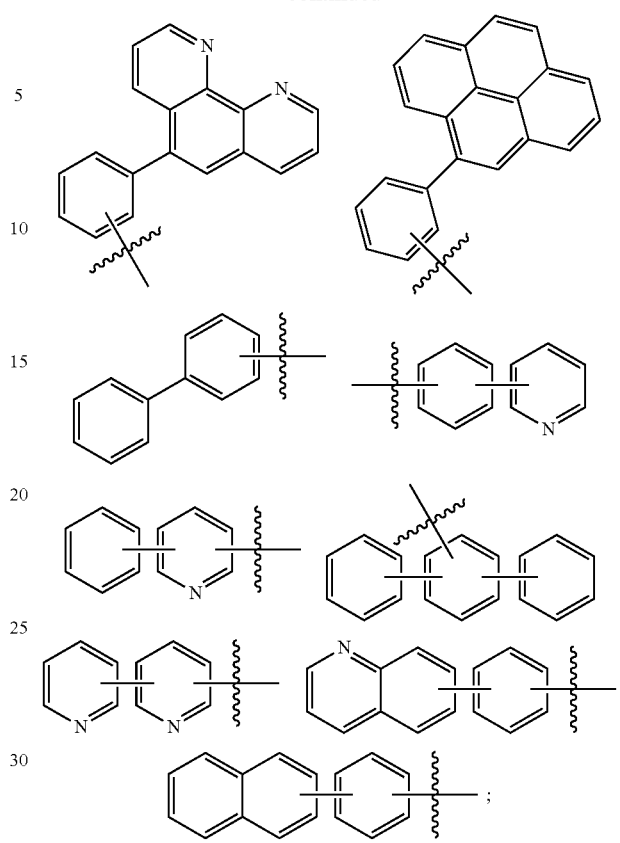
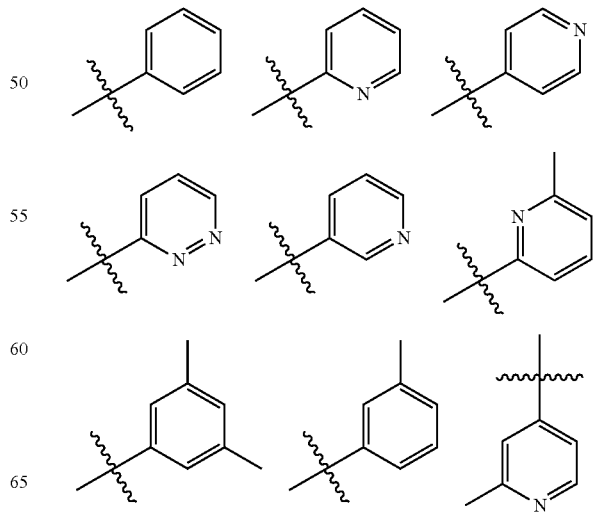

the substituted W has one or more substituents thereof, and the substituent(s) are each independently selected from deuterium, fluorine, cyano, methyl, phenyl, naphthyl, phenanthrenyl, t-butyl, pyridyl, phenanthrolinyl, pyridazinyl, dimethylfluorenyl, or spirobifluorenyl; when the number of substituents of W is greater than 1, the substituents are the same or different.

Specially, the $Ar_1$ and $Ar_2$ are independently selected from the group consisting of the following groups:

-continued
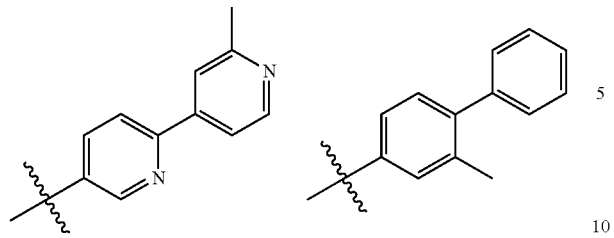
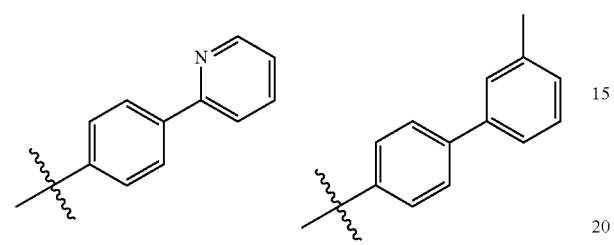
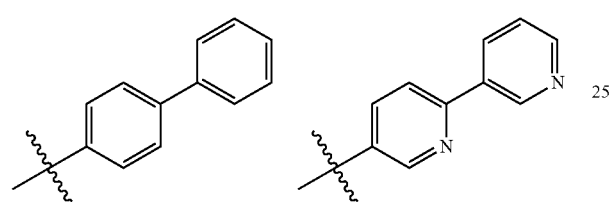
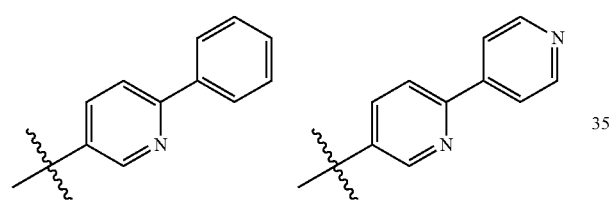
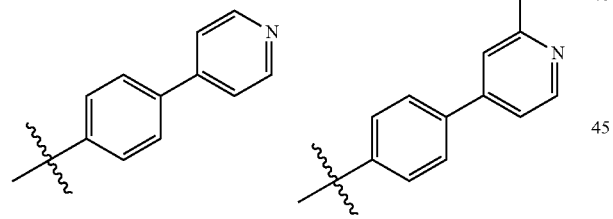
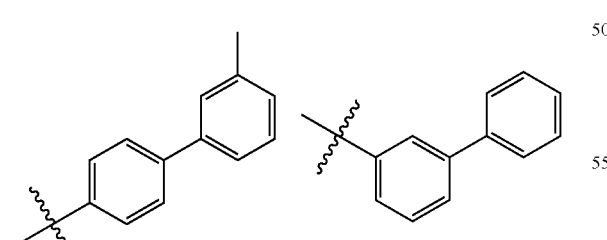
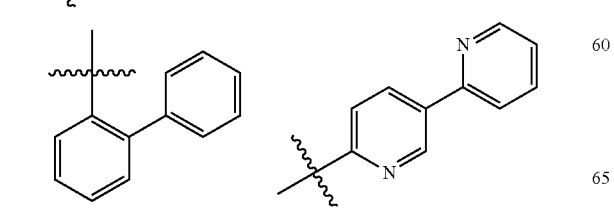
-continued
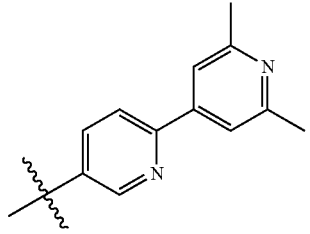
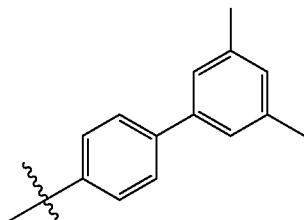
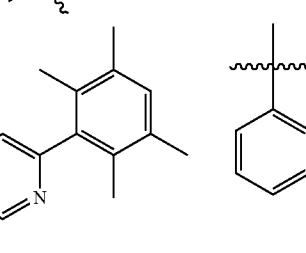
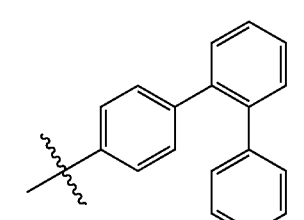
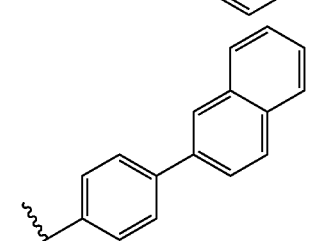
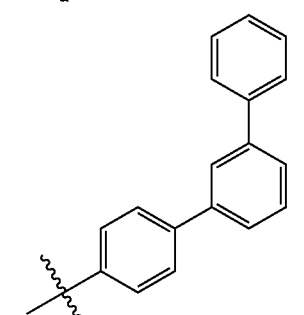
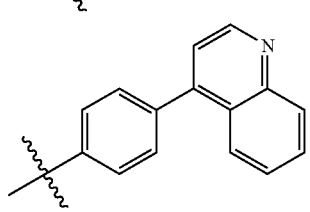

-continued
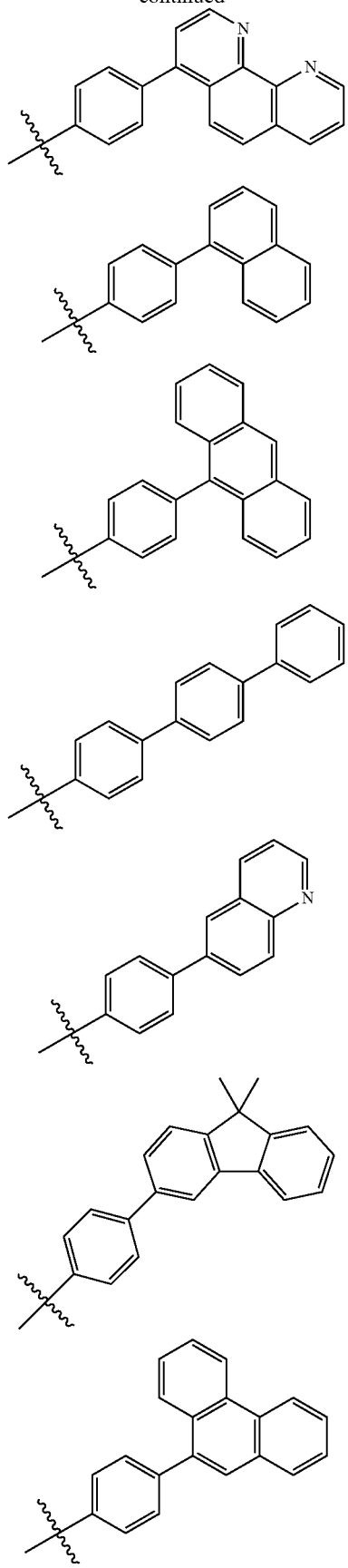
-continued
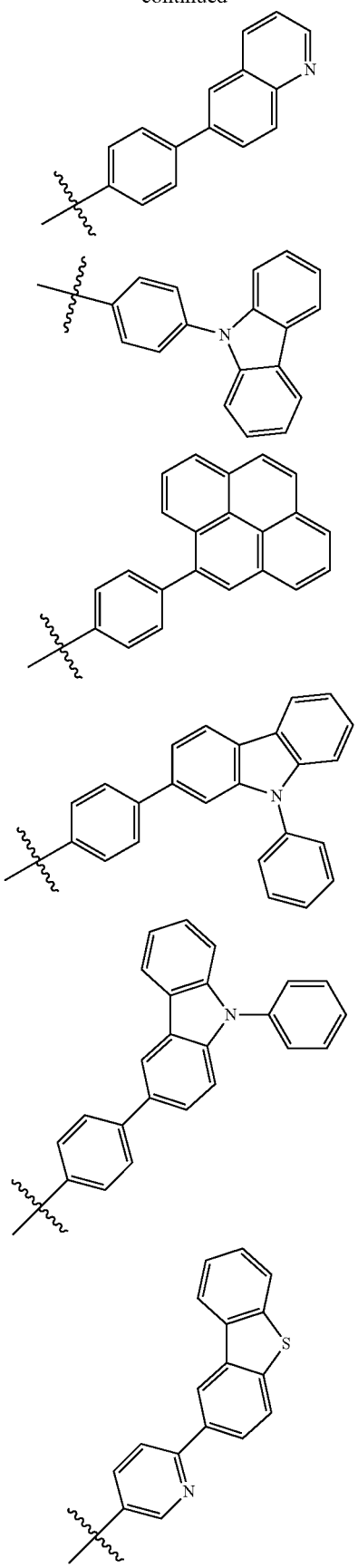

-continued
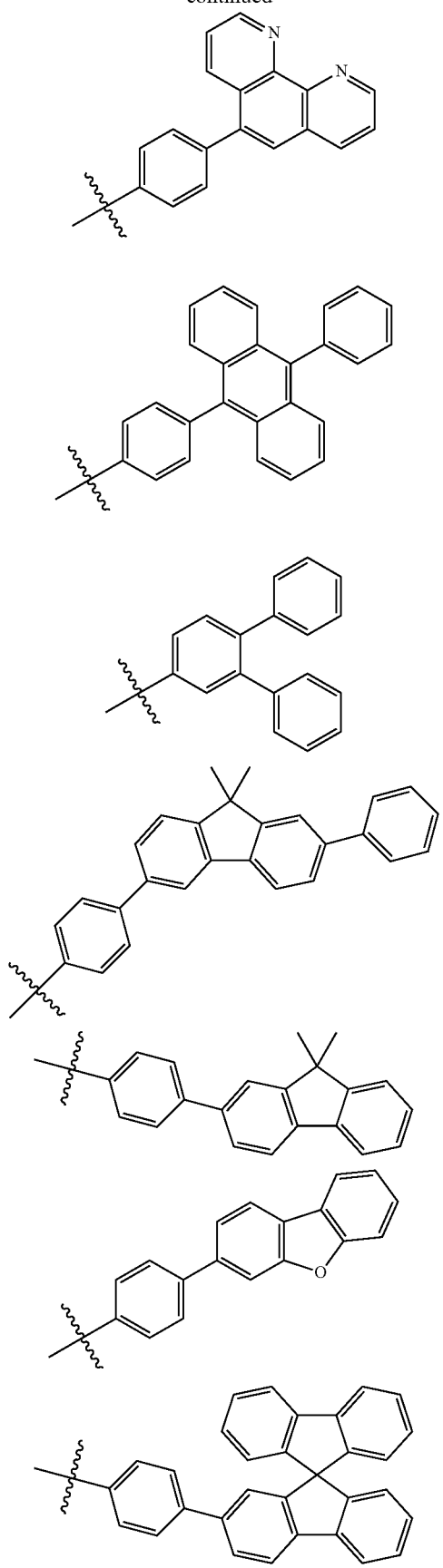
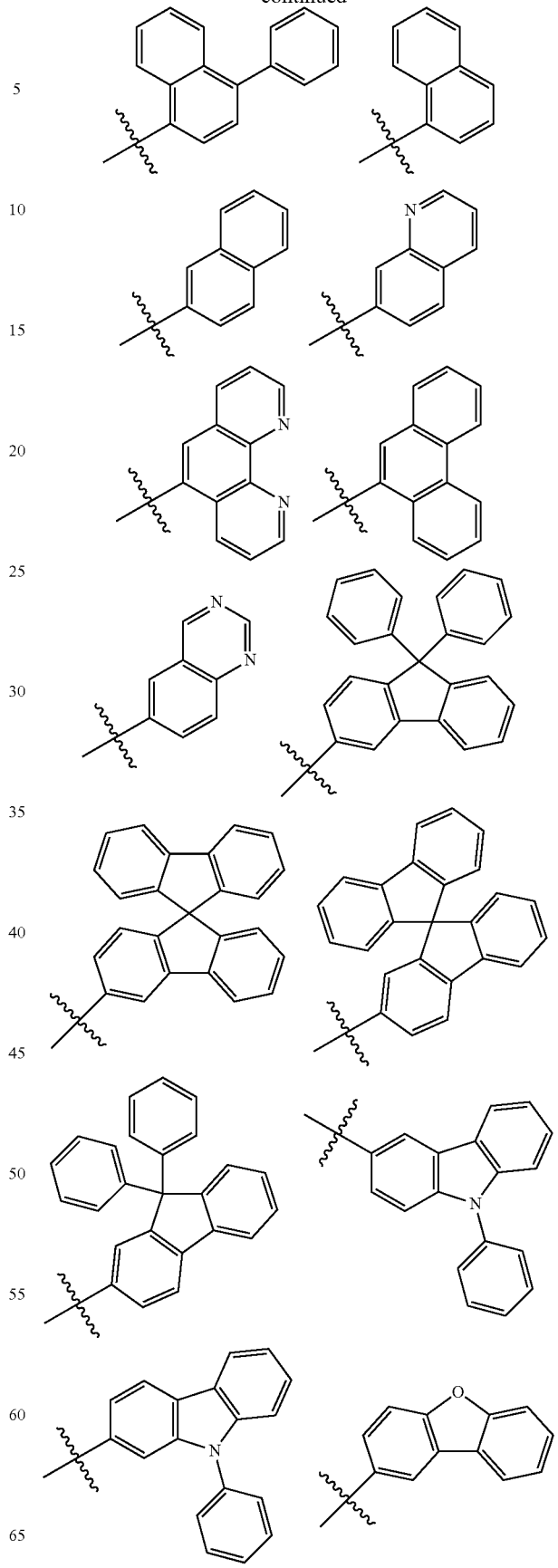

-continued
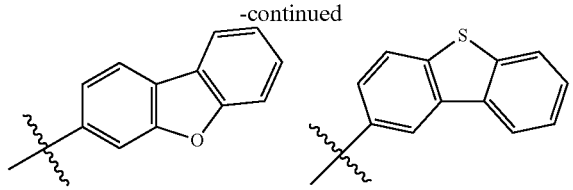
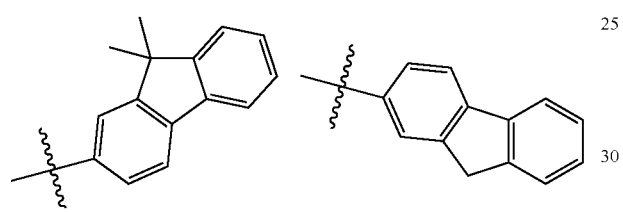
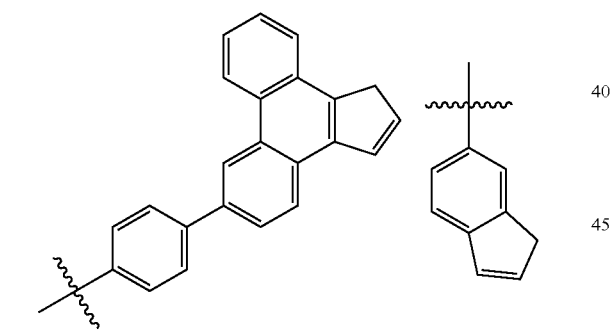
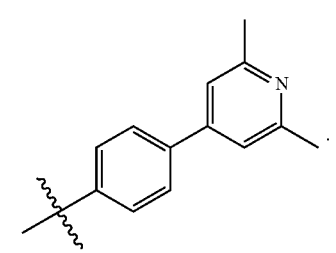
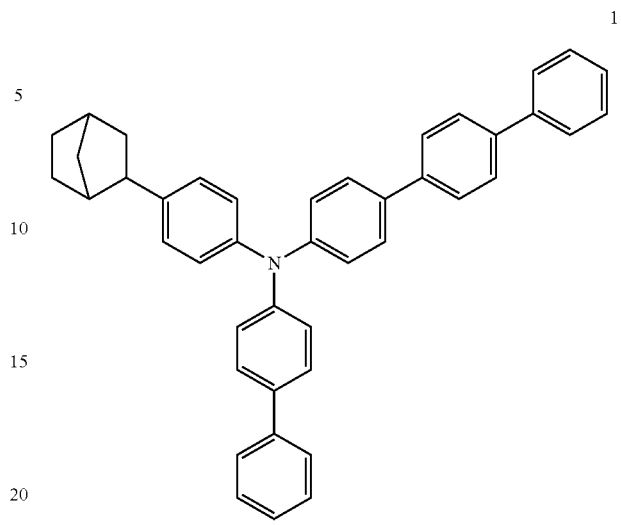
1
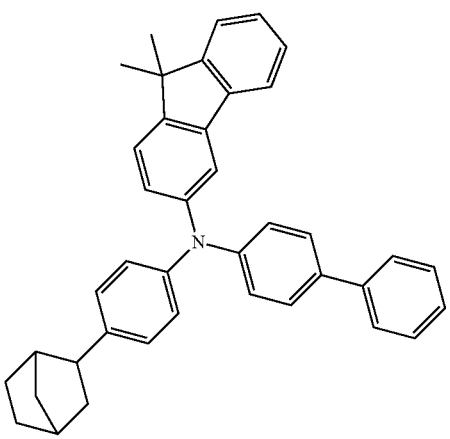
2
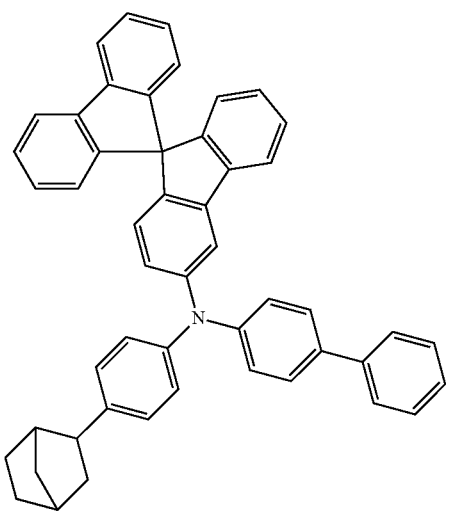
3
In the present disclosure, the nitrogen-containing compound may be selected from the group consisting of the following compounds:

4
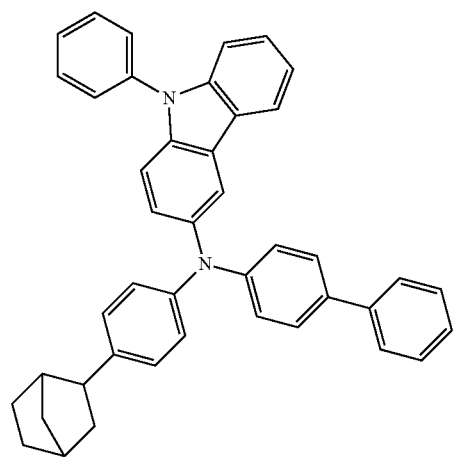
5
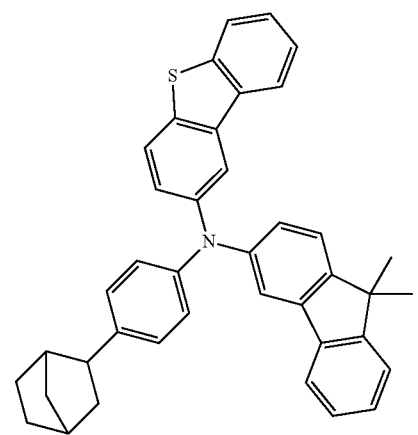
6
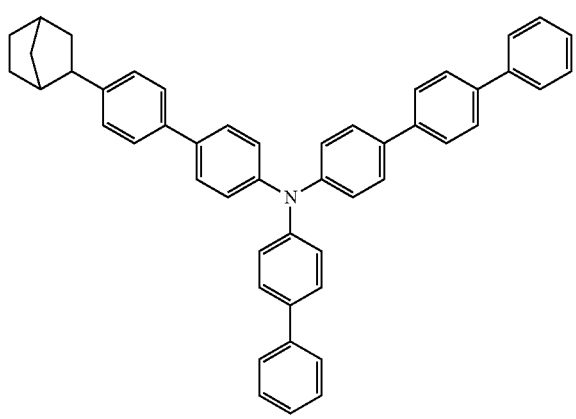
7
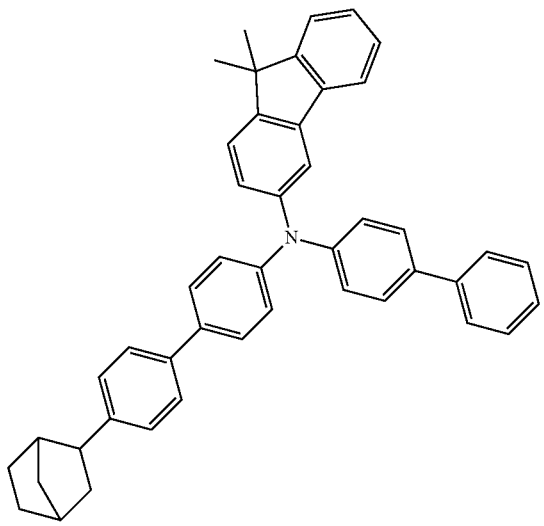
8
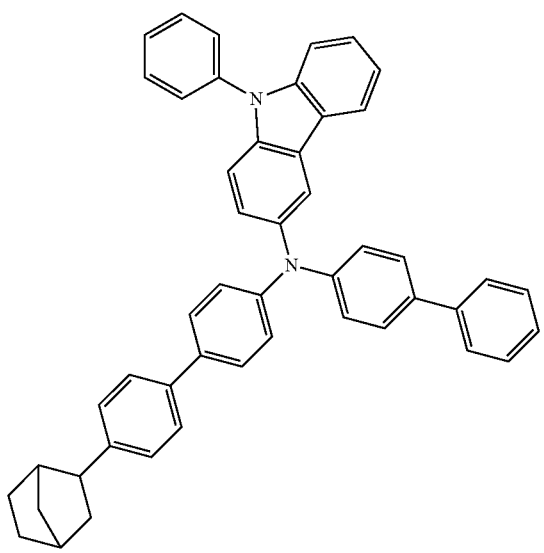
9
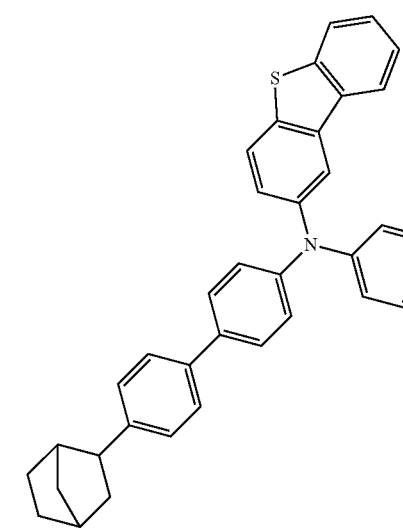

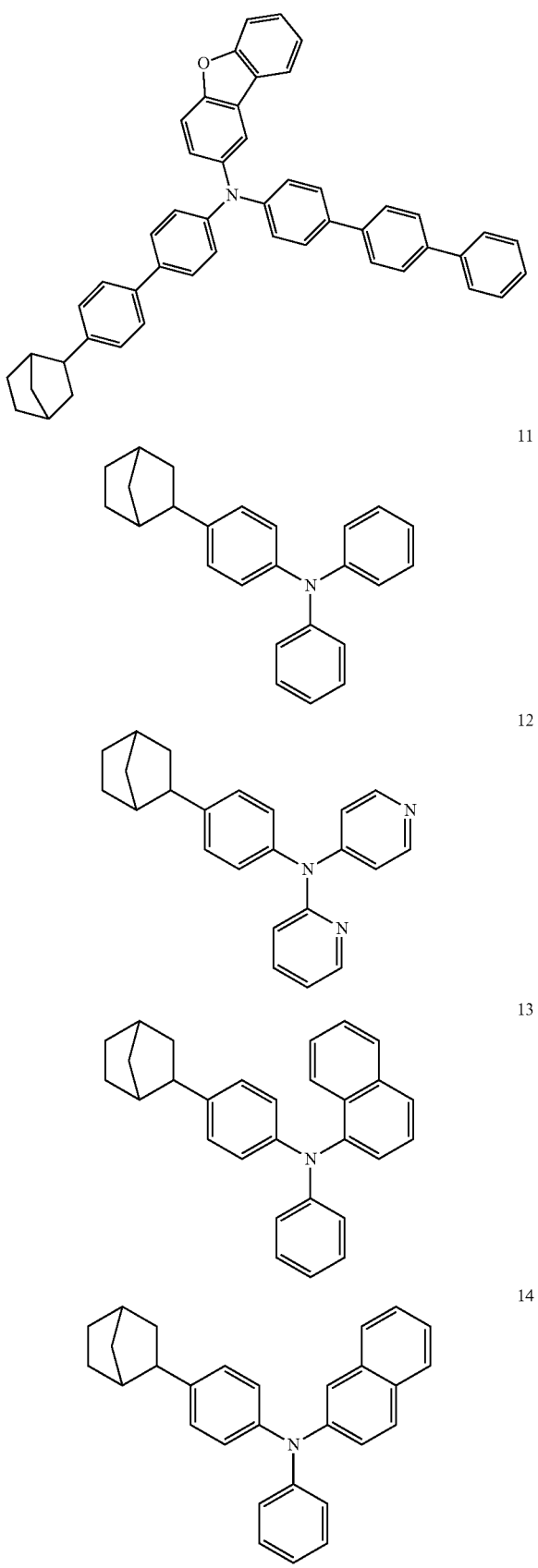
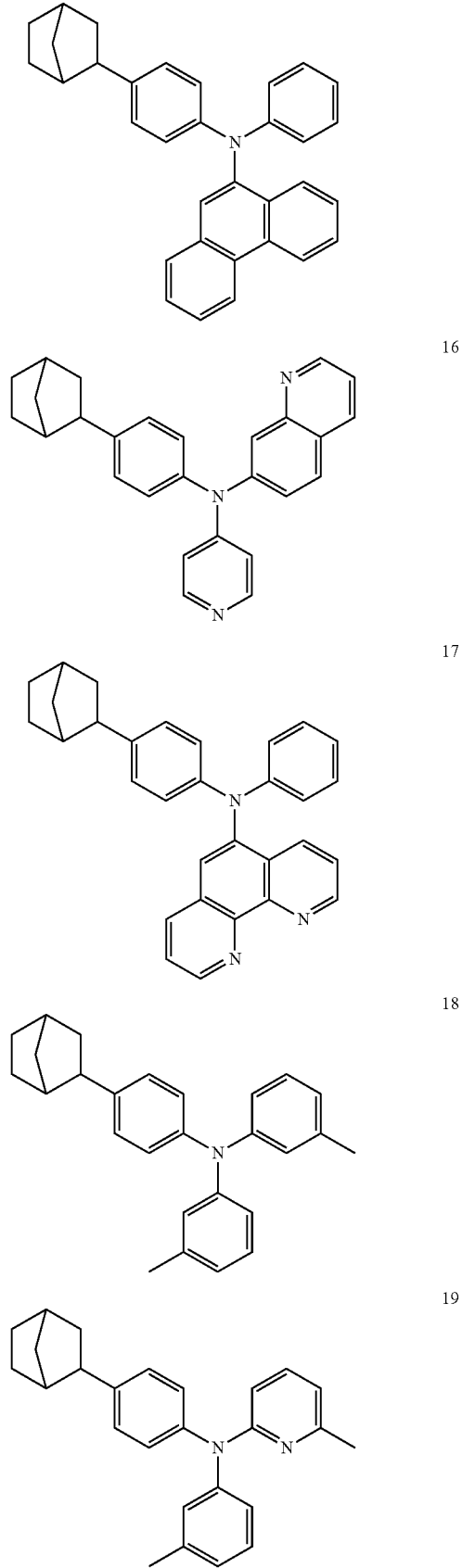

20
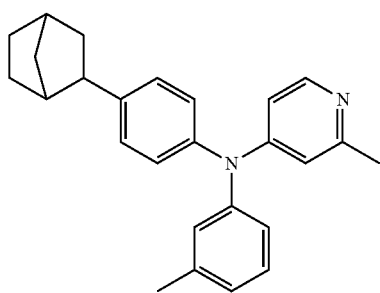
21
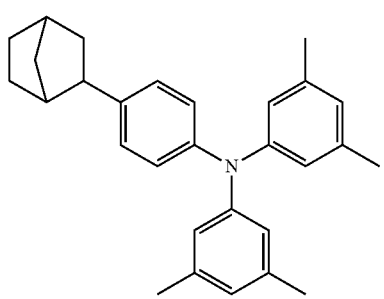
22
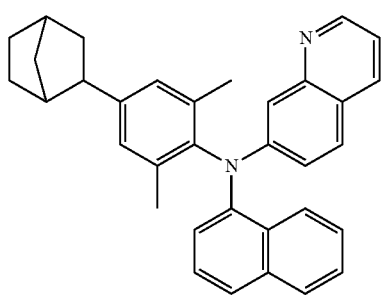
23
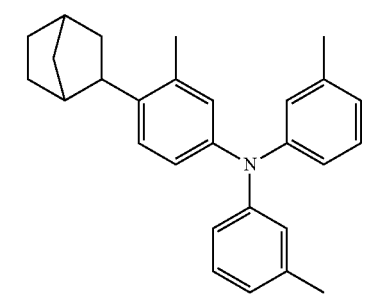
24
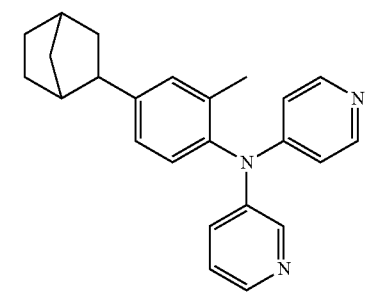
25
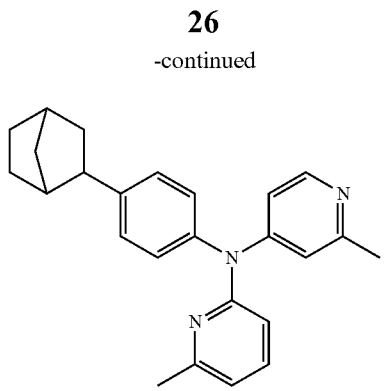
26
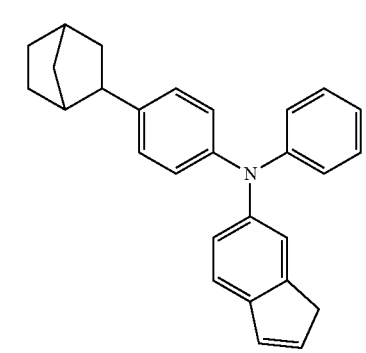
27
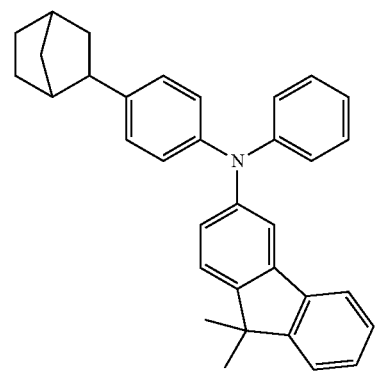
28
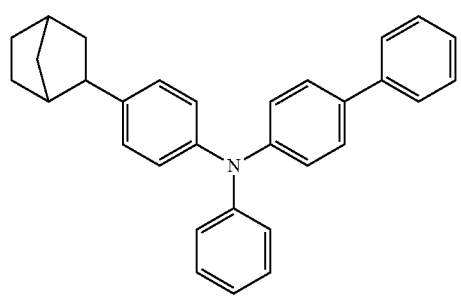

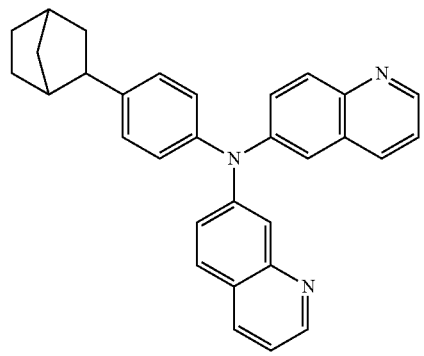
29
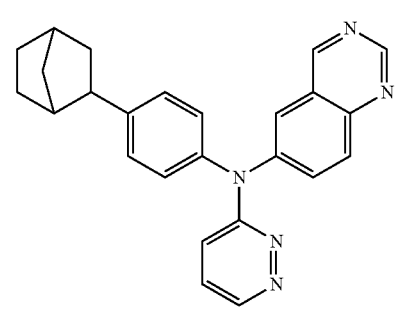
30
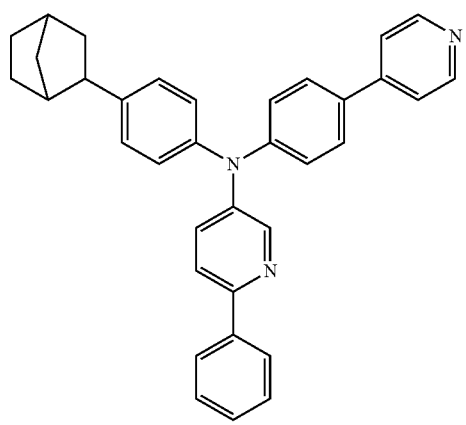
31
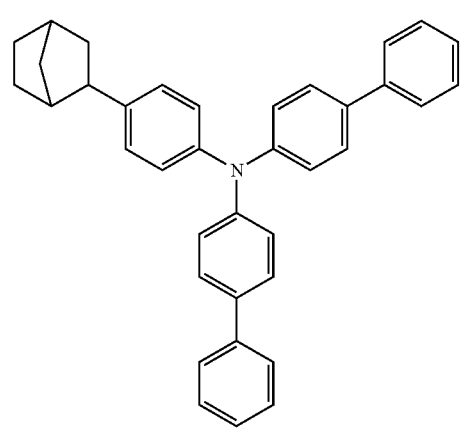
32
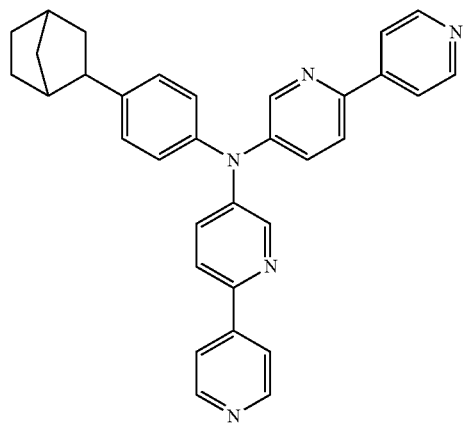
33
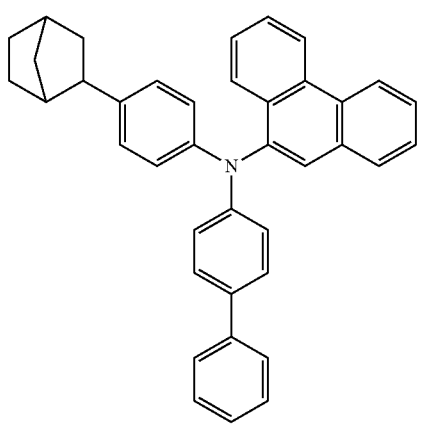
34
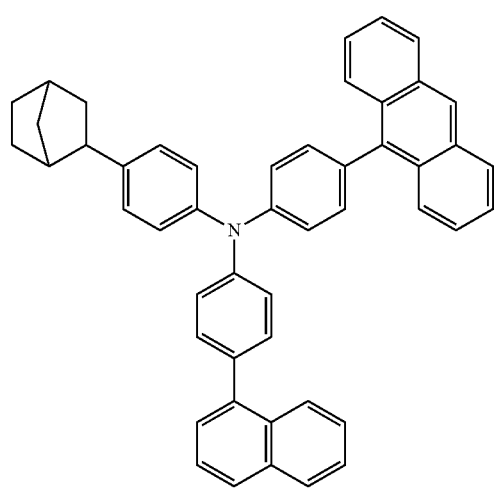
35

36
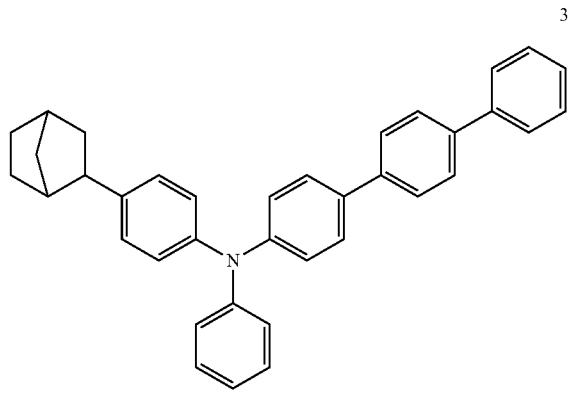
37
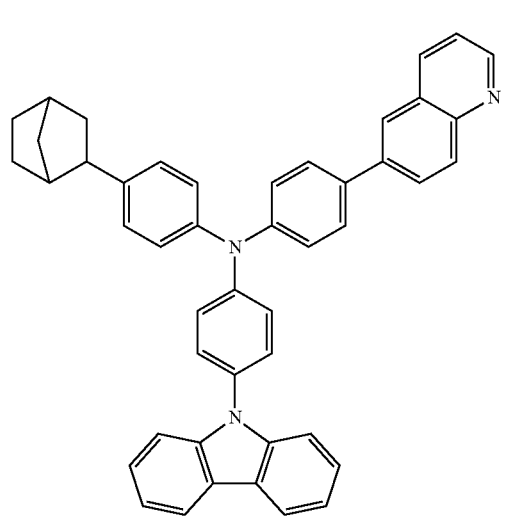
38
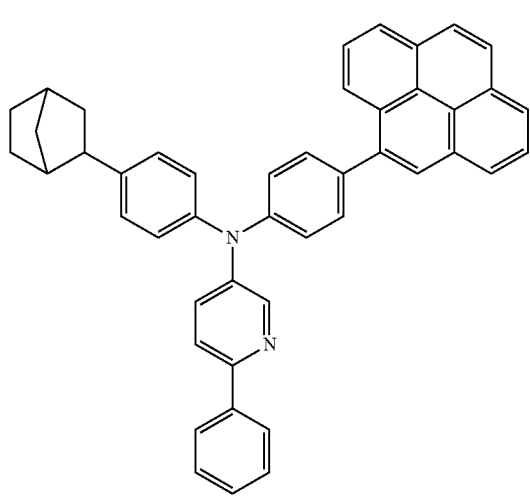
39
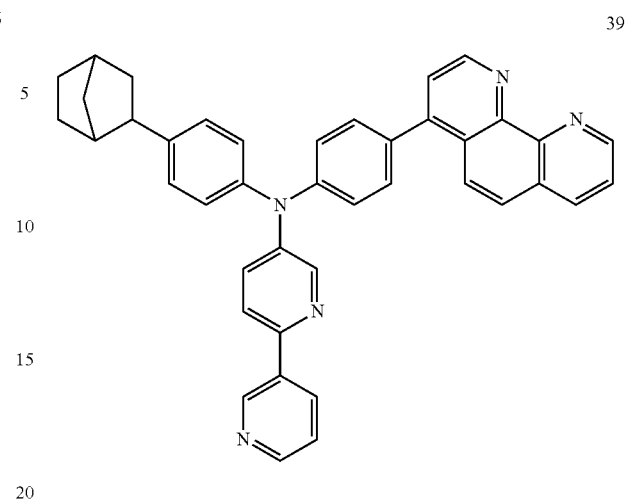
40
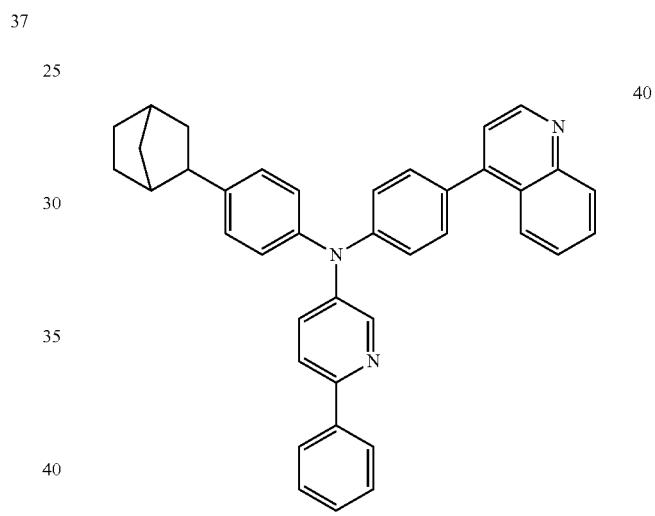
41
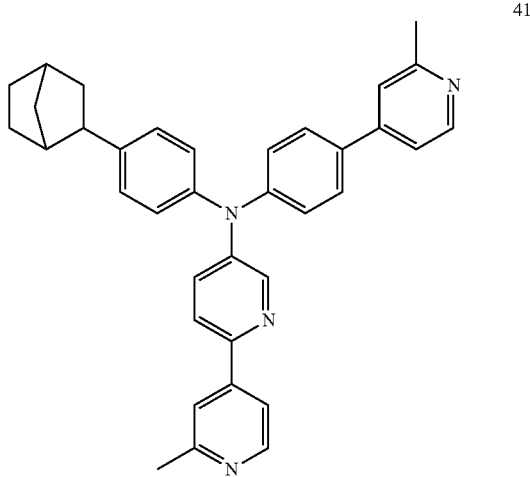

42
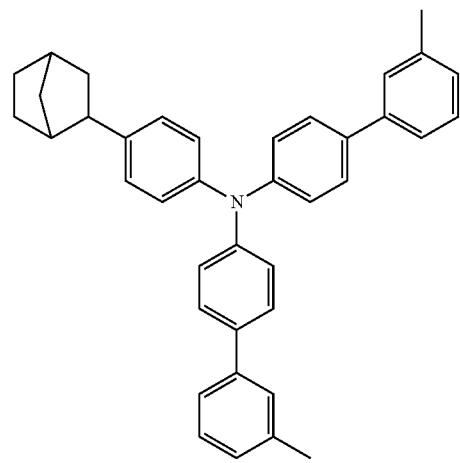
43
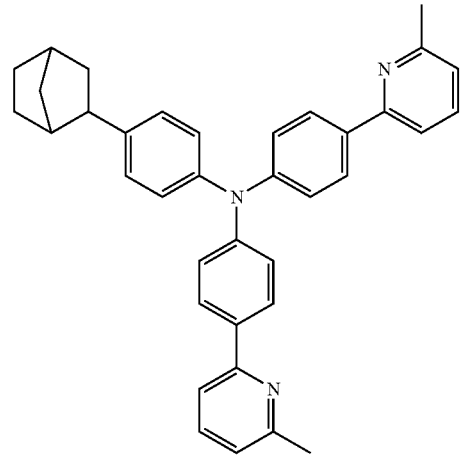
44
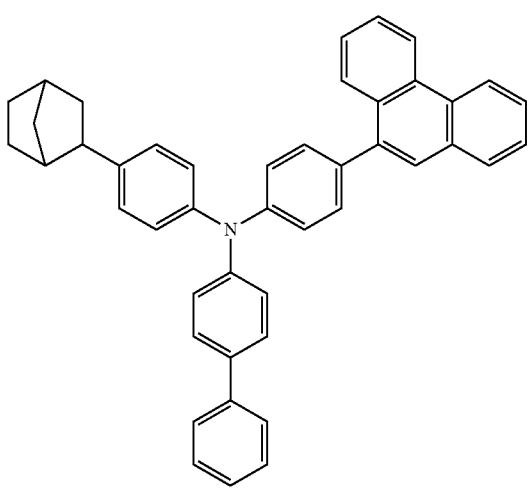
45
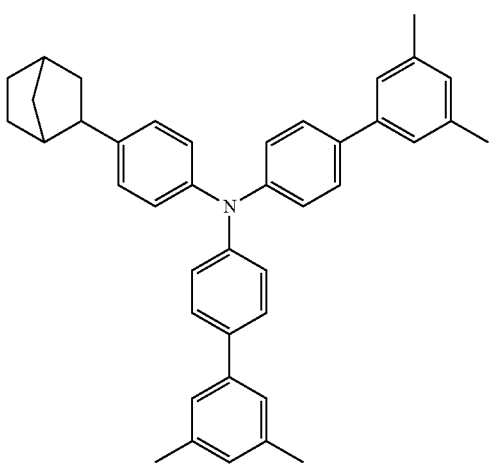
46
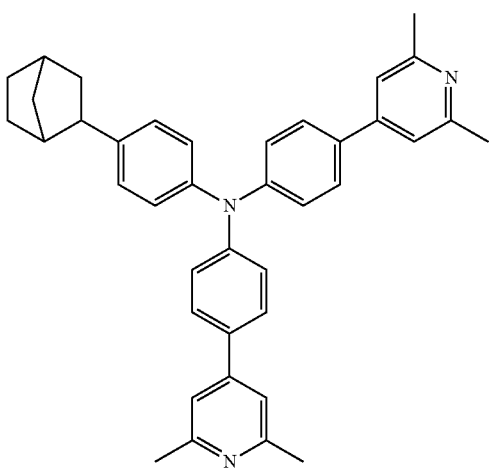
47
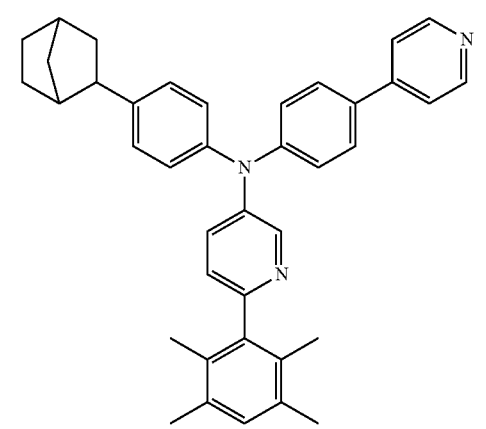
48
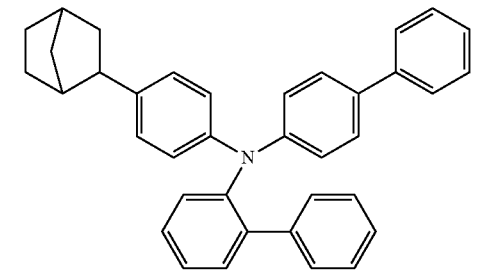

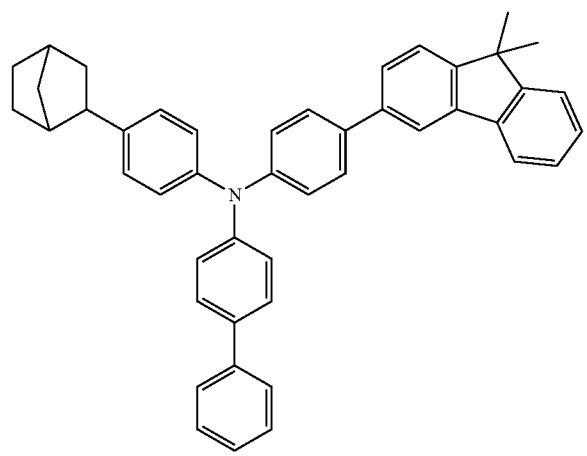
49
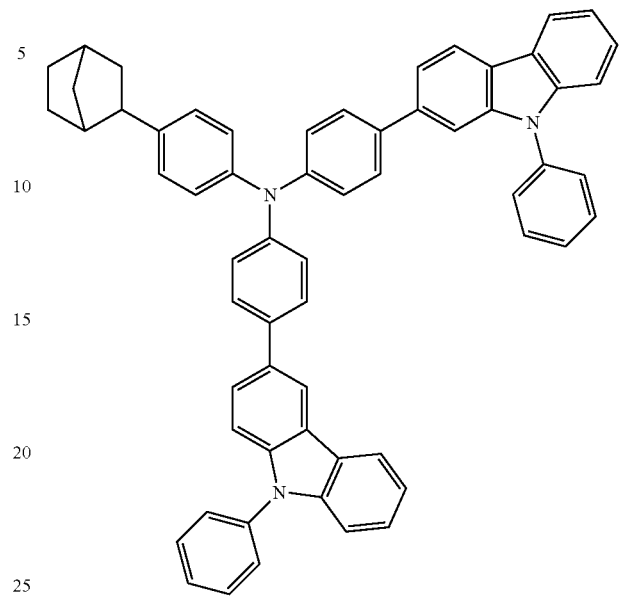
52
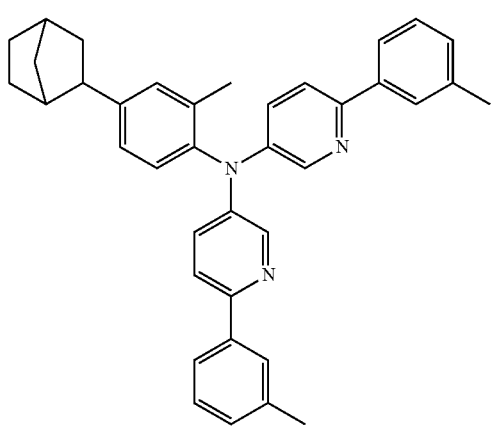
50
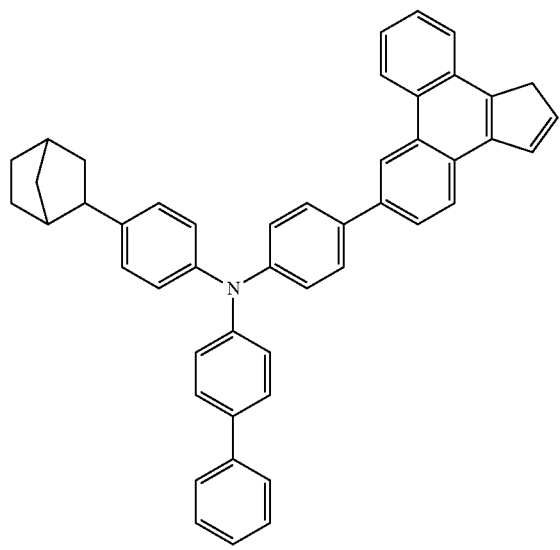
51
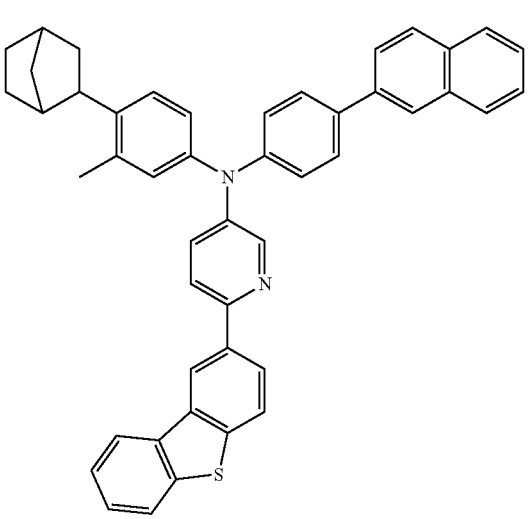
53

54
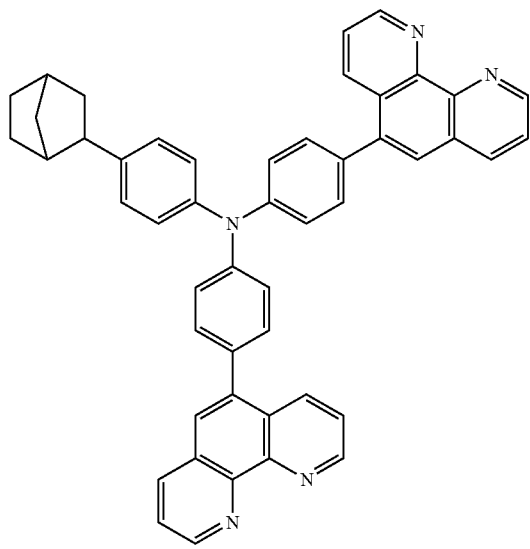
56
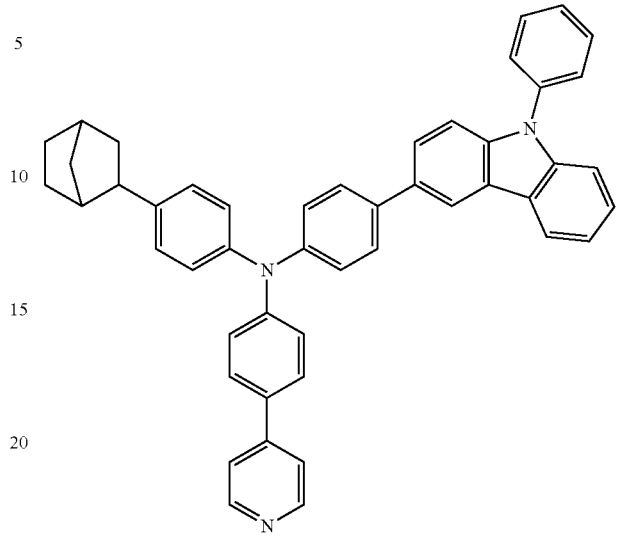
55
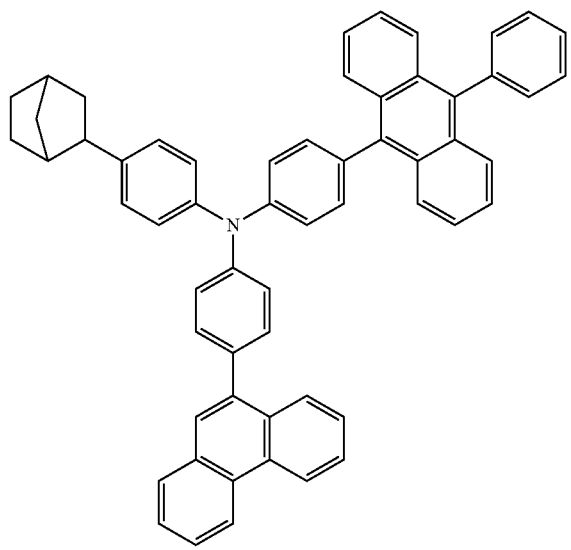
57
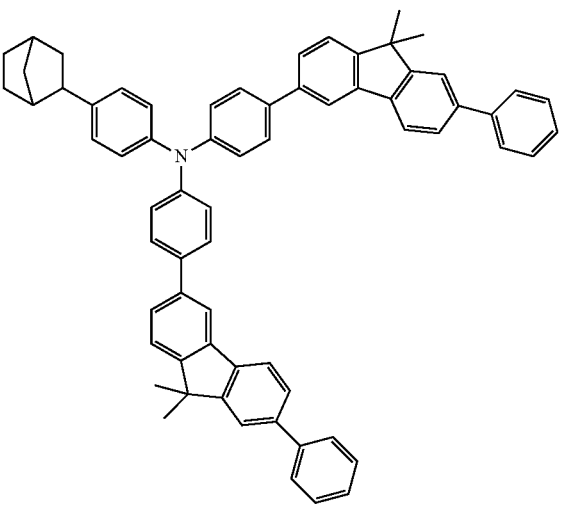

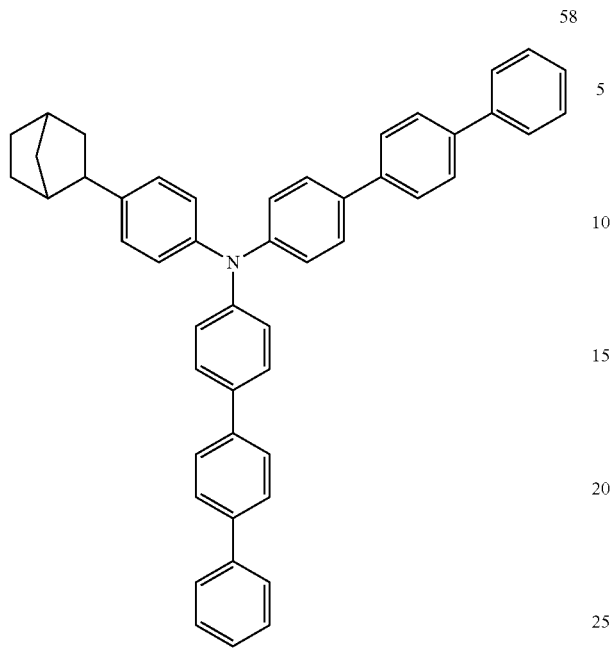
58
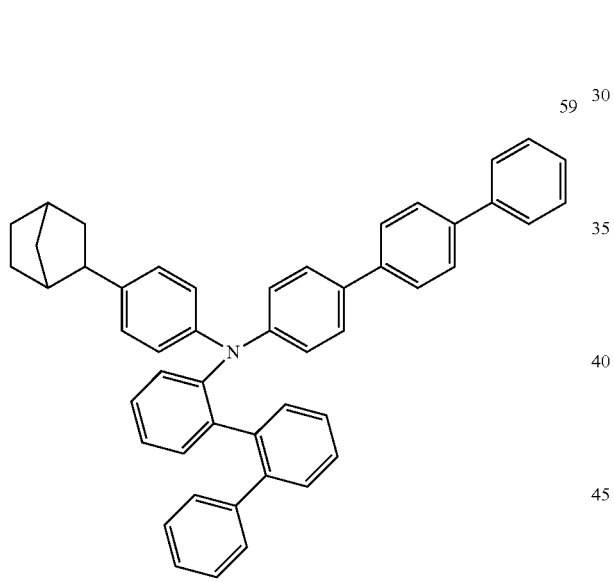
59
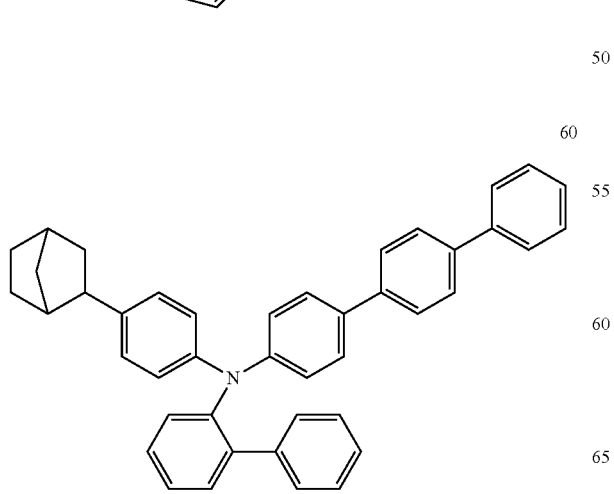
60
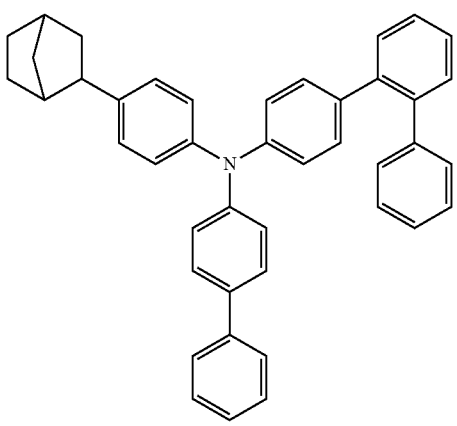
61
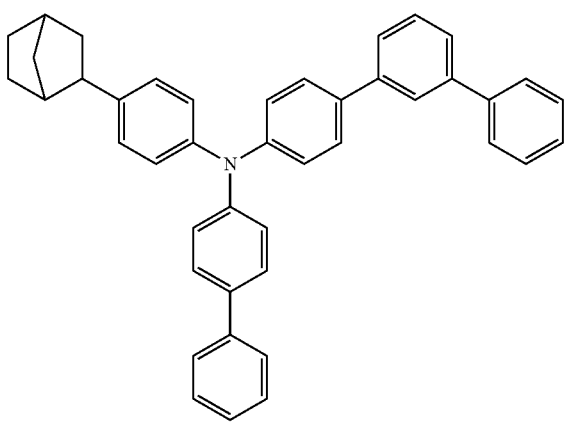
62
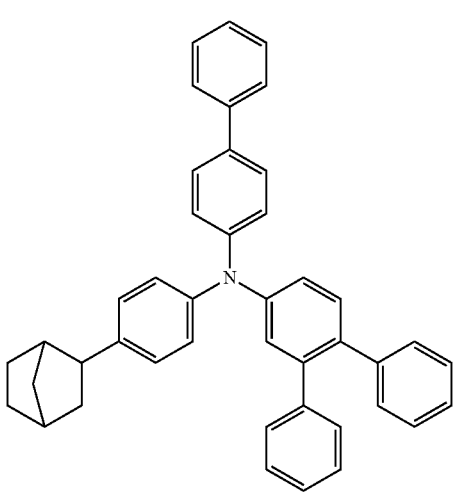
63

64
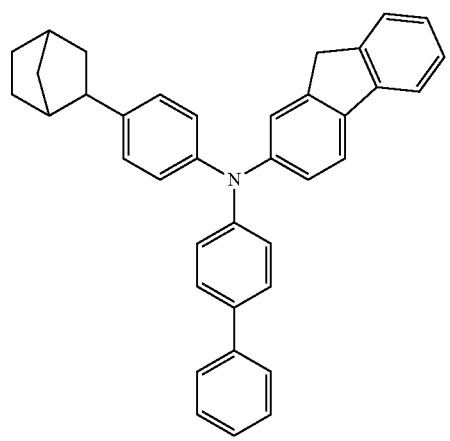
65
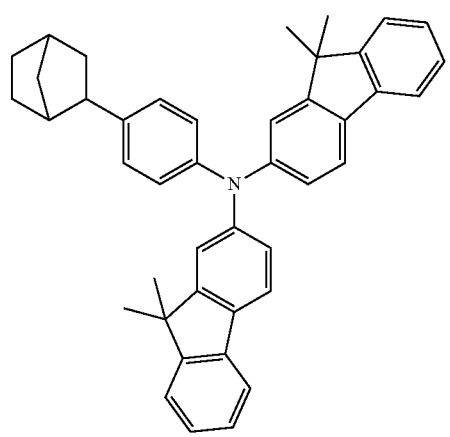
66
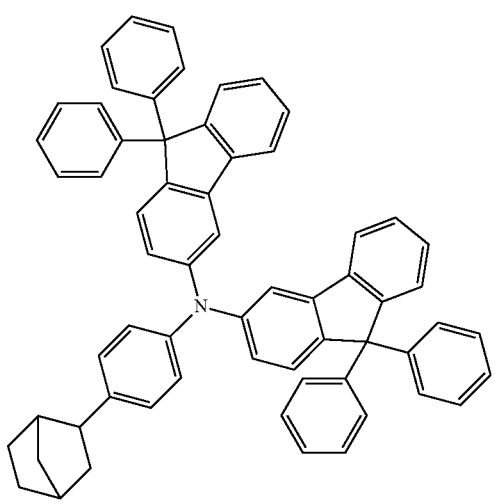
67
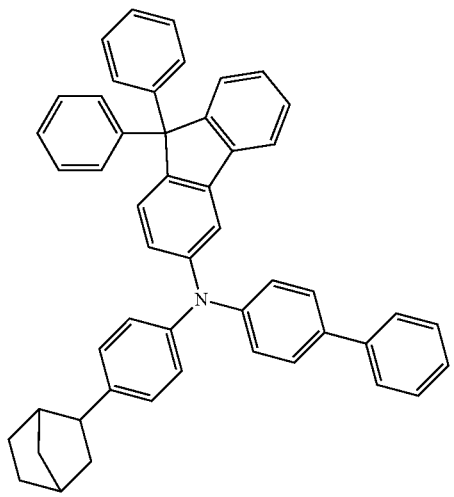
68
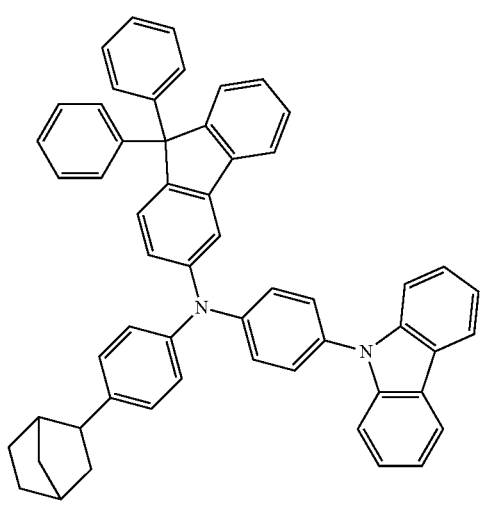
69
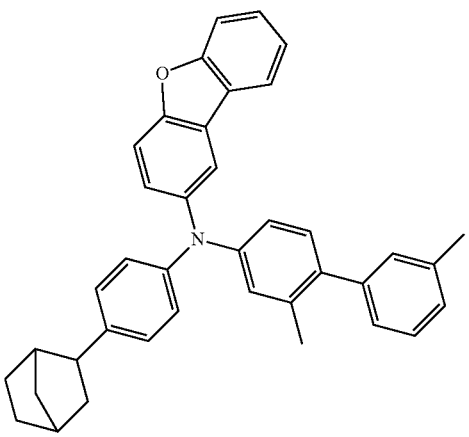

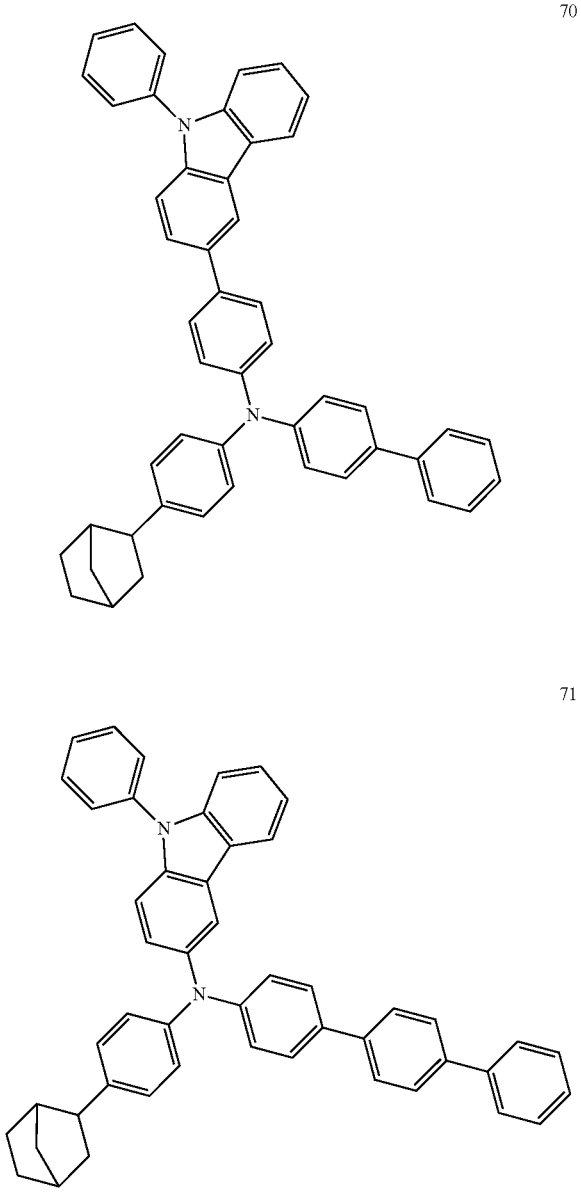
70
71
72
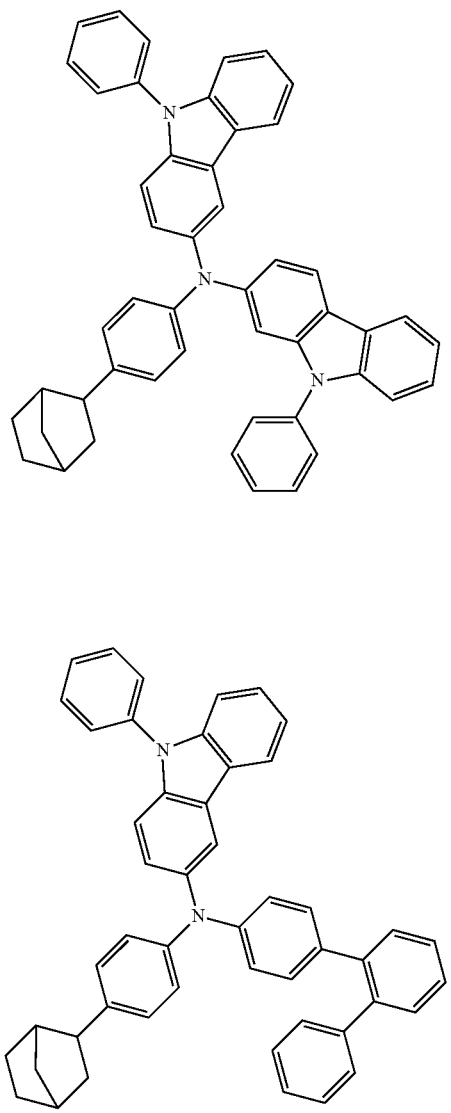
73
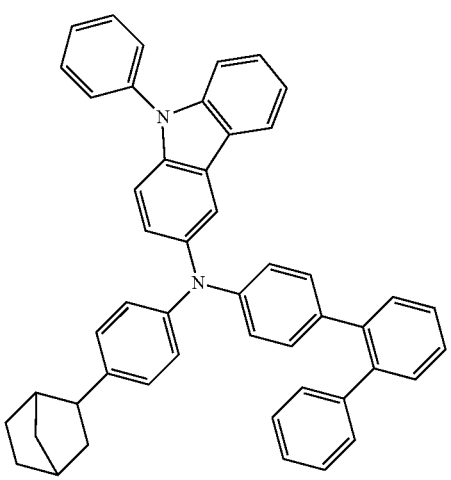
74
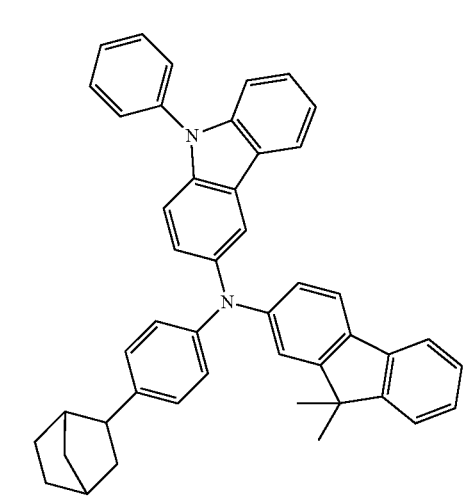
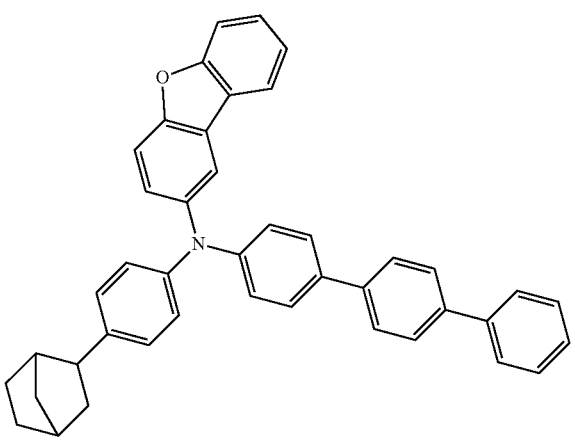
75

76
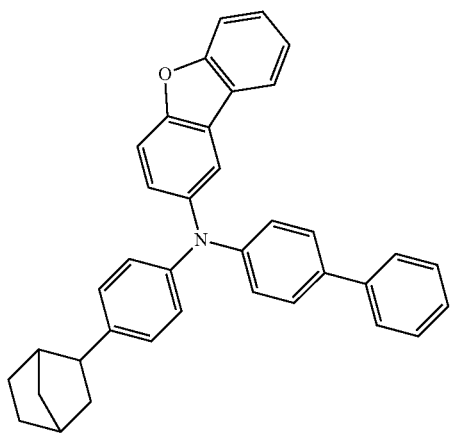
77
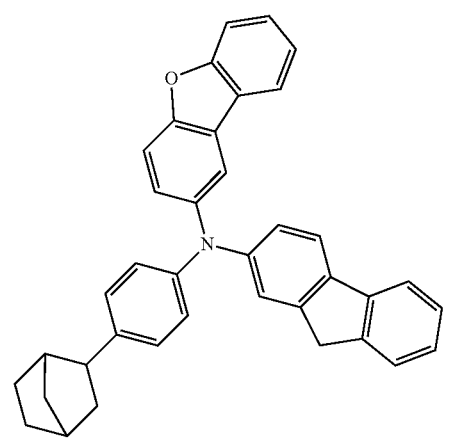
78
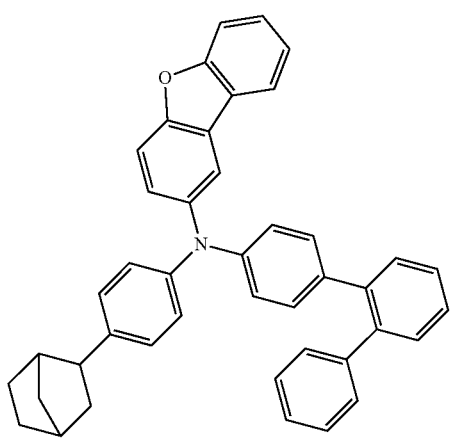
79
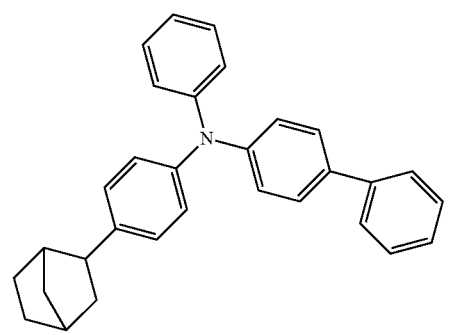
80
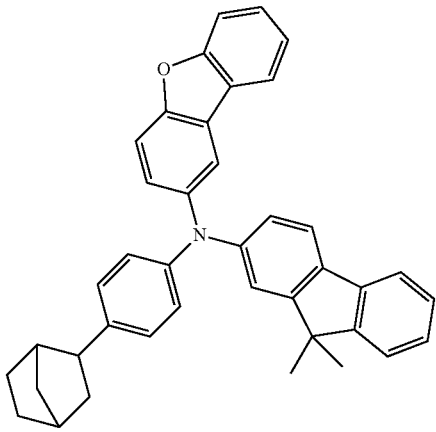
81
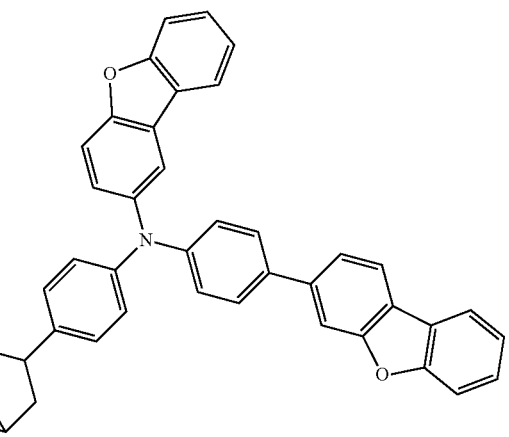
82
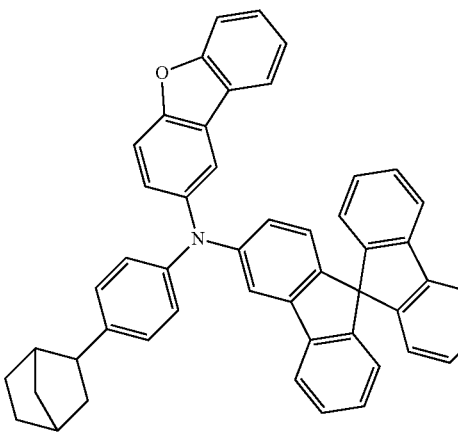

83
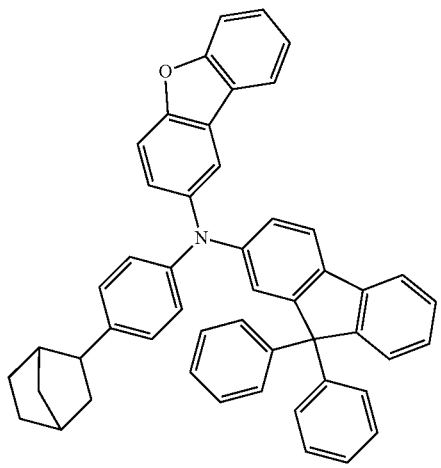
84
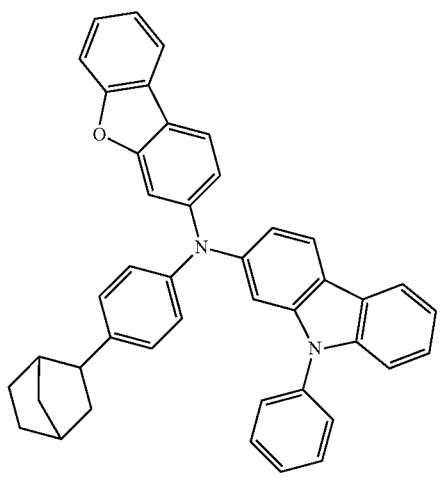
85
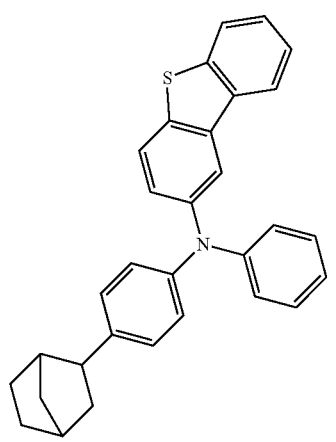
86
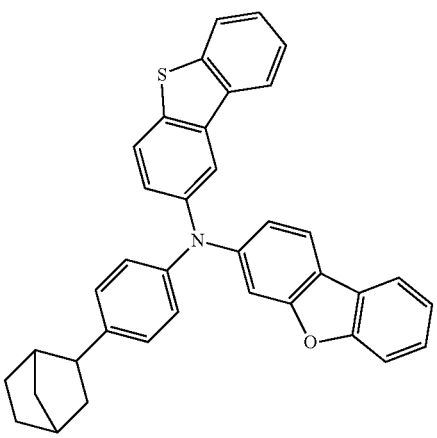
87
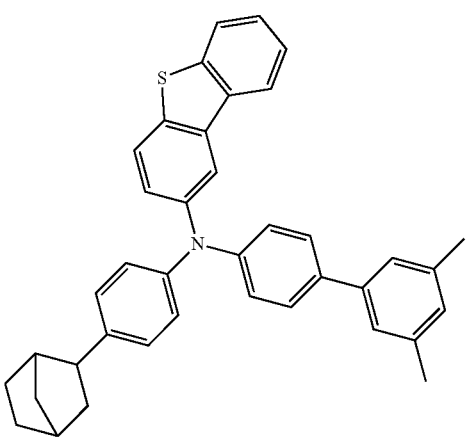
88

89
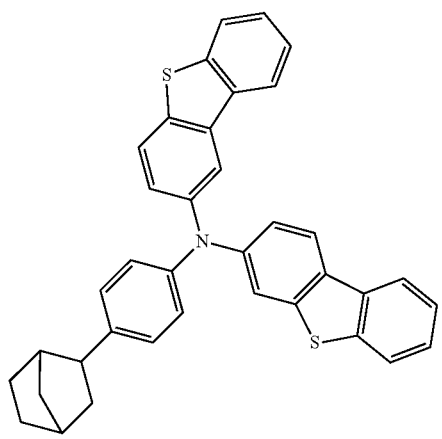
90
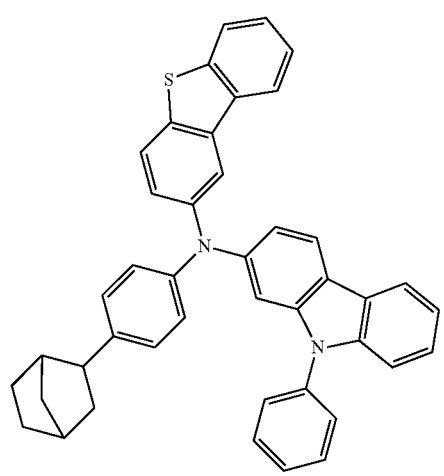
92
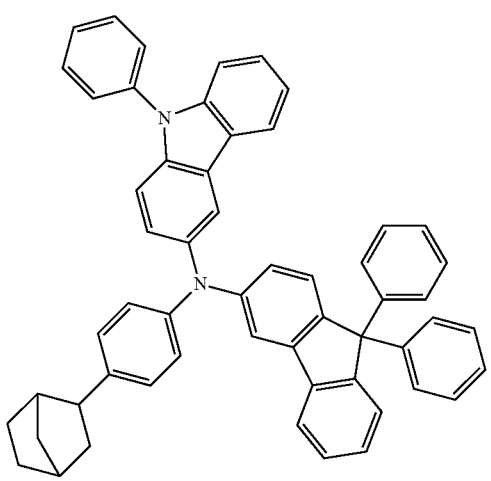
93
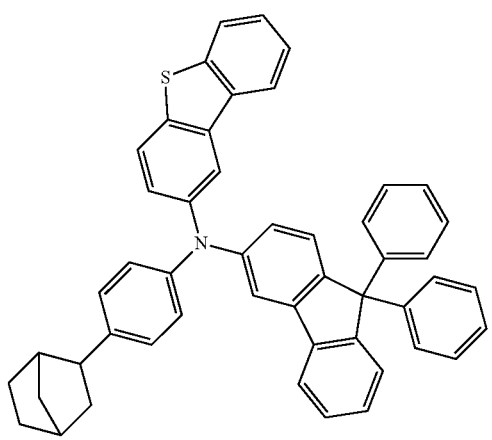
144
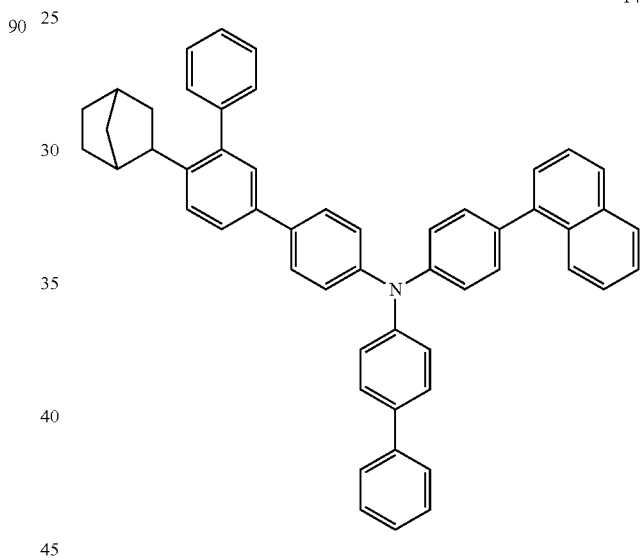
94
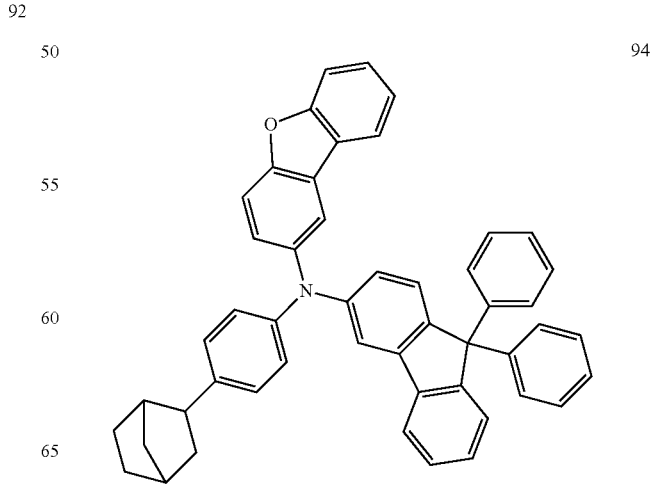

95
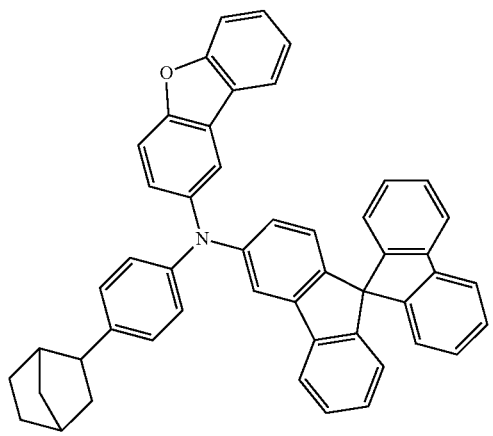
98
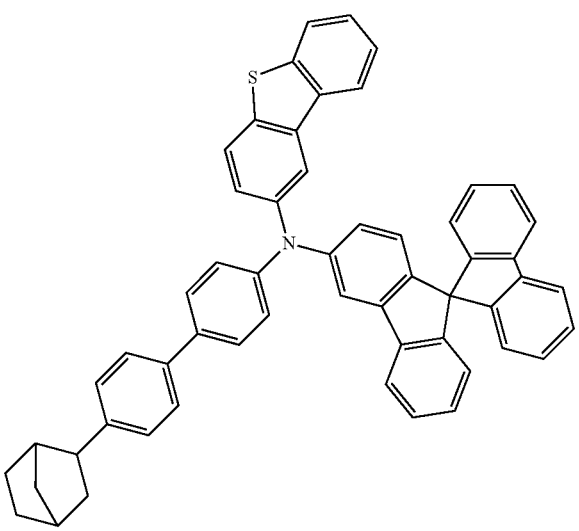
96
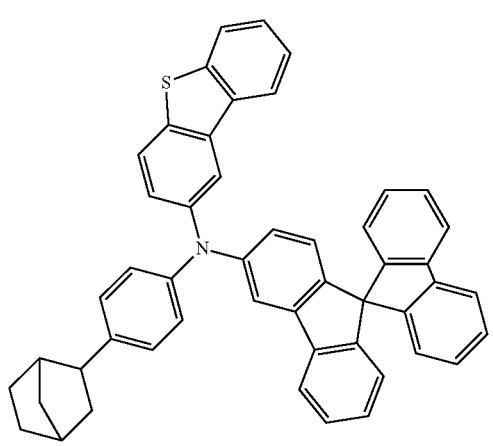
99
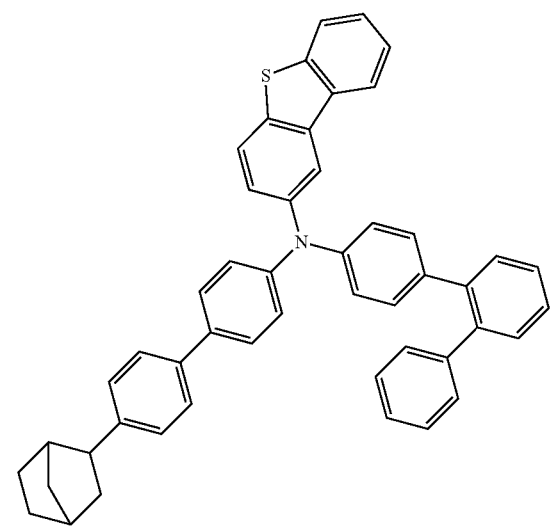
97
100
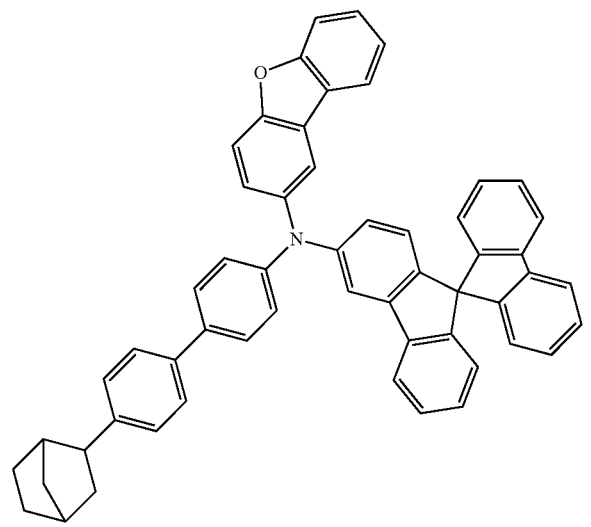

101
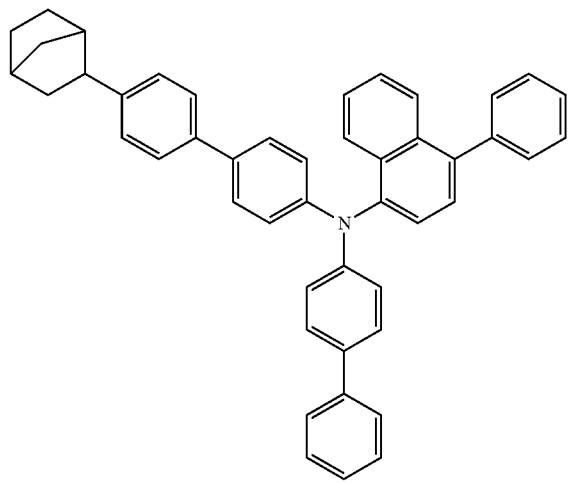
102
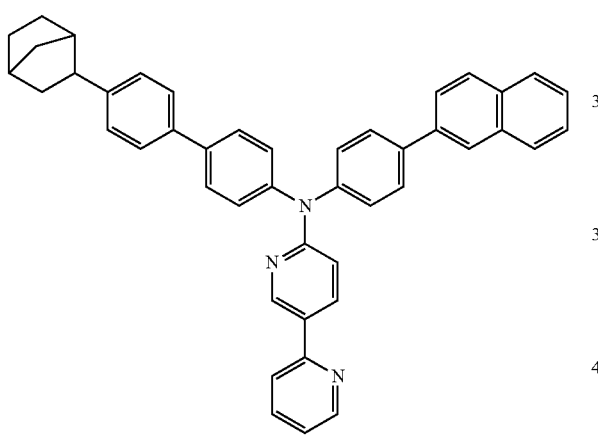
104
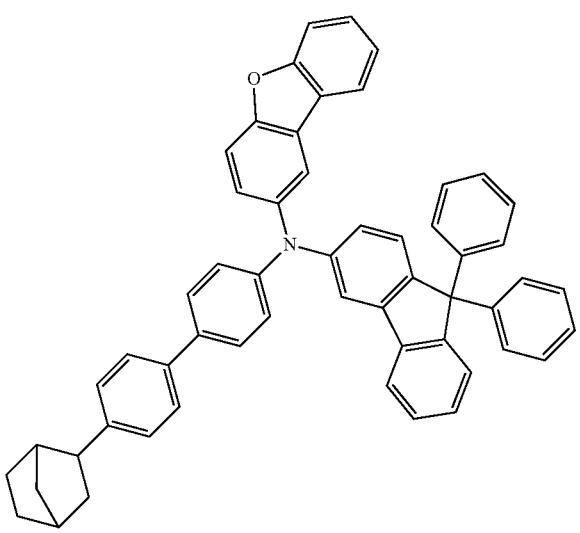
103
105
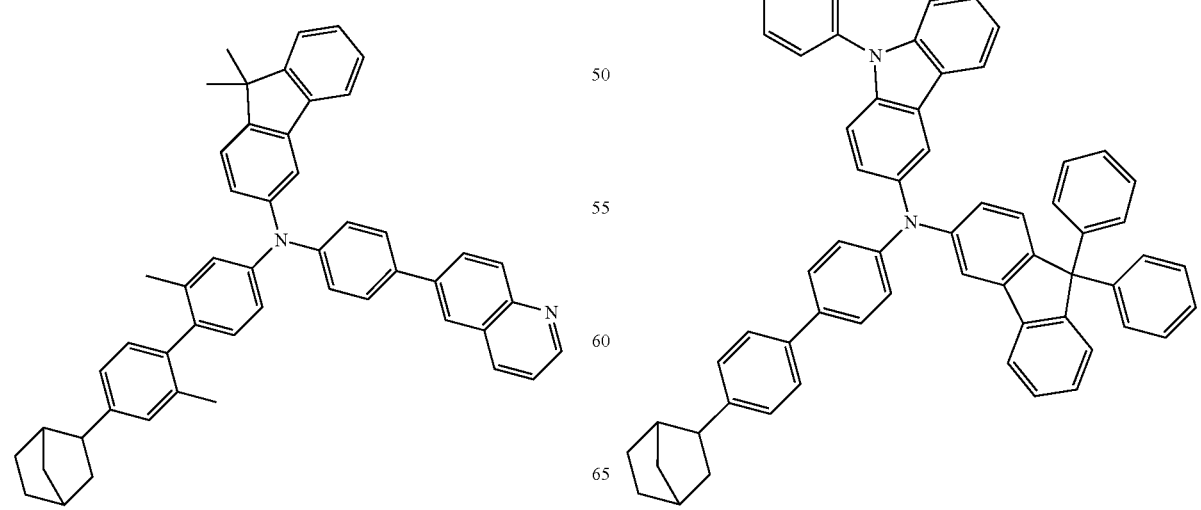

106
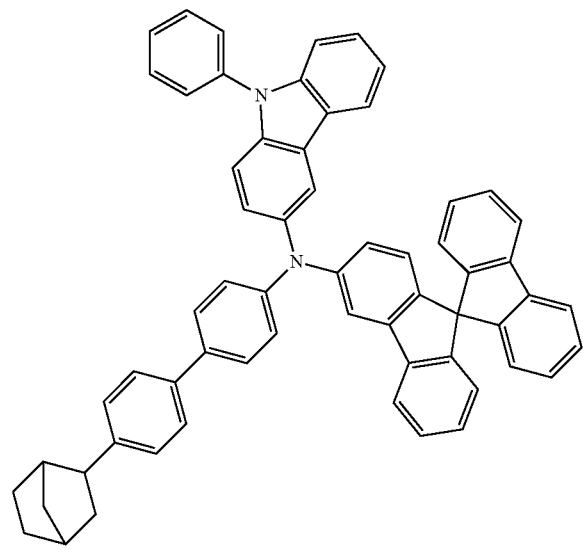
107
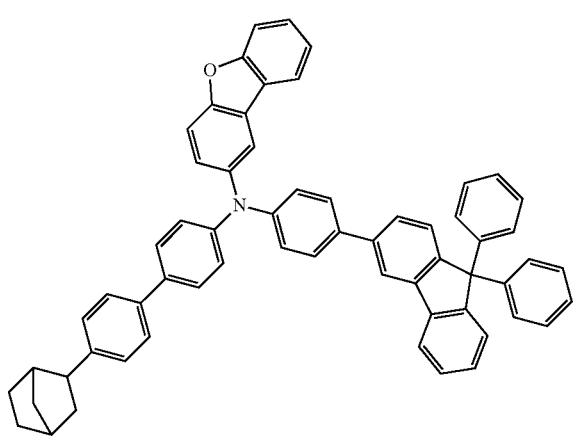
108
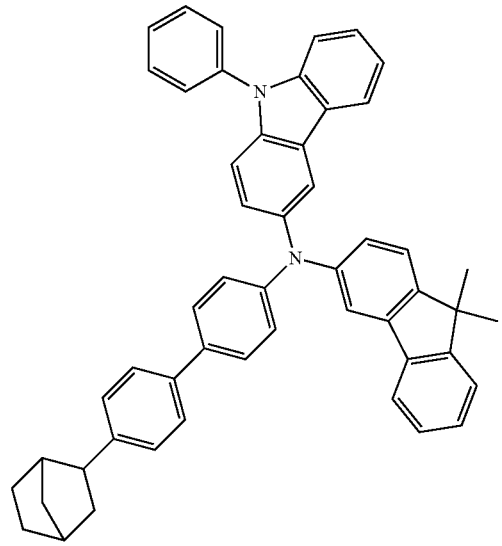
109
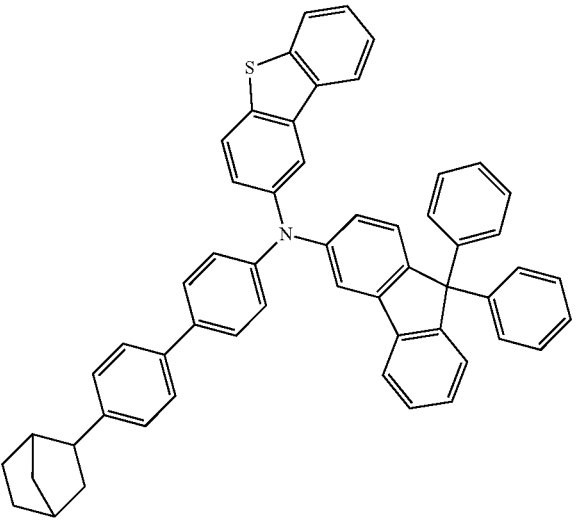
110
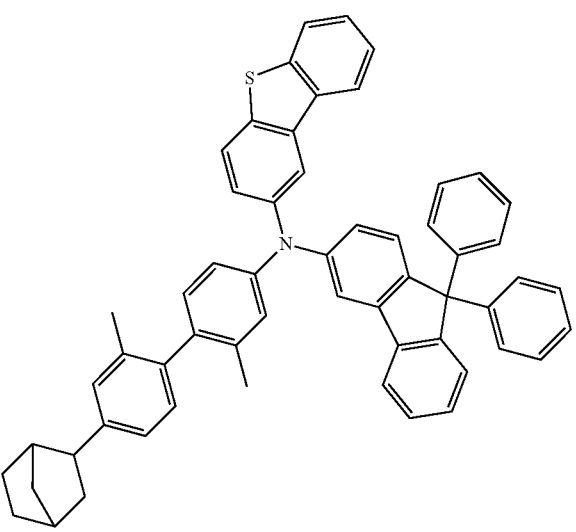
111
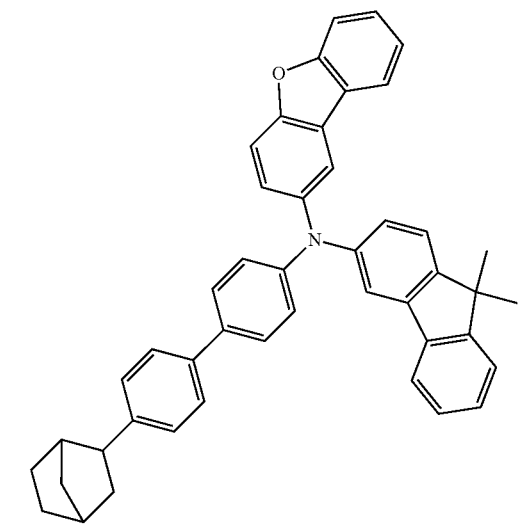

112
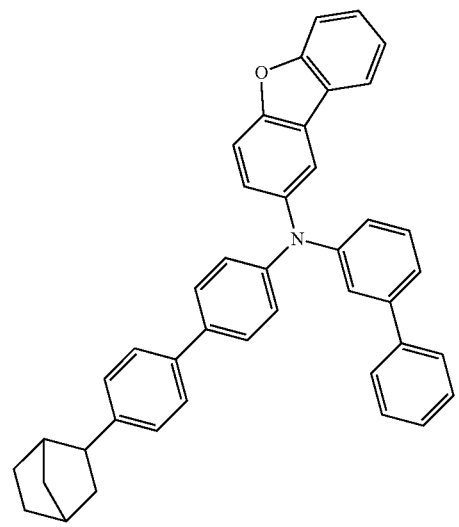
115
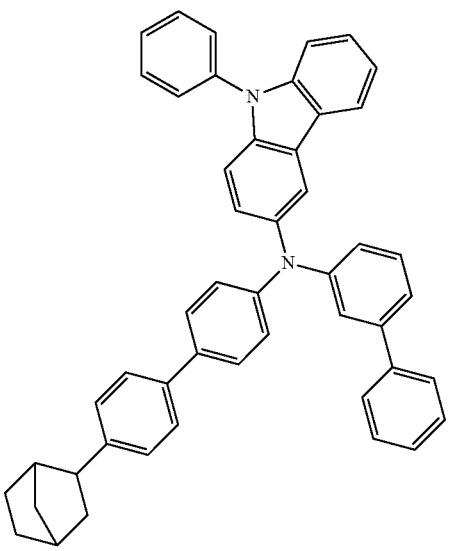
113
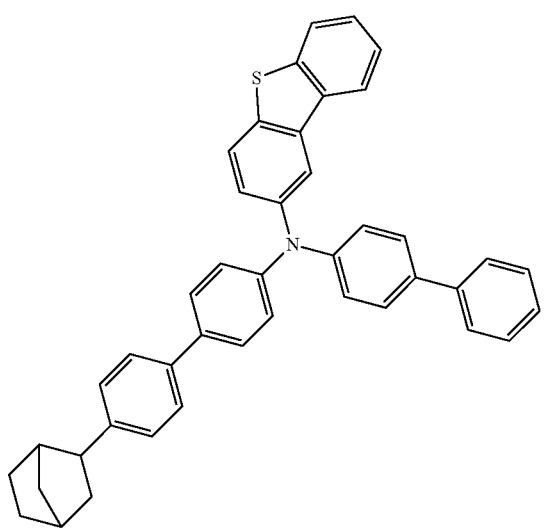
116
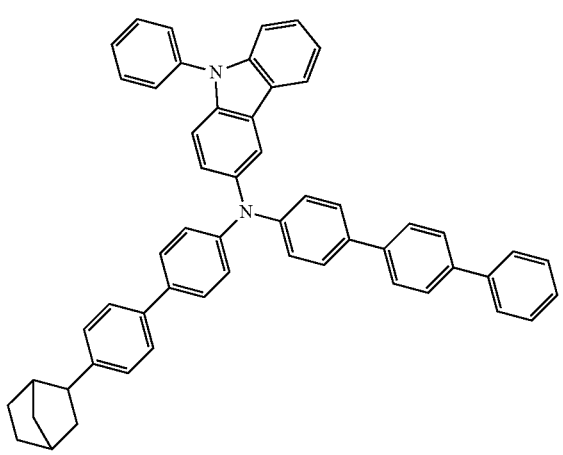
114
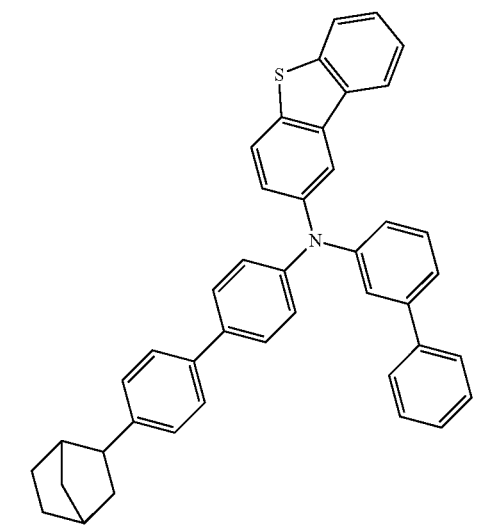
117
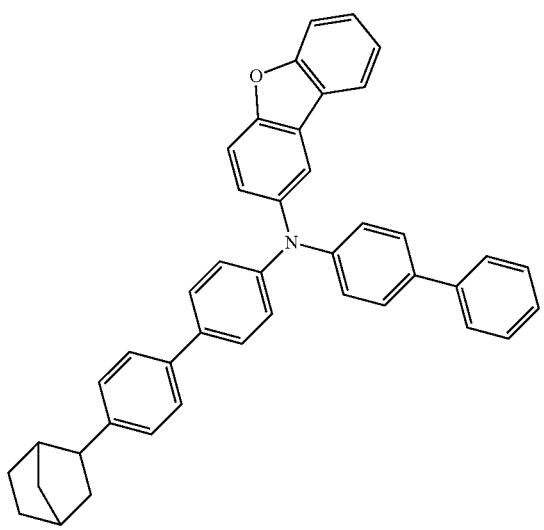

118
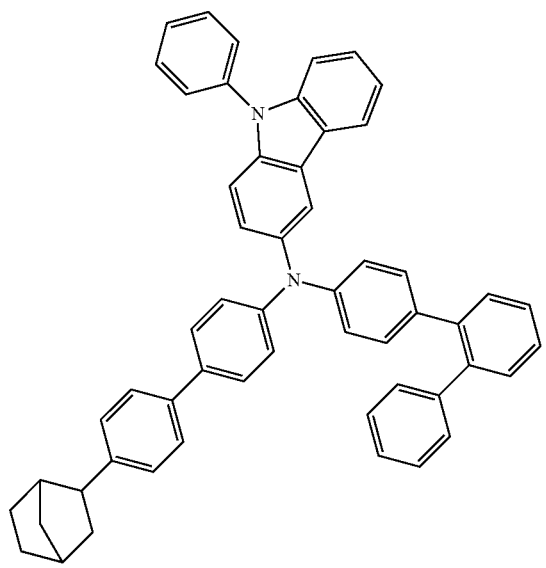
119
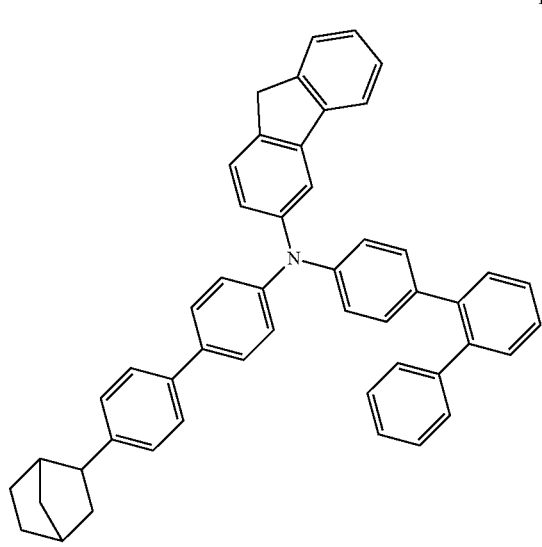
120
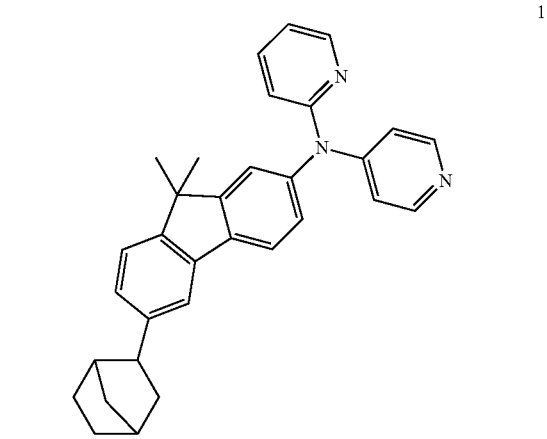
121
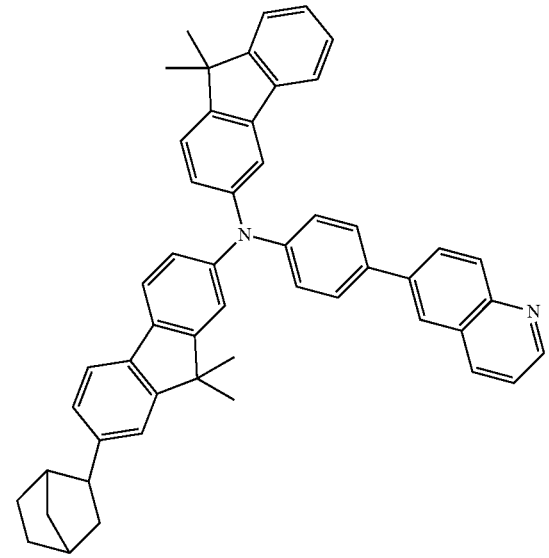
122
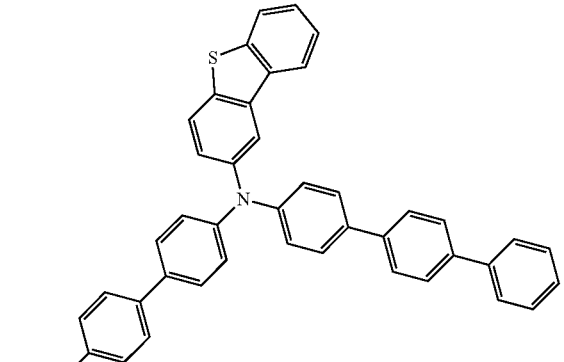
123
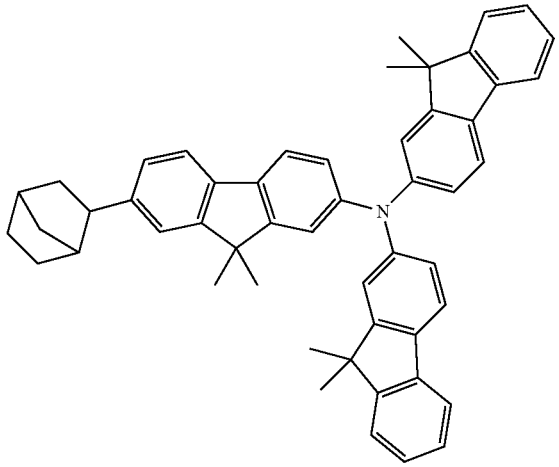

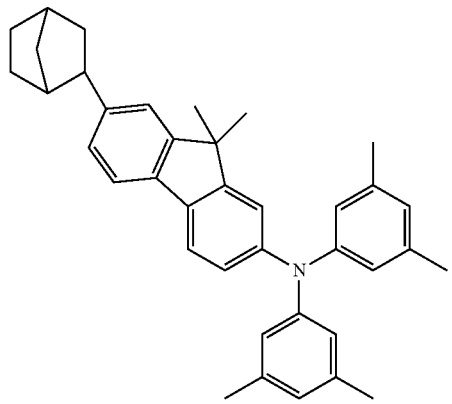
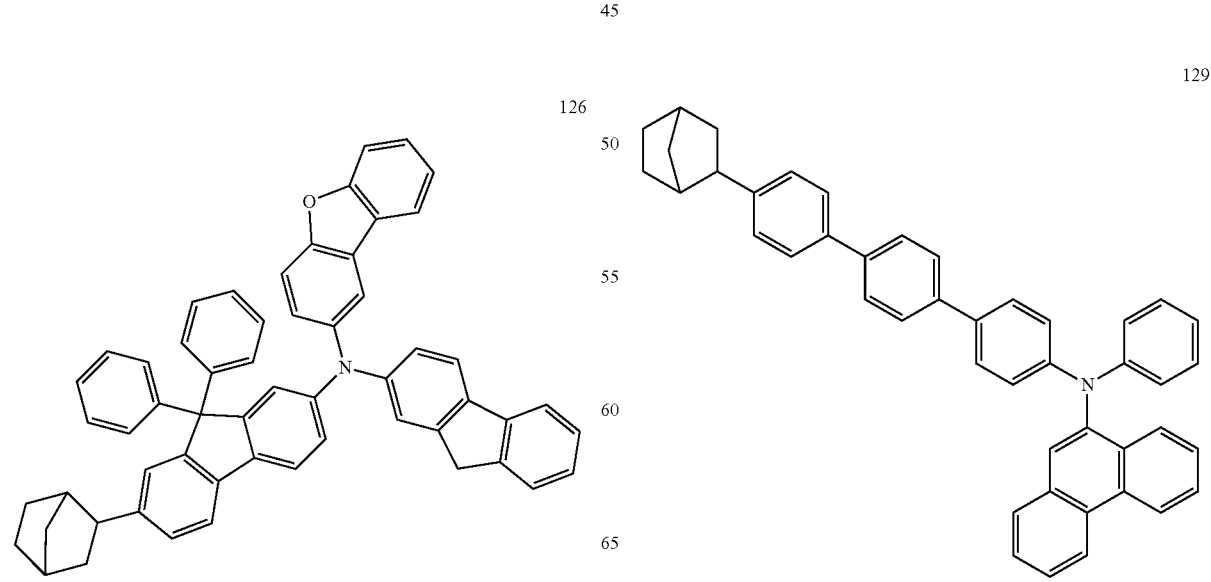

130
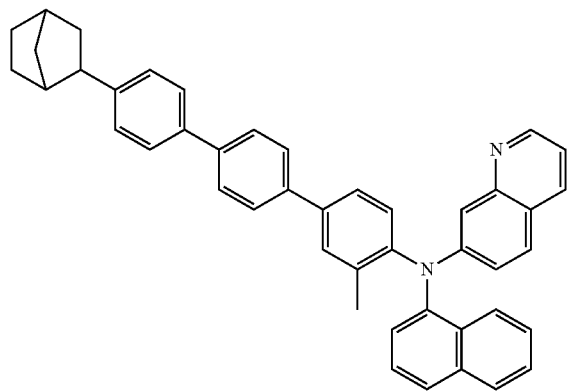
131
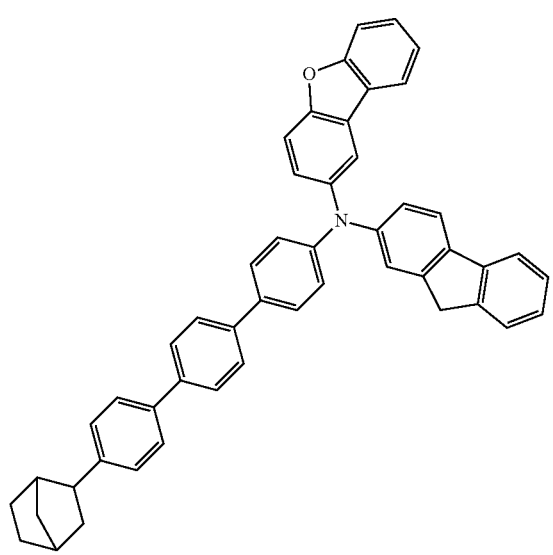
132
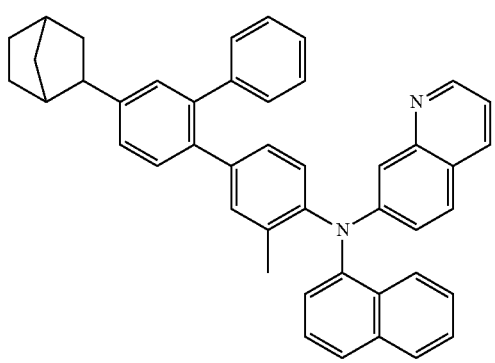
133
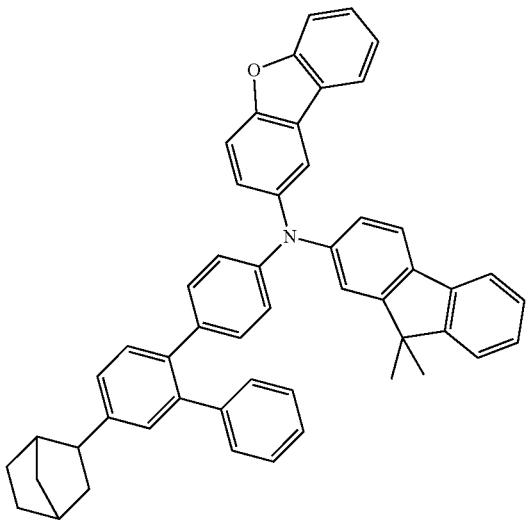
134
135
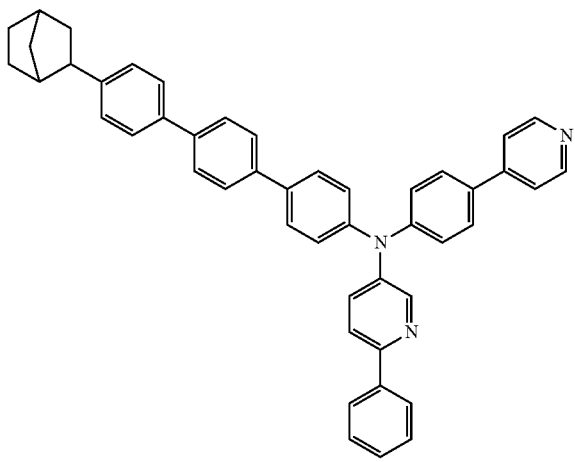

-continued
136
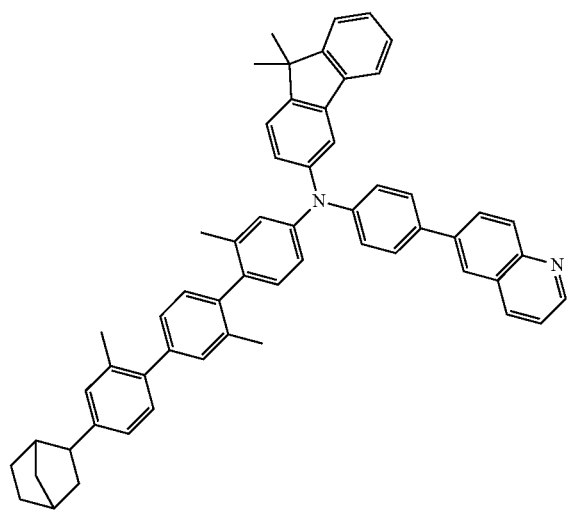
137
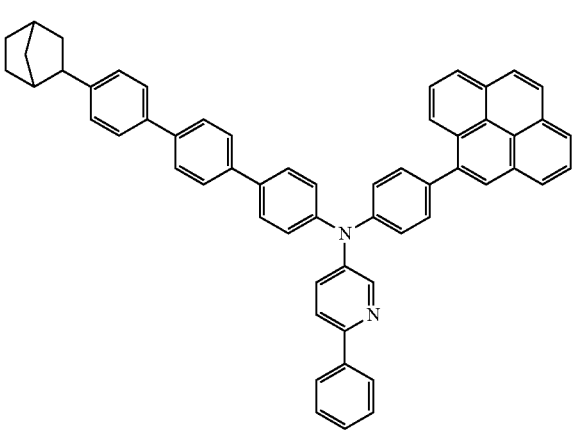
138
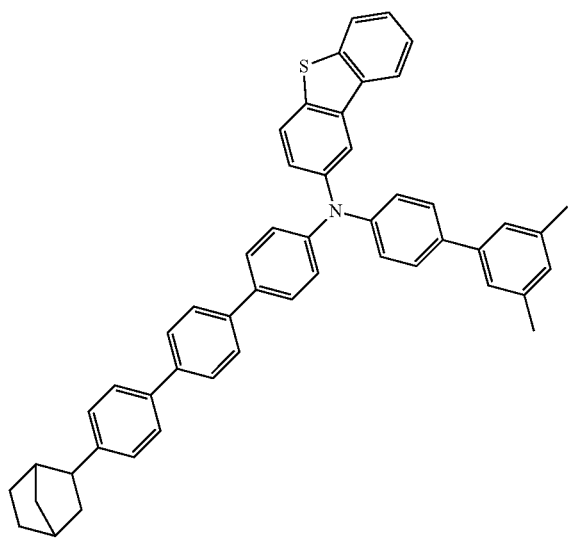
-continued
139
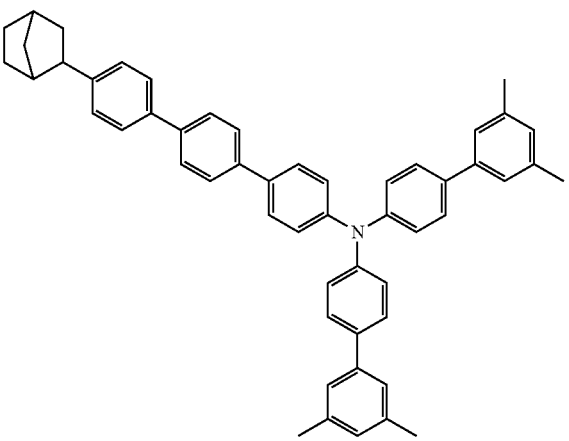
140
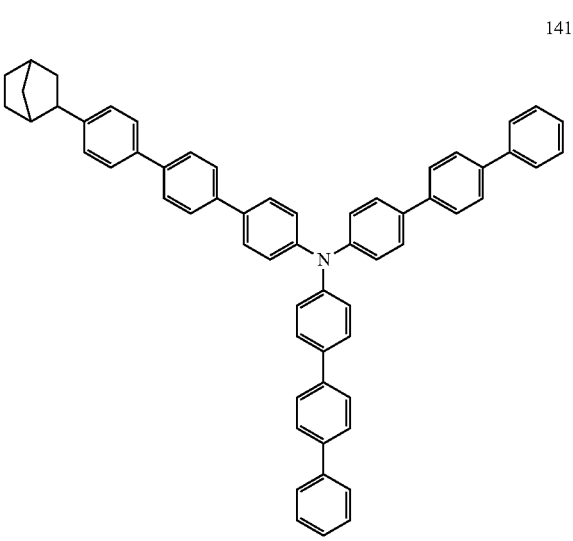
141

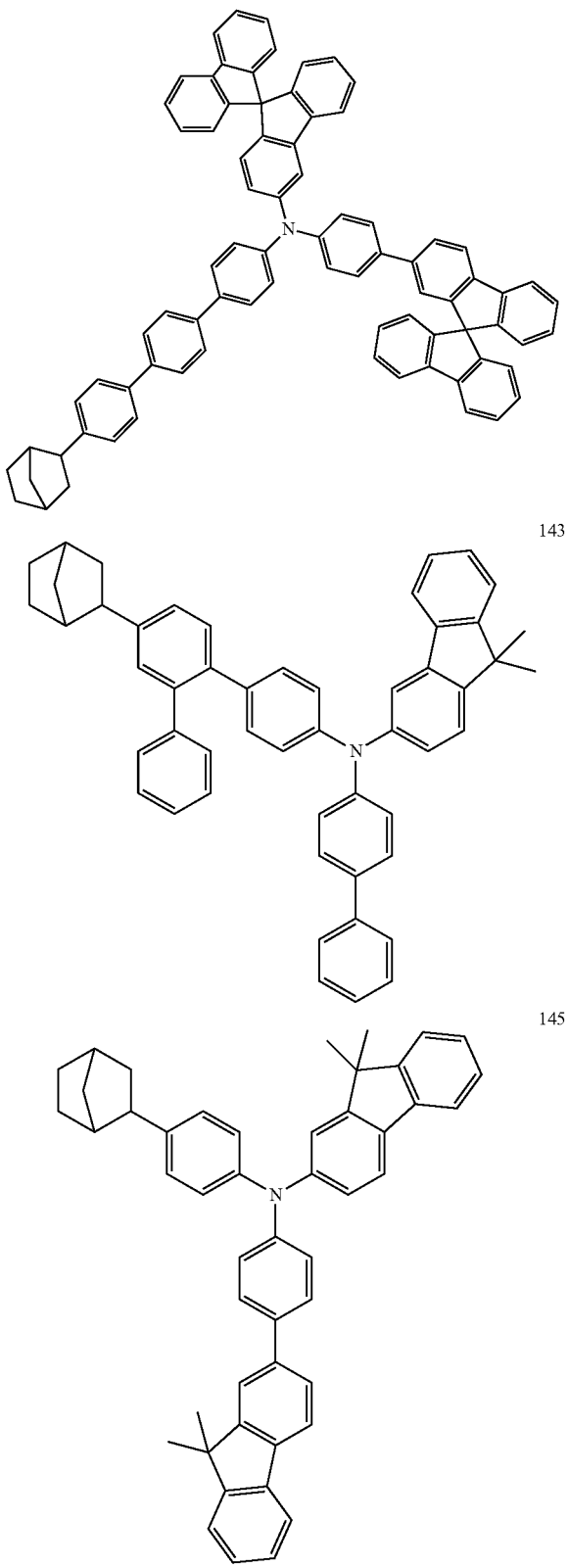

Optionally, the nitrogen-containing compound has a molecular weight lower than 750 so as to guarantee its lower evaporation temperature and higher thermal stability, improving its thermal stability when applied to mass production of organic electroluminescent devices or photoelectric conversion devices.

The present application also provides an electronic element, comprising an anode and a cathode which are oppositely disposed, and a functional layer disposed between the anode and the cathode; the functional layer contains the nitrogen-containing compound described above.

The nitrogen-containing compound provided by the present application may be used to form at least one organic film layer in the functional layer to improve the voltage characteristics, efficiency characteristics, and lifetime characteristics of the electronic element.

Optionally, the organic film layer containing the nitrogen-containing compound of the present application is positioned between the anode and the energy conversion layer of the electronic component so as to improve electron transport between the anode and the energy conversion layer.

For example, the electronic component may be an organic electroluminescent device. As shown in FIG. 1, the organic electroluminescent device includes an anode 100 and a cathode 200 which are oppositely disposed, and a functional layer 300 disposed between the anode 100 and the cathode 200; the functional layer 300 contains the nitrogen-containing compound provided by the present application.

Optionally, the nitrogen-containing compound provided by the present application may be used to form at least one organic film layer in the functional layer 300 to improve the service life characteristics, efficiency characteristics, electrochemical stability, and thermal stability of the organic electroluminescent device and reduce the driving voltage; in certain embodiments, the mass production stability of the organic electroluminescent device may also be improved.

Optionally, the functional layer 300 includes a hole transport layer 320 containing the nitrogen-containing compound provided by the present application. The hole transport layer 320 may be composed of the nitrogen-containing compound provided by the present application, or may be composed of the nitrogen-containing compound provided by the present application and other materials.

Optionally, the hole transporting layer 320 includes a first hole transporting layer 321 and a second hole transporting layer 322, and the first hole transporting layer 321 is disposed on a surface of the second hole transporting layer 322 close to the anode 100; the first hole transport layer 321 or the second hole transport layer 322 contains the nitrogen-containing compound provided by the present application. Among them, one of the first hole transporting layer 321 or the second hole transporting layer 322 may contain the nitrogen-containing compound provided by the present application, or both the first hole transporting layer 321 and the second hole transporting layer 322 may contain the nitrogen-containing compound provided by the present application. It can be understood that the first hole transport layer 321 or the second hole transport layer 322 may also contain other materials or may not contain other materials. It can be understood that in another embodiment of the present application, the second hole transport layer 322 may be used as an electron blocking layer of the organic electroluminescent device.

In one embodiment of the present disclosure, as shown in FIG. 1, the organic electroluminescent device may include an anode 100, a first hole transport layer 321, a second hole transport layer 322, an organic light-emitting layer 330 as an energy conversion layer, an electron transport layer 340, and a cathode 200 which are stacked in sequence. The nitrogen-containing compound provided by the present application may be applied to the first hole transport layer 321 or the second hole transport layer 322 of the organic electroluminescent device, and may be effective in improving the hole characteristics of the organic electroluminescent device. Wherein, the hole characteristics mean that holes formed in the anode 100 are easily injected into the organic electroluminescent layer 330, and are transported in the organic electroluminescent layer 330 according to the conduction characteristics of the HOMO level.

Optionally, the anode 100 includes an anode material, which is preferably a material having a large work function that facilitates hole injection into the functional layer. Specific examples of the anode material include metals such as nickel, platinum, vanadium, chromium, copper, zinc, and gold or alloys thereof; metal oxides such as zinc oxide, indium oxide, indium tin oxide (ITO), and indium zinc oxide (IZO); combined metals and oxides such as ZnO:Al or $SnO_2$:Sb; or conducting polymers such as poly(3-methylthiophene), poly[3,4-(ethylene-1,2-dioxy)thiophene] (PEDT), polypyrrole, and polyaniline, but are not limited thereto. A transparent electrode containing indium tin oxide (ITO) is preferably included as an anode.

Optionally, the organic electroluminescent layer 330 may consist of a single light-emitting material and may also include a host material and a guest material. Optionally, the organic electroluminescent layer 330 is composed of a host material and a guest material, and holes injected into the organic electroluminescent layer 330 and electrons injected into the organic electroluminescent 330 may be recombined in the organic electroluminescent layer 330 to form excitons, the excitons transfers energy to the host material, and the host material transfers energy to the guest material, thereby enabling the guest material to emit light.

The host material of the organic electroluminescent layer 330 may be a metal chelated compound, a bis-styryl derivative, an aromatic amine derivative, a dibenzofuran derivative or other types of materials, which is not specially limited by the present application. In one embodiment of the present disclosure, the host material of the organic electroluminescent layer 330 may be CBP. In another embodiment of the present application, the host material of the organic electroluminescent layer 330 can be α, β-ADN.

The guest material of the organic electroluminescent layer 330 may be a compound having a condensed aryl ring or a derivative thereof, a compound having a heteroaryl ring or a derivative thereof, an aromatic amine derivative, or other materials, which is not specially limited by the present application. In one embodiment of the present disclosure, the guest material of the organic electroluminescent layer 330 may be $Ir(piq)_2(acac)$. In another embodiment of the present application, the guest material of the organic electroluminescent layer 330 may be BD-1.

The electron transport layer 340 may be a single layer structure or a multi-layer structure, and may include one or more electron transport materials selected from benzimidazole derivatives, oxadiazole derivatives, quinoxaline derivatives, or other electron transport materials, which is not specially limited by the present application. For example, in one embodiment of the present disclosure, the electron transport layer 340 may be composed of DBimiBphen and LiQ.

Optionally, the cathode 200 includes a cathode material, which is a material having a small work function that facilitates electron injection into the functional layer. Specific examples of the cathode material include metals such as magnesium, calcium, sodium, potassium, titanium, indium, yttrium, lithium, gadolinium, aluminum, silver, tin, and lead or alloys thereof; or multilayer materials such as LiF/Al, Liq/Al, $LiO_2$/Al, LiF/Ca, LiF/Al, and $BaF_2$/Ca, but are not limited thereto. A metal electrode containing aluminium is preferably included as a cathode.

Optionally, as shown in FIG. 1, a hole injection layer 310 may also be arranged between the anode 100 and the first hole transport layer 321 to enhance the ability to inject holes into the first hole transport layer 321. The hole injection layer 310 may adopt a benzidine derivative, a starburst arylamine compound, a phthalocyanine derivative, or other materials, which is not specially limited by the present application. In one embodiment of the present disclosure, the hole injection layer 310 may consist of m-MTDATA.

Optionally, as shown in FIG. 1, an electron injection layer 350 may also be disposed between the cathode 200 and the electron transport layer 340 to enhance the ability to inject electrons into the electron transport layer 340. The electron injection layer 350 may include an inorganic material such as an alkali metal sulfide and an alkali metal halide, or may include a complex of an alkali metal and an organic material. In one embodiment of the present disclosure, the electron injection layer 350 may include LiQ.

Figure 3:
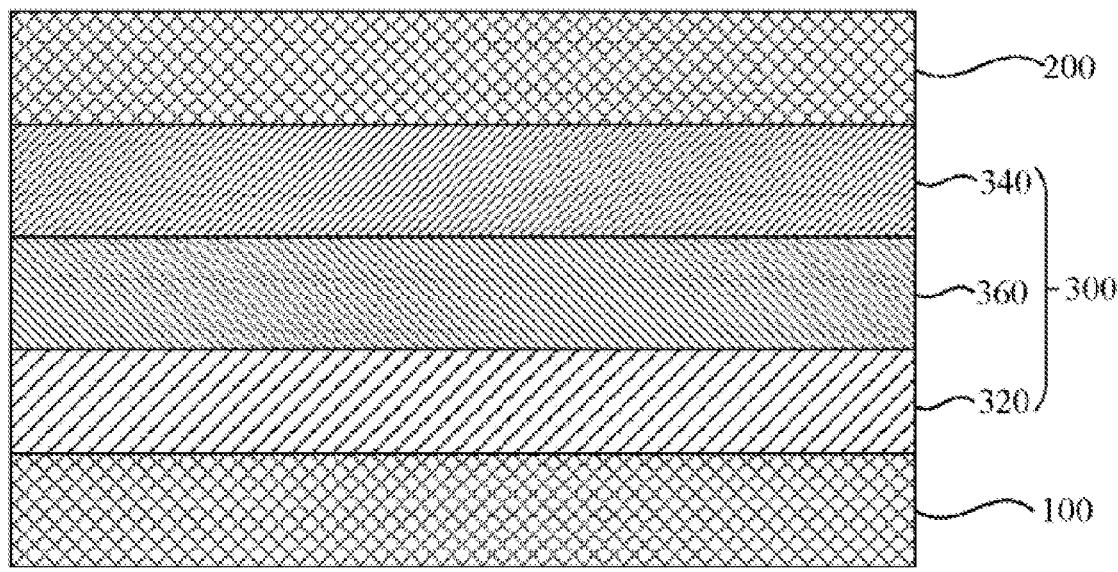
FIG. 3 is a structural schematic diagram of a photoelectric conversion device according to the embodiments of the present application.

As another example, the electronic element may be a photoelectric conversion device. As shown in FIG. 3, the photoelectric conversion device may include an anode 100 and a cathode 200 which are oppositely disposed, and a functional layer 300 disposed between the anode 100 and the cathode 200; and the functional layer 300 contains the nitrogen-containing compound provided by the present application.

Optionally, the nitrogen-containing compound provided by the present application may be used to form at least one organic film layer in the functional layer 300 to improve the performance of the photoelectric conversion device, and in particular to improve the lifetime of the photoelectric conversion device, increase the open circuit voltage of the photoelectric conversion device, or improve the uniform stability of the performance of the mass-produced photoelectric conversion device.

Optionally, the functional layer 300 includes a hole transport layer 320 containing the nitrogen-containing compound of the present application. The hole transport layer 320 may be composed of the nitrogen-containing compound provided by the present application, or may consist of the nitrogen-containing compound provided by the present application and other materials.

Optionally, the hole transport layer 320 may further include an inorganic doping material to improve the hole transport properties of the hole transport layer 320.

Optionally, as shown in FIG. 3, the photoelectric conversion device may include an anode 100, a hole transport layer 320, a photoelectric conversion layer 360 as an energy conversion layer, an electron transport layer 340, and a cathode 200 which are stacked in sequence.

Optionally, the photoelectric conversion device may be a solar cell, in particular may be an organic thin film solar cell. For example, In one embodiment of the present disclosure, the solar cell may include an anode 100, a hole transport layer 320, a photoelectric conversion layer 360, an electron transport layer 340, and a cathode 200 which are stacked in sequence, where the hole transport layer 320 contains the nitrogen-containing compound of the present application.

Embodiments of the present application also provide an electronic device, including any one of the electronic elements described in the embodiments of the electronic component described above. As the electronic device has any one of the electronic elements described in the embodiments of the electronic element described above, this electronic device has the same beneficial effect and is not repeated here.

Figure 2:
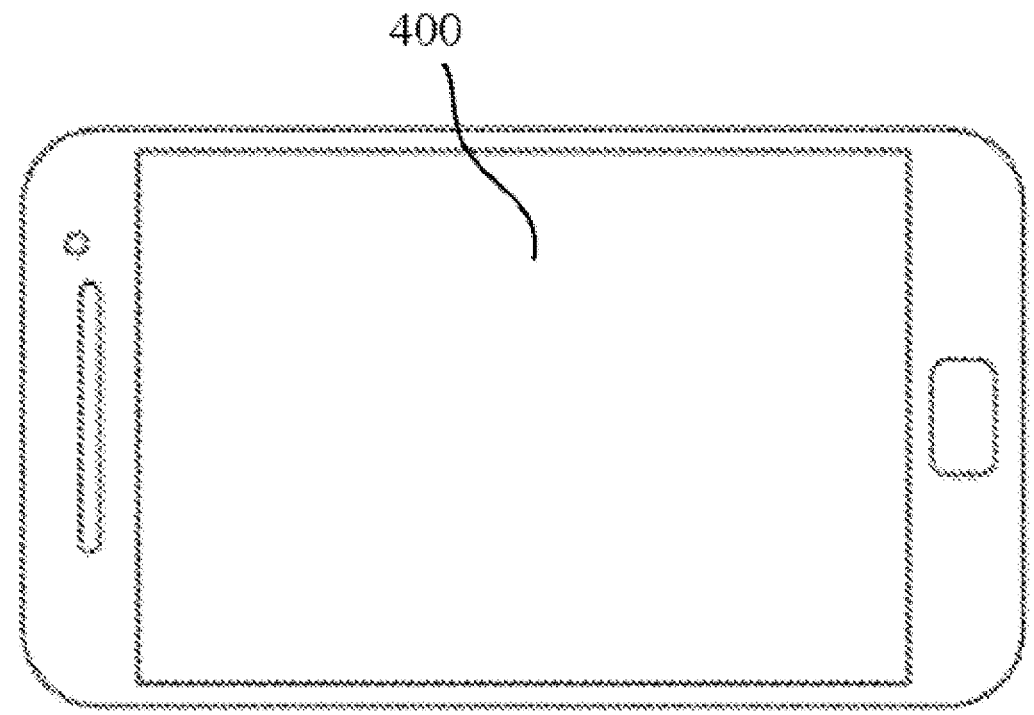
FIG. 2 is a structural schematic diagram of an electronic device according to the embodiments of the present application.

For example, as shown in FIG. 2, the present application provides a first electronic device 400 including any one of the organic electroluminescent devices described in the embodiments of the organic electroluminescent device described above. The first electronic device 400 may be a display device, a lighting device, an optical communication device, or other types of electronic devices and may include, for example, but is not limited to, a computer screen, a mobile phone screen, a television, electronic paper, an emergency lighting lamp, a light module, and the like. Since the first electronic device 400 has any one of the organic electroluminescent devices described in the embodiments of the organic electroluminescent device described above, the first electronic device 400 has the same beneficial effects, and is not repeated herein.

Figure 4:
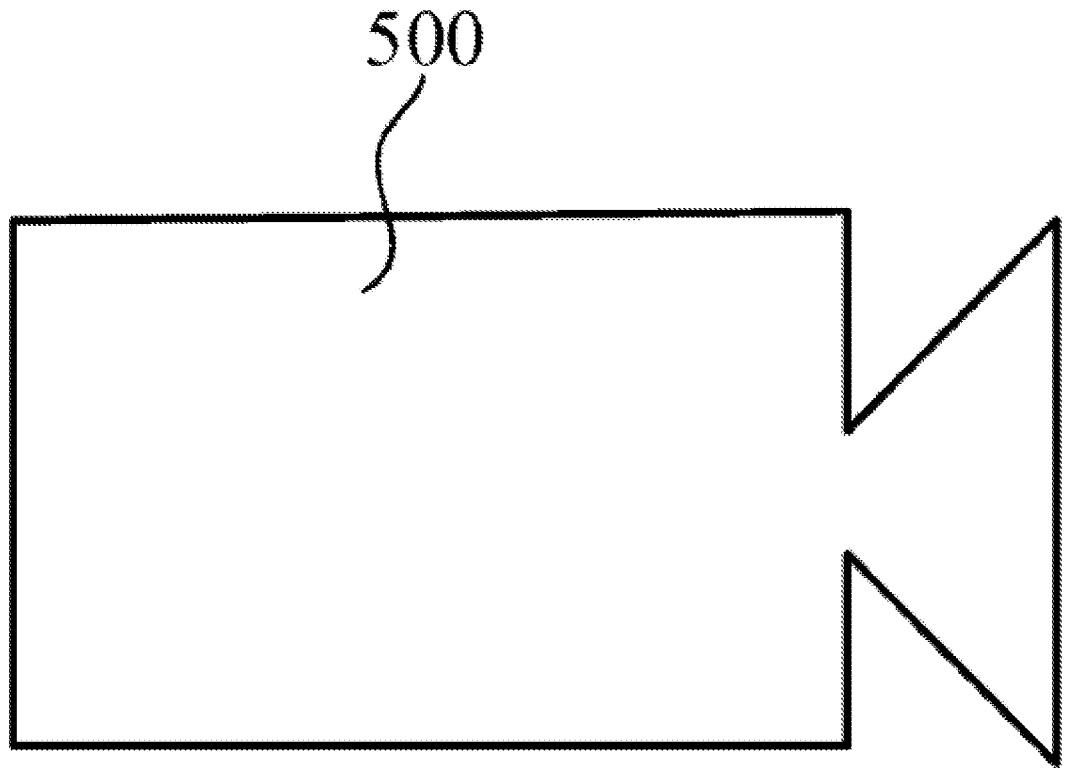
FIG. 4 is a structural schematic diagram of an electronic device according to the embodiments of the present application.

As another example, as shown in FIG. 4, the present application provides a second electronic device 500 including any one of the photoelectric conversion devices described in the embodiments of the photoelectric conversion device described above. The second electronic device 500 may be solar power generation device, a light detector, a fingerprint recognition device, an optical module, a CCD camera, or other types of electronic devices. As the second electronic device 500 has any one of the photoelectric conversion devices described in the embodiments of the photoelectric conversion device described above, the second electronic device 500 has the same beneficial effects, and is not repeated herein.

The present application will be described in further detail below by way of embodiments. However, the following embodiments are merely illustrative of the present application and are not intended to limit the present application.

Embodiments of Compound Synthesis

Synthesis of Intermediate A

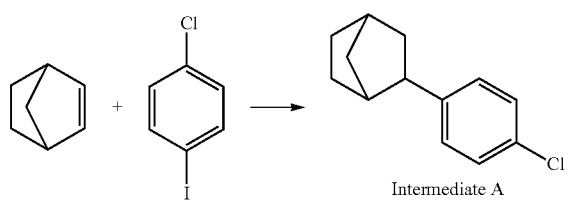 [SMILES: C1=CC2CCC1C2 ; Clc1ccc(I)cc1 ; Clc1ccc(C2CC3CCC2C3)cc1]

Intermediate A 0.95 g (10 mmol) of norbornene, 2.41 g (10 mmol) of 4-chloroiodobenzene, 0.23 g (1 mmol) of palladium acetate, and 10 mL of acetonitrile were added into a 50 mL flask, replaced the air in the flask with nitrogen, the reaction solution was stirred at room temperature (20° C.) for 10 min, then 4.8 mL of piperidine and 2 mL of formic acid were added, the reaction solution was stirred at 80° C. for 24 h, the resulting reaction solution was cooled to room temperature, the reaction was quenched by 50 mL of water, and the reaction solution was subjected to extraction with 50 mL of diethyl ether for three times, the resulting organic layer was dried over 4 g of magnesium sulfate, the magnesium sulfate was removed by filtration, the solvent was evaporated from the organic phase to obtain a crude product, the crude product was re-dissolved with 6 mL of dichloromethane and purified by column chromatography with the addition of 15 mL of n-heptane to finally obtain 1.04 g of intermediate A, with a yield of 50%. The structure of the resulting compound was confirmed by LC-MS. Mass spectrum: m/z=207.09 [M+H]$^+$.

Synthesis of Intermediate B

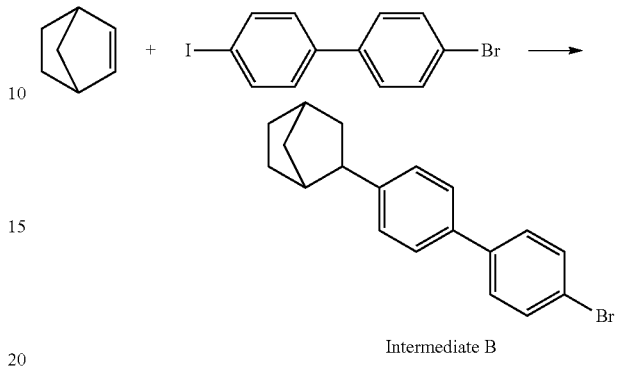

Intermediate B 1.41 g (15 mmol) of norbornene, 5.37 g (15 mmol) of 4-bromo-4'-iodobiphenyl, 0.34 g (0.15 mmol) of palladium acetate and 15 mL of dimethylsulfoxide were added into a 50 mL flask, replaced the air in the flask with nitrogen, the reaction solution was stirred at room temperature (20° C.) for 10 min, 12.3 mL of piperidine and 5 mL of formic acid were added, the reaction solution was stirred at 80° C. for 24 h, the resulting reaction solution was cooled to room temperature, the reaction was quenched by 80 mL of water, the reaction solution was subjected to extraction with 80 mL of diethyl ether for three times, the resulting organic layer was dried over 4 g of magnesium sulfate, the magnesium sulfate was removed by filtration, the solvent was evaporated from the organic phase to obtain a crude product, the crude product was re-dissolved with 5 mL of ethyl acetate and purified by column chromatography with addition of 20 mL of n-heptane to finally obtain 1.8 g of intermediate B, with a yield of 37%. The structure of the resulting compound was confirmed by LC-MS. Mass spectrum: m/z=327.07 [M+H]$^+$.

Synthesis of Compound 1

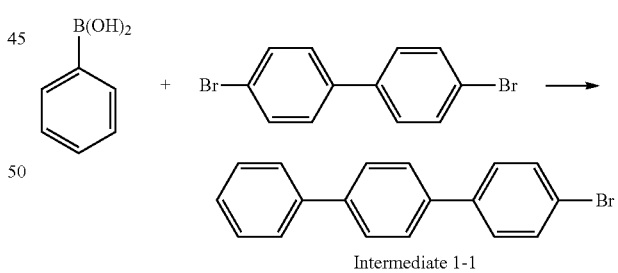

Intermediate 1-1

1.83 g (15 mmol) of phenylboronic acid, 4.78 g (15.3 mmol) of 4,4'-dibromobiphenyl, 0.35 g (0.3 mmol) of tetrakis(triphenylphosphine)palladium, 0.10 g (0.3 mmol) of tetrabutylammonium bromide, 4.15 g (30 mmol) of potassium carbonate, and a mixed solvent of 15 mL toluene/4 mL ethanol/4 mL water were added into a 50 mL flask, the reaction system was stirred and heated to 75° C. under a nitrogen atmosphere, and refluxed for 12 h, the reaction solution was cooled to room temperature, washed by 50 mL of water and subjected to extraction with 50 mL of ethyl acetate for three times, the resulting organic layer was dried over 4 g of magnesium sulfate, the solvent was evaporated by low vacuum, the obtained crude product was re-dissolved with 4 mL of dichloromethane, and purified by silica gel column chromatography (n-heptane as an eluent) to obtain 2.71 of intermediate 1-1, with a yield of 58%.

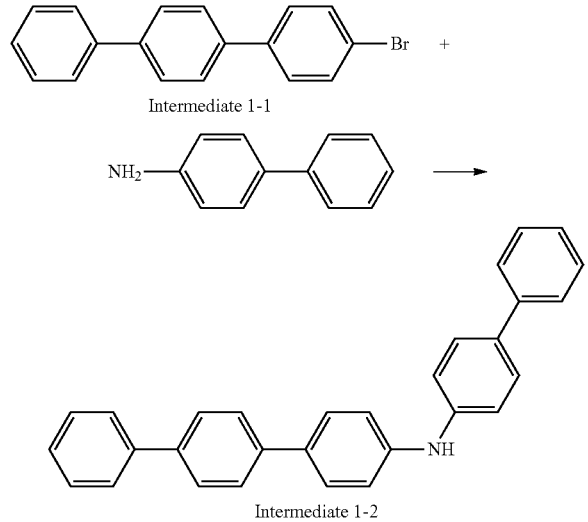

Intermediate 1-1

Intermediate 1-2

3.10 g (10 mmol) of the intermediate 1-1, 1.73 g (10.2 mmol) of 4-aminobiphenyl, 0.18 g (0.2 mmol) of tris(dibenzylideneacetone)dipalladium, 0.08 g (0.2 mmol) of 2-dicyclohexylphosphino-2',6'-dimethoxybiphenyl, 1.93 g (20 mmol) of sodium tert-butoxide and 30 mL of toluene were added into a 100 mL flask, nitrogen was introduced to the reaction system, the reaction system was heated to 110° C. and refluxed reaction for 6 h, the reaction solution was cooled to room temperature, the reaction was quenched with 60 mL of water, the reaction solution was subjected to extraction with 60 mL of ethyl acetate for three times, the obtained organic phase was dried over 4 g of magnesium sulfate, the solvent was evaporated by low vacuum, and the product was purified by recrystallization with a mixed solvent of dichloromethane and n-heptane to obtain 2.62 g of intermediate 1-2, with a yield of 65%.

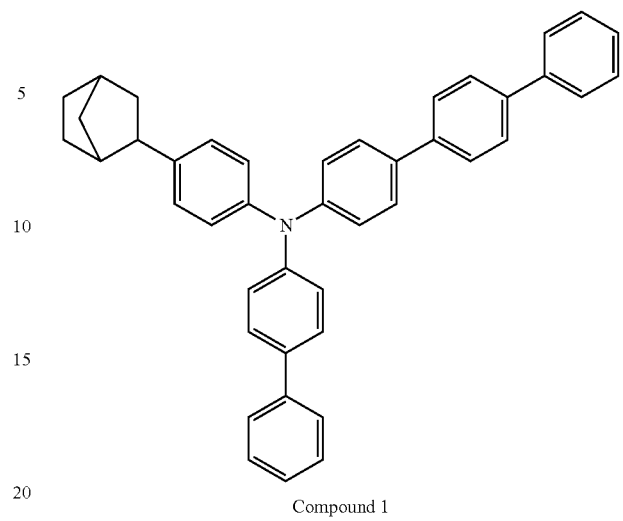

Compound 1

3.98 g (10 mmol) of the intermediate 1-2, 2.07 g (10 mmol) of the intermediate A, 0.18 g (0.2 mmol) of tris (dibenzylideneacetone)dipalladium, 0.08 g (0.2 mmol) of 2-dicyclohexylphosphino-2',6'-dimethoxybiphenyl, 1.93 g (20 mmol) of sodium tert-butoxide and 20 mL of toluene were added into a 50 mL flask, the reaction solution was heated to 110° C. under a nitrogen atmosphere and refluxed reaction for 24 h, the reaction solution was cooled to room temperature, the reaction was quenched with 60 mL of water, the reaction solution was subjected to extraction with 60 mL of ethyl acetate for three times, the resulting organic phase was dried over 4 g of magnesium sulfate, the solvent was evaporated by low vacuum, the product was dissolved in 8 mL of dichloromethane and separated and purified by silica gel column chromatography (a mixed solvent with a ratio of dichloromethane to n-heptane being 1:4 as an eluent) to obtain the compound 1 (2.5 g, with a yield of 44%). The structure of the resulting compound was confirmed by LC-MS. Mass spectrum: m/z=568.29 [M+H]$^+$.

Nuclear magnetic resonance data of the compound 1: $^1$HNMR (400 MHz, CDCl$_3$) 7.69-7.59 (m, 8H), 7.51-7.32 (m, 10H), 7.12-7.09 (m, 2H), 6.93-6.87 (m, 6H), 2.98 (m, 1H), 2.18 (m, 2H), 1.77-1.52 (m, 6H), 1.38-1.19 (m, 2H) ppm.

Synthesis of Compound 2

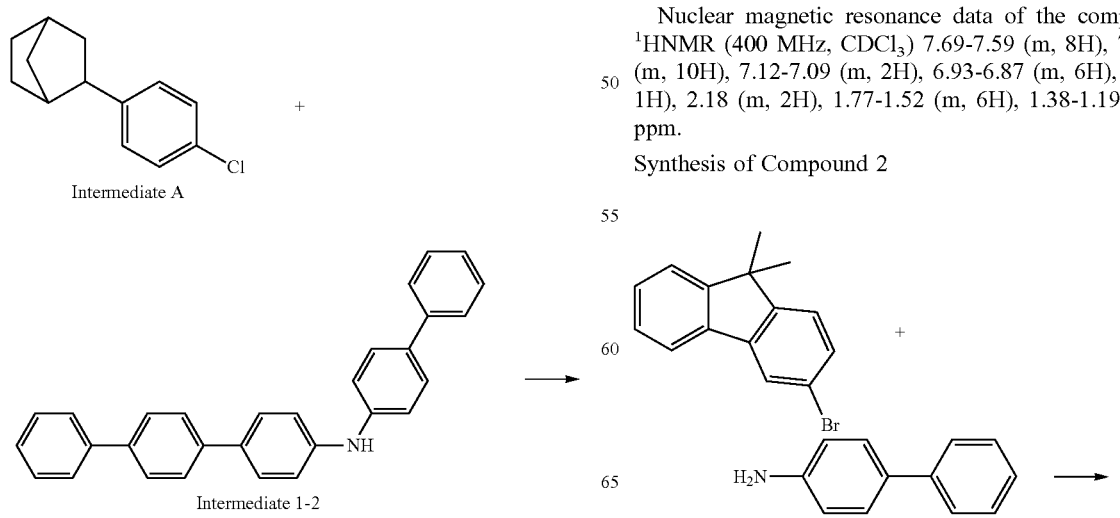

Intermediate 1-2

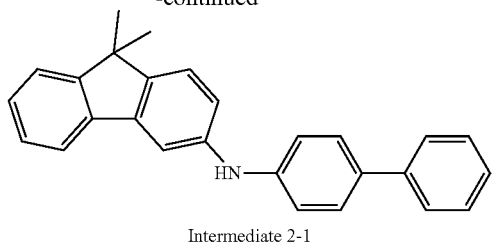

Intermediate 2-1

2.73 g (10 mmol) of 3-bromo-9,9'-dimethylfluorene, 1.69 g (10 mmol) of 4-aminobiphenyl, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 30 mL of toluene were added into a 100 mL flask, the reaction solution was heated to a reflux temperature (110° C.) under the protection of a nitrogen atmosphere for a reaction 10 h, the reaction system was cooled to room temperature, the reaction was quenched by addition of 30 mL of water to the reaction flask, the reaction solution was subjected to extraction with 50 mL of ethyl acetate for three times, the organic phase was dried over 4 g of magnesium sulfate, after filtration, the solvent was evaporated, and the crude product was recrystallized twice with toluene to obtain 2.81 g of intermediate 2-1, with a yield of 78%.

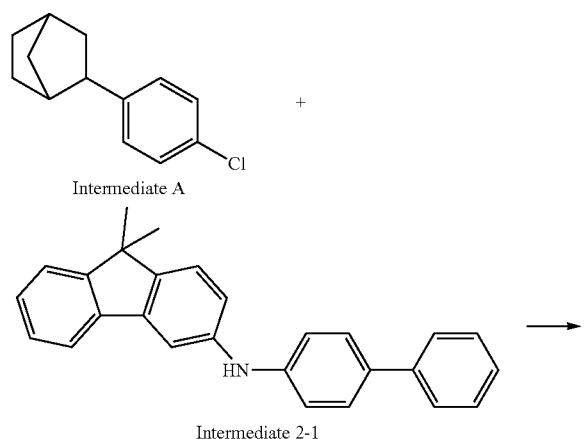

Intermediate A

Intermediate 2-1

Compound 2

3.62 g (10 mmol) of the intermediate 2-1, 2.07 g (10 mmol) of the intermediate A, 0.18 g (0.2 mmol) of tris (dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 20 mL of toluene were added into a 50 mL flask, the reaction solution was heated to 110° C. under a nitrogen atmosphere and refluxed reaction for 16 h, the reaction solution was cooled to room temperature, and subjected to extraction for three times by adding 50 mL of water and 50 mL of toluene thereto, the organic phase was dried over 6 g of magnesium sulfate, the organic phase was allowed to pass through a silica gel column, the solvent was evaporated from the solution passing through the column under low vacuum, and the crude product was recrystallized for three times with toluene to obtain the compound 2 (2.02 g, with a yield of 38%). The structure of the resulting compound was confirmed by LC-MS. Mass spectrum: m/z=532.29 [M+H]$^+$.

Nuclear magnetic resonance data of the compound 2: $^1$HNMR (400 MHz, CDCl$_3$) 7.76 (d, 1H), 7.63 (d, 2H), 7.51-7.34 (m, 7H), 7.15-7.09 (m, 2H), 7.02-6.98 (m, 2H), 6.94-6.89 (m, 4H), 6.83 (d, 2H), 2.98 (m, 1H), 2.18 (m, 2H), 1.77-1.52 (m, 12H), 1.38-1.19 (m, 2H) ppm.

Synthesis of Compound 3

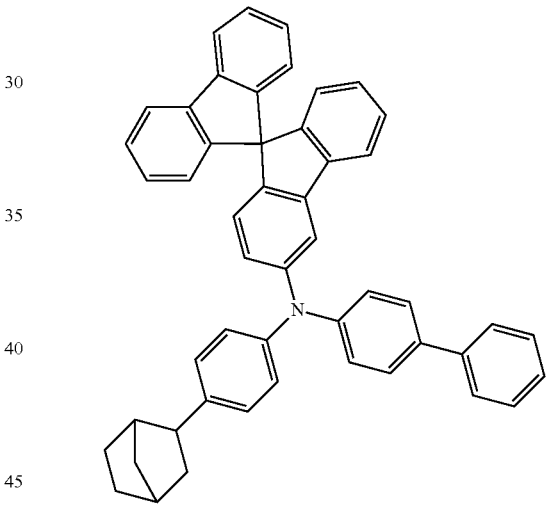

Compound 3

Referring to the synthesis method of the compound 2,3-bromo-9,9'-dimethylfluorene was replaced with 3-bromo-9,9'-spirobifluorene, so that the compound 3 (2.17 g, with a yield of 33%) was synthesized, and the structure of the resulting compound was confirmed by LC-MS. Mass spectrum: m/z=654.31 [M+H]$^+$.

Synthesis of Compound 4

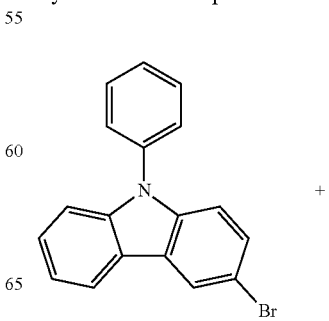

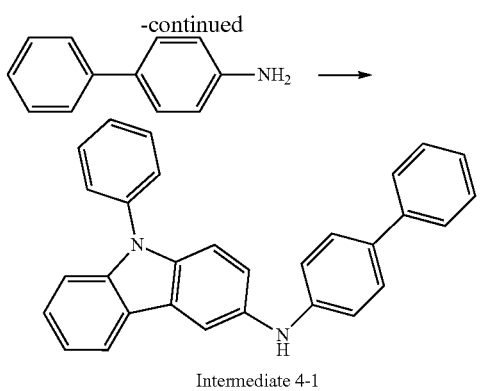

Intermediate 4-1

3.22 g (10 mmol) of 3-bromo-9-phenylcarbazole, 1.69 g (10 mmol) of 4-aminobiphenyl, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 30 mL of toluene were added into a 100 mL flask, under the protection of nitrogen gas, the reaction solution was heated to a reflux temperature for a reaction for 4 h, the reaction solution was cooled to room temperature, the reaction was quenched by 30 mL of water, the reaction solution was subjected to extraction with 50 mL of toluene for three times, the organic phase was dried over 4 g of magnesium sulfate, the solvent was evaporated under low vacuum and the product was purified by column chromatography with a mixed solution of toluene and n-heptane as an eluent to obtain 3.3 g of intermediate 4-1, with a yield of 80%.

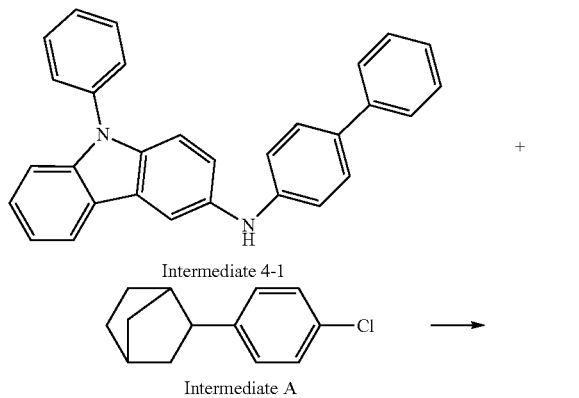

Compound 4

4.10 g (10 mmol) of the intermediate 4-1, 2.06 g (10 mmol) of the intermediate A, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 40 mL of toluene were added into a 100 mL flask, under the protection of nitrogen gas, the reaction solution was heated to reflux for 16 h, the reaction solution was cooled to room temperature, the reaction was quenched with 50 mL of water, the reaction solution was subjected to extraction with 50 mL of toluene for three times, the organic phase was dried over 8 g of magnesium sulfate, the organic phase was allowed to pass through a short silica gel column, the solvent was evaporated from the solution passing through the column under low vacuum, and the crude product was recrystallized with toluene for two times to obtain the compound 4 (2.3 g, with a yield of 40%). The structure of the resulting compound was confirmed by LC-MS. Mass spectrum: m/z=581.29 [M+H]⁺.

Synthesis of Compound 5

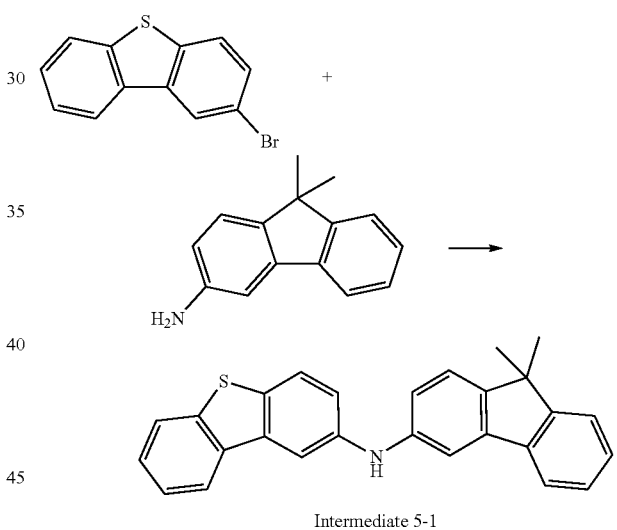

Intermediate 5-1

2.63 g (10 mmol) of 2-bromodibenzothiophene, 2.09 g (10 mmol) of 3-amino-9,9'-dimethylfluorene, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 30 mL of toluene were added into a 50 mL flask, the reaction solution was heated to reflux under a nitrogen atmosphere, the reaction was complete after 10 h, the reaction solution was cooled to room temperature, the reaction was quenched by addition of 50 mL of water, the reaction solution was subjected to extraction with 50 mL of ethyl acetate for three times, and the organic phase was allowed to pass through a column (dichloromethane and n-heptane in a ratio of 1:5 as an eluent) to obtain 1.93 g of intermediate 5-1, with a yield of 49%.

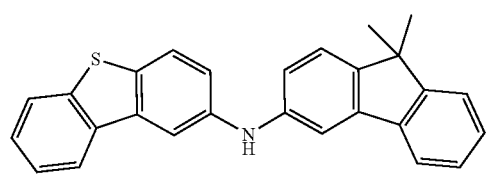

Intermediate 5-1

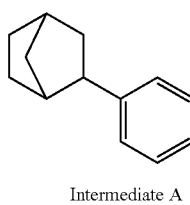

Intermediate A

→

Synthesis of Compound 6

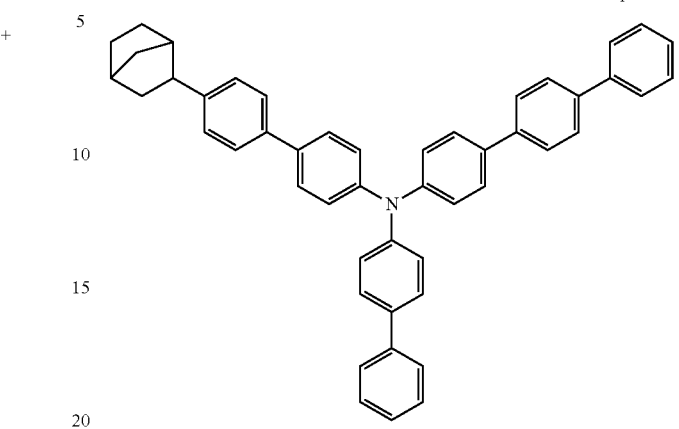

Compound 6

Referring to the synthesis method of the compound 1, the intermediate A was replaced with the intermediate B, so that the compound 6 (2.56 g) was synthesized with a yield of 40%. The structure of the resulting compound was confirmed by LC-MS. Mass spectrum: m/z=644.32 [M+H]$^+$.

Synthesis of Compound 7

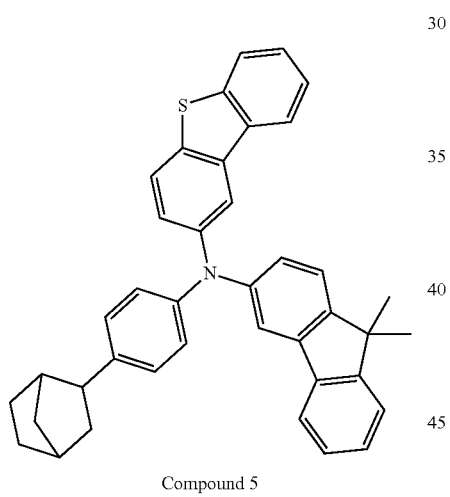

Compound 5

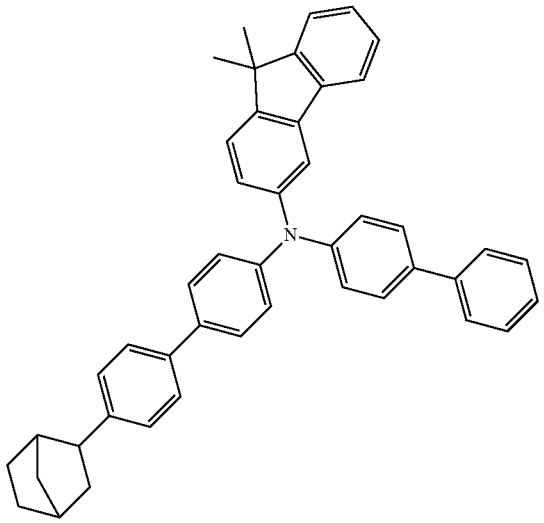

Compound 7

3.92 g (10 mmol) of the intermediate 5-1, 2.07 g (10 mmol) of the intermediate A, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 40 mL of toluene were added into a 100 mL flask, under the protection of nitrogen gas, the reaction solution was heated to a reflux temperature for a reaction for 24 h, the reaction solution was cooled to room temperature, the reaction was quenched with 50 mL of water, the reaction solution was subjected to extraction with 50 mL of toluene for three times, the organic phase was dried over 4 g of magnesium sulfate and allowed to pass through a column (dichloromethane and n-heptane in a ratio of 1:5 as an eluent) to obtain the compound 5 (2.64 g, with a yield of 47%). The structure of the resulting compound was confirmed by LC-MS. Mass spectrum: m/z=562.25 [M+H]$^+$.

Referring to the synthesis method of the compound 2, the intermediate A was replaced with the intermediate B, so that the compound 7 (3.06 g, with a yield of 50%) was synthesized. The structure of the resulting compound was confirmed by LC-MS. Mass spectrum: m/z=608.32 [M+H]+.

Synthesis of Compound 8

Compound 8

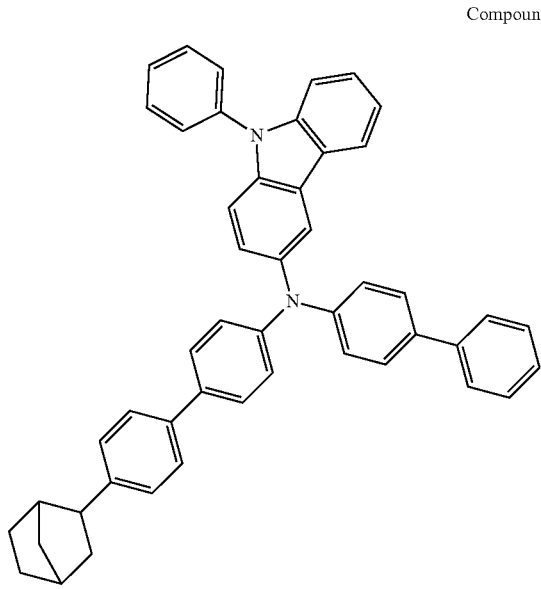

Referring to the synthesis method of the compound 4, the intermediate A was replaced with the intermediate B, so that the compound 8 (2.41 g, with a yield of 37%) was synthesized. The structure of the resulting compound was confirmed by LC-MS. M/z=657.32 [M+H]$^+$.

Synthesis of Compound 9

Compound 9

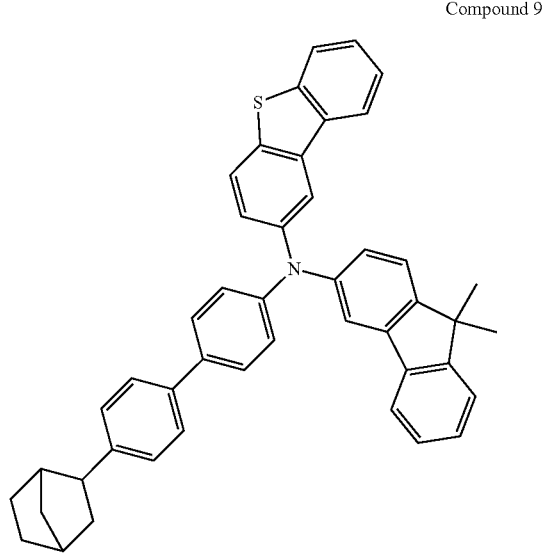 [SMILES: CC1(C)c2ccccc2-c2cc(N(c3ccc(-c4ccc(C5CC6CCC5C6)cc4)cc3)c3ccc4sc5ccccc5c4c3)ccc21]

Referring to the synthesis method of the compound 5, the intermediate A was replaced with the intermediate B, so that the compound 9 (2.94 g, with a yield of 46%) was synthesized. The structure of the resulting compound was confirmed by LC-MS and $^1$H NMR. Mass spectrum: m/z=638.28 [M+H]$^+$.

Synthesis of Compound 10

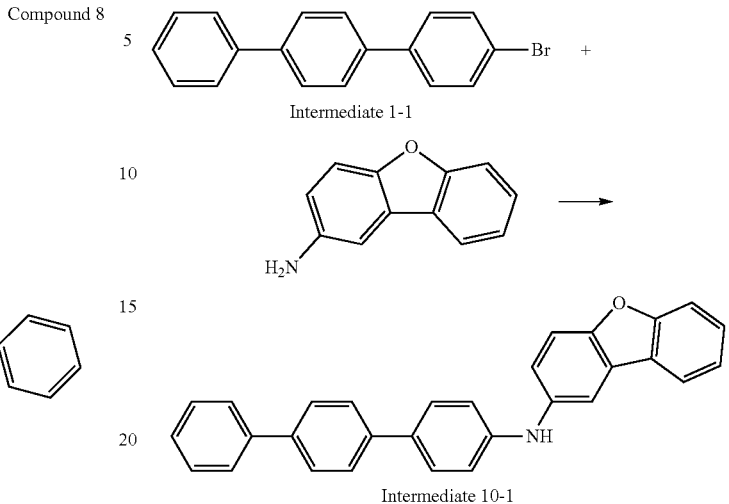

Intermediate 10-1

3.1 g (10 mmol) of the intermediate 1-1, 1.84 g (10 mmol) of 2-aminodibenzofuran, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 30 mL of toluene were added into a 50 mL flask, under the protection of nitrogen gas, the reaction solution was heated to a reflux temperature for a reaction for 4 h, the reaction solution was cooled to room temperature, the reaction was quenched by 50 mL of water, the reaction solution was subjected to extraction with 50 mL of ethyl acetate for three times, the organic phase was dried over 4 g of magnesium sulfate and the product was separated and purified by column chromatography (dichloromethane and n-heptane in a ratio of 1:3 as an eluent) to obtain 2.6 g of intermediate 10-1, with a yield of 63%.

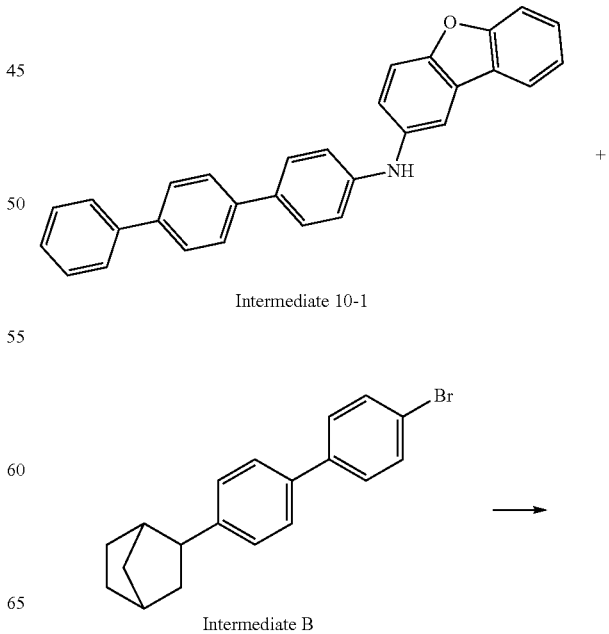

Intermediate 10-1

Intermediate B

-continued

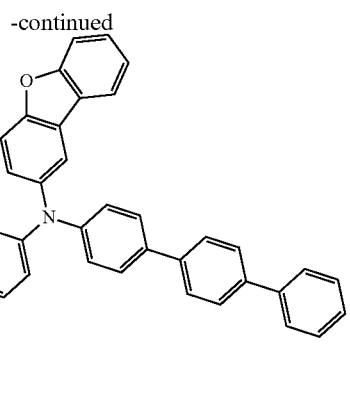

Compound 10

4.12 g (10 mmol) of the intermediate 10-1, 3.28 g (10 mmol) of the intermediate B, 0.18 g (0.2 mmol) of tris(dibenzylideneacetone)dipalladium, 0.08 g (0.2 mmol) of 2-dicyclohexylphosphino-2',6'-dimethoxybiphenyl, 1.92 g (20 mmol) of sodium tert-butoxide and 40 mL of toluene were added into a 100 mL flask, nitrogen was introduced as a protective gas, the reaction system was heated to reflux for 24 h, the reaction was cooled to room temperature, the reaction was quenched by 50 mL of water, the reaction solution was subjected to extraction with 50 mL of toluene for three times, the organic phase was dried over 4 g of magnesium sulfate, the organic phase was allowed to pass through a short silica gel column, the solvent was evaporated from the resulting eluate under low vacuum and the product was recrystallized with dichloromethane to obtain the compound 10 (2.28 g, with a yield of 35%). The structure of the resulting compound was confirmed by LC-MS. Mass spectrum: m/z=658.30 [M+H]+.

Examples of Preparation and Evaluation of the Organic Electroluminescent Devices Preparation of Blue Organic Electroluminescent Device Example 1

An anode was prepared by the following process: an ITO substrate (manufactured by Corning) with an ITO thickness of 1500 Å was cut into a dimension of 40 mm (length)*40 mm (width)*0.7 mm (thickness), and prepared into an experimental substrate with a cathode overlap region, an anode and an insulation layer pattern by using a photolithography process, and surface treatment was performed with UV ozone and $O_2:N_2$ plasma to increase the work function of the anode (the experimental substrate) and to remove scum.

m-MTDATA (4,4',4''-tris(N-3-methylphenyl-N-phenylamino)triphenylamine) was vacuum-evaporated on the experimental substrate (the anode) to form a hole injection layer (HIL) having a thickness of 100 Å, and the compound 1 was vacuum-evaporated on the hole injection layer to form a first hole transport layer (HTL1) having a thickness of 800 Å.

TCTA (4,4',4''-tris(carbazol-9-yl)triphenylamine) was evaporated on the first hole transport layer to form a second hole transport layer (HTL2) having a thickness of 300 Å.

α,β-ADN was used as a host material, while BD-1 was doped, and an organic electroluminescent layer (EML) having a thickness of 220 Å was formed by the host material and the dopant at a film thickness ratio of 30:3.

DbimiBphene (4,7-diphenyl-2,9-bis(4-(1-phenyl-1H-benzo[d]imidazol-2-yl)phenyl)-1,10-phenanthraline) and LiQ (8-hydroxyquinoline-lithium) were mixed at a weight ratio of 1:1 and evaporated to form an electron transport layer (ETL) having a thickness of 300 Å, LiQ was evaporated on the electron transport layer to form an electron injection layer (EIL) having a thickness of 10 Å, and then magnesium (Mg) and silver (Ag) were mixed at an evaporation rate of 1:9 and vacuum-evaporated on the electron injection layer to form a cathode having a thickness of 120 Å.

CP-1 having a thickness of 650 Å was evaporated on the above-described cathode to form an organic capping layer (CPL), thereby completing the manufacturing of the organic electroluminescent device.

Where, the structural formulas of m-MTDATA, TCTA, α,β-ADN, BD-1, DBimiBphen, and LiQ are as follows:

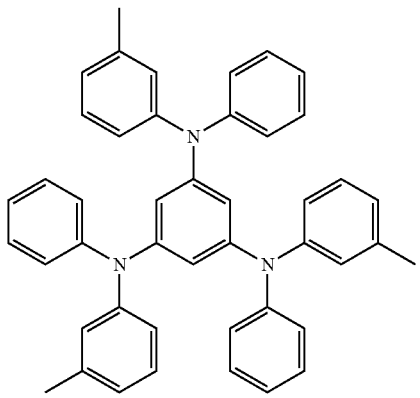

m-MTDATA

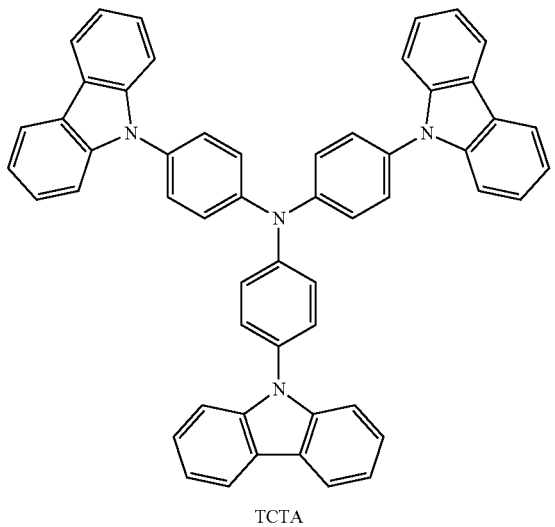

TCTA

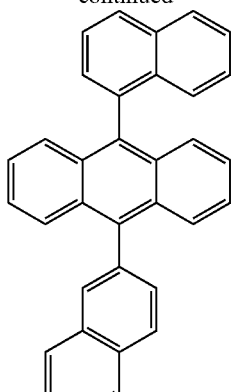

α,β-ADN

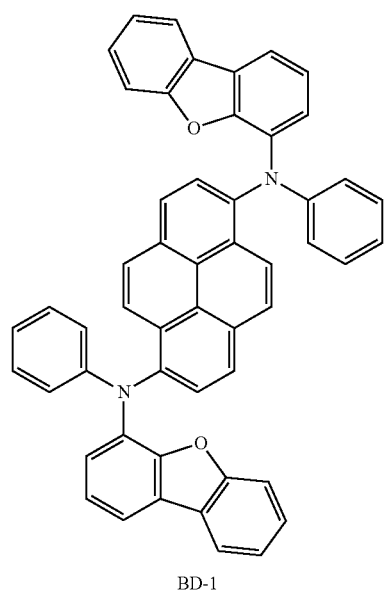

BD-1

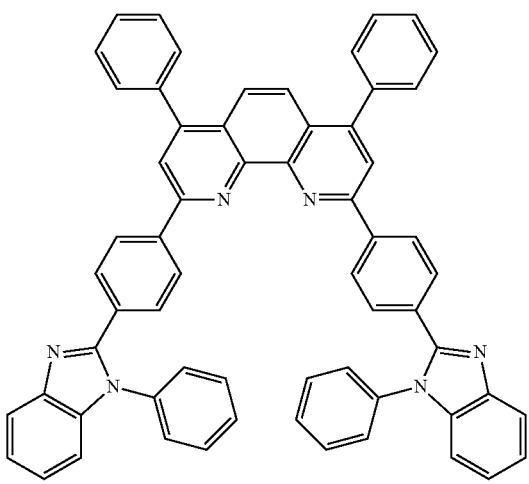

DBimiBphen

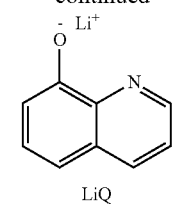

LiQ

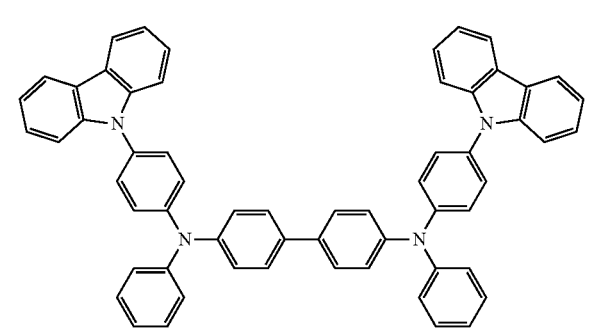

CP-1

Examples 2-5

An organic electroluminescent device was manufactured by the same method as in Example 1 except that the compounds shown in Table 1 were each used when the first hole transport layer (HTL1) was formed.

Namely, Example 2 adopted the compound 2 to manufacture an organic electroluminescent device, Example 3 adopted the compound 3 to manufacture an organic electroluminescent device, Example 4 adopted the compound 4 to manufacture an organic electroluminescent device, and Example 5 adopted the compound 5 to manufacture an organic electroluminescent device, and the performance of the organic electroluminescent device is shown in Table 1.

Comparative Examples 1-3

In the Comparative Examples 1-3, an organic electroluminescent device was manufactured by the same method as in Example 1 except that NPB (N,N'-diphenyl-N,N'-(1-naphthyl)-1,1'-biphenyl-4,4'-diamine), the compound A (with a structure shown below), and the compound B (with a structure shown below) were used as the first hole transport layer instead of the compound 1.

Namely, Comparative Example 1 adopted NPB to manufacture an organic electroluminescent device, Comparative Example 2 adopted the compound A to manufacture an organic electroluminescent device, and Comparative Example 3 adopted the compound B to manufacture an organic electroluminescent device, and the device performance is shown in Table 1.

Where, the structures of the NPB, compound A, and compound B are as follows:

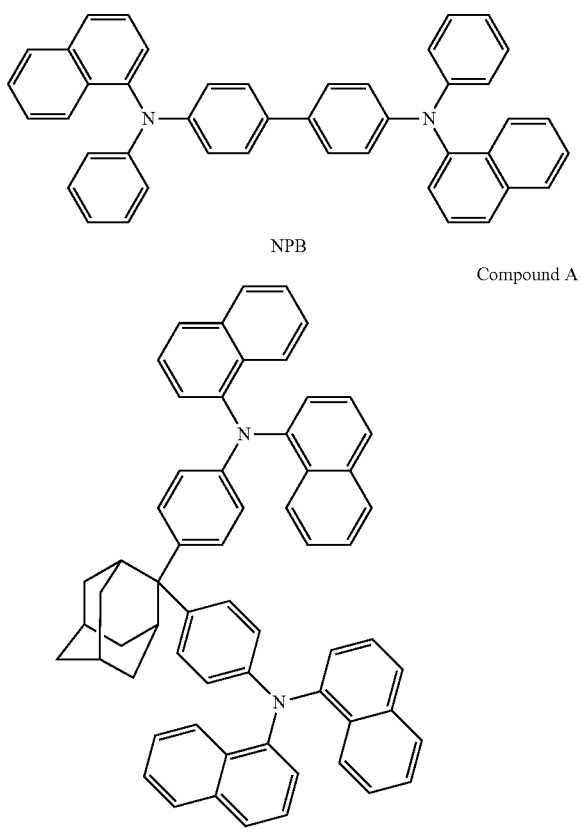

NPB

Compound A

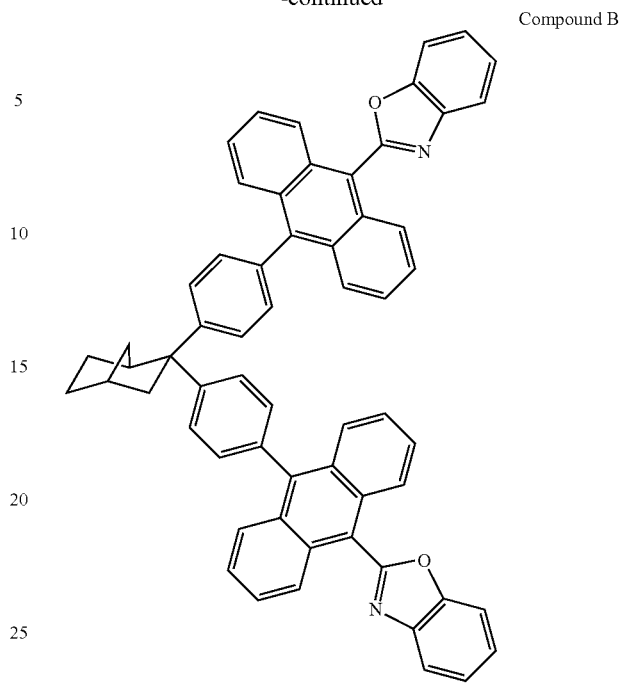

Compound B

The performance of the organic electroluminescent devices prepared in Examples 1-5 and Comparative Examples 1-3 were tested, and the test results were shown in Table 1:

TABLE 1

Performance of Organic electroluminescent device of Examples 1-5 and Comparative Examples 1-3

| Example | First hole transport layer | Operating voltage Volt (V) | Luminous efficiency (Cd/A) | External quantum efficiency EQE (%) | T95 device service life (h) | Color coordinate CIEy |
|---|---|---|---|---|---|---|
| Example 1 | Compound 1 | 3.88 | 6.4 | 12.7 | 189 | 0.049 |
| Example 2 | Compound 2 | 3.89 | 6.5 | 12.9 | 173 | 0.048 |
| Example 3 | Compound 3 | 3.93 | 6.4 | 12.7 | 165 | 0.049 |
| Example 4 | Compound 4 | 4.01 | 6.5 | 12.6 | 178 | 0.049 |
| Example 5 | Compound 5 | 4.12 | 6.4 | 12.0 | 201 | 0.048 |
| Comparative Example 1 | NPB | 4.61 | 3.6 | 9.2 | 110 | 0.048 |
| Comparative Example 2 | Compound A | 4.64 | 5.4 | 11.2 | 130 | 0.049 |
| Comparative Example 3 | Compound B | 4.70 | 5.7 | 10.8 | 128 | 0.048 |

Where, in Table 1, the operating voltage, luminous efficiency, external quantum efficiency, and color coordinate were tested at a constant current density of 10 mA/cm² and the T95 device service life was tested at a constant current density of 15 mA/cm².

As can be seen from Table 1, the organic electroluminescent devices prepared in Examples 1-5 had operating voltage decreased by 11%-26.8%, the luminous efficiency improved by at least 12.3% and the lifetime increased by at least 26.9% compared with the organic electroluminescent devices prepared in Comparative Examples 1-3.

Therefore, using the nitrogen-containing compound of the present application for the first hole transport layer of the organic electroluminescent device can significantly reduce the operating voltage of the organic electroluminescent device, improve the luminous efficiency, and improve the lifetime of the organic electroluminescent device.

Heat Treatment Examples

The organic electroluminescent devices prepared in Examples 1, 3 and 5 and Comparative Examples 1 and 2 were placed in an environment of 110° C. for 1 hour to be subjected to heat treatment, and after the organic electroluminescent devices after heat treatment were taken out, the performance of the organic electroluminescent devices after heat treatment was determined. The test results are presented in Table 2:

TABLE 2

Performance of organic electroluminescent device after heat treatment

| Example | First hole transport layer | Operating voltage Volt (V) | Luminous efficiency (Cd/A) | External quantum efficiency EQE (%) | T95 device lifetime (h) | Color coordinate CIEy |
|---|---|---|---|---|---|---|
| Example 1 | Compound 1 | 3.88 | 6.5 | 12.5 | 190 | 0.049 |
| Example 3 | Compound 3 | 3.91 | 6.4 | 12.6 | 170 | 0.049 |
| Example 5 | Compound 5 | 4.10 | 6.0 | 12.0 | 200 | 0.048 |
| Comparative Example 1 | Compound A | 4.63 | 4.4 | 9.2 | 92 | 0.049 |
| Comparative Example 2 | Compound B | 4.90 | 4.7 | 8.8 | 87 | 0.048 |

Comparing Table 1 (performance data of the organic electroluminescent device not subjected to heat treatment) with Table 2 (performance data of the organic electroluminescent device after heat treatment), it can be known that when the compounds 1, 3 and 5 of the present application are used for the first hole transport layer of the organic electroluminescent device, the voltage, the efficiency, and the lifetime of the device after heat treatment have no tendency to decrease compared with the performance of the device before heat treatment. However, when the first hole transport layer of the organic electroluminescent device adopts the compounds A and B, the performance of the device after heat treatment is changed. The efficiency and lifetime of the device adopting the compound A are significantly reduced, the voltage of the device adopting the compound B is increased by 0.2V compared with that before heat treatment, and the efficiency and lifetime of the device adopting the compound B are also significantly reduced.

Red Organic Electroluminescent Device

Example 6

An anode was prepared by the following process: an ITO substrate (manufactured by Corning) with an ITO thickness of 1500 Å was cut into a dimension of 40 mm (length)*40 mm (width)*0.7 mm (thickness), and prepared into an experimental substrate with a cathode overlap region, an anode and an insulation layer pattern by using a photolithography process, and surface treatment was performed with UV ozone and $O_2$:$N_2$ plasma to increase the work function of the anode (the experimental substrate) and to remove scum.

m-MTDATA was vacuum-evaporated on the experimental substrate (the anode) to form a hole injection layer (HIL) having a thickness of 100 Å, and NPB was evaporated on the hole injection layer to form a first hole transport layer (HTL1) having a thickness of 800 Å.

The compound 6 was vacuum-evaporated on the first hole transport layer to form a second hole transport layer (HTL2) having a thickness of 850 Å.

4,4'-N,N'-dicarbazole-biphenyl (abbreviated as "CBP") was evaporated as a host material on the second hole transport layer, while Ir(piq)$_2$(acac) was doped, and an organic electroluminescent layer (EML) having a thickness of 350 Å was formed by the host material and the dopant at a film thickness ratio of 35:5.

DBimiBphen and LiQ were mixed at a weight ratio of 1:1 and evaporated to form an electron transport layer (ETL) having a thickness of 300 Å, LiQ was evaporated on the electron transport layer to form an electron injection layer (EIL) having a thickness of 10 Å, and then magnesium (Mg) and silver (Ag) were mixed at an evaporation rate of 1:9 and vacuum-evaporated on the electron injection layer to form a cathode having a thickness of 105 Å.

CP-1 having a thickness of 650 Å was evaporated on the above-described cathode to form an organic capping layer (CPL), thereby completing the manufacturing of the organic electroluminescent device.

Where, the structural formulas of CBP and Ir(piq)$_2$(acac) are as follows:

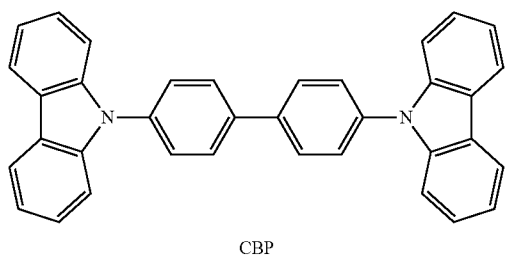

CBP

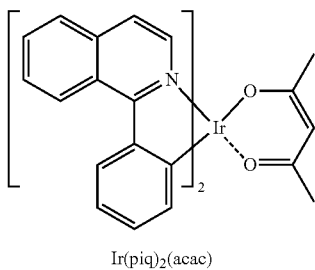

Ir(piq)₂(acac)

Examples 7-10

An organic electroluminescent device was manufactured by the same method as in Embodiment 6 except that the compounds shown in Table 3 were each used when the second hole transport layer (HTL2) was formed.

Namely, Example 7 adopted the compound 7 to manufacture an organic electroluminescent device, Example 8 adopted the compound 8 to manufacture an organic electroluminescent device, Example 9 adopted the compound 9 to manufacture an organic electroluminescent device, and Example 10 adopted the compound 10 to manufacture an organic electroluminescent device.

Comparative Examples 4-5

In the Comparative Examples 4-5, an organic electroluminescent device was manufactured by the same method as in Embodiment 6 except that the compound A and the compound B were used as the hole transport layer instead of the compound 6.

Comparative Example 6

An organic electroluminescent device was prepared by employing the same method as in Example 6 described above except that the second hole transport layer was not formed.

Namely, Comparative Example 4 adopted the compound A to manufacture an organic electroluminescent device, Comparative Example 5 adopted the compound B to manufacture an organic electroluminescent device, and Comparative Example 6 was not provided with a second hole transport layer.

TABLE 3

Performance of Organic electroluminescent device of Examples 6-10 and Comparative Examples 4-6

| Example | Second hole transport layer | Operating voltage Volt (V) | Luminous efficiency (Cd/A) | External quantum efficiency EQE (%) | T95 device lifetime (h) | Color coordinate CIEx |
|---|---|---|---|---|---|---|
| Example 6 | Compound 6 | 3.84 | 34.9 | 22.7 | 220 | 0.68 |
| Example 7 | Compound 7 | 3.79 | 34.5 | 22.3 | 218 | 0.68 |
| Example 8 | Compound 8 | 3.75 | 33.8 | 22.3 | 215 | 0.68 |
| Example 9 | Compound 9 | 3.87 | 33.9 | 23.5 | 221 | 0.68 |
| Example 10 | Compound 10 | 3.78 | 34.6 | 22.0 | 220 | 0.68 |
| Comparative Example 4 | Compound A | 4.32 | 27.2 | 19.5 | 150 | 0.68 |
| Comparative Example 5 | Compound B | 4.54 | 26.5 | 19.3 | 160 | 0.68 |
| Comparative Example 6 | — | 4.98 | 24.2 | 17.6 | 156 | 0.68 |

In Table 3, the luminous efficiency, color coordinate, operating voltage, and external quantum efficiency were tested at a constant current density of 10 mA/cm² and the T95 device service life was tested at a constant current density of 30 mA/cm².

As can be seen in Table 3, compared with those in Comparative Examples 4-6, the operating voltage was increased by 10-25%, the luminous efficiency was improved by at least 24.2%, the external quantum efficiency was improved by at least 12.8%, and the lifetime was improved by at least 34.3% in Examples 6-10.

Therefore, using the nitrogen-containing compound of the present application for the second hole transport layer of the organic electroluminescent device can significantly reduce the operating voltage of the organic electroluminescent device, improved luminous efficiency, and improved the lifetime of the organic electroluminescent device.

In summary, when the nitrogen-containing compound of the present application is used for preparing the organic electroluminescent device, the driving voltage of the electroluminescent device can be effectively reduced, the external quantum efficiency can be improved, and the lifetime of the organic electroluminescent device can be improved.

Heat Treatment Examples

The organic electroluminescent devices prepared in Example 6, Example 7, Example 10, Comparative Example 4, and Comparative Example 5 were placed at 110° C. for 1 hour to be subjected to heat treatment. The organic electroluminescent device after heat treatment was subjected to formation tests, and the test results are shown in Table 4:

TABLE 4

Performance test results of organic electroluminescent device after heat treatment

| Example | Second hole transport layer | Operating voltage Volt (V) | Luminous efficiency (Cd/A) | External quantum efficiency EQE (%) | T95 device service life (h) | Color coordinate CIEy |
|---|---|---|---|---|---|---|
| Example 6 | Compound 6 | 3.82 | 35.0 | 22.4 | 218 | 0.682 |
| Example 7 | Compound 7 | 3.80 | 34.7 | 22.1 | 220 | 0.680 |
| Example 10 | Compound 10 | 3.77 | 34.4 | 22.0 | 219 | 0.682 |
| Comparative Example 4 | Compound A | 4.32 | 20.2 | 16.5 | 100 | 0.680 |
| Comparative Example 5 | Compound B | 4.70 | 18.5 | 15.3 | 107 | 0.682 |

Comparing Table 3 (performance data of the organic electroluminescent device not subjected to heat treatment) with Table 4 (performance data of the organic electroluminescent device after heat treatment), it can be known that when the compound 6, the compound 7, the compound 10 according to the present application are used for the second hole transport layer of the organic electroluminescent device, the voltage, the efficiency, and the lifetime of the device after heat treatment have no tendency to decrease compared with the performance of the device before heat treatment. However, when the second hole transport layer of the organic electroluminescent device adopts the compounds A and B, the performance of the device after heat treatment is significantly reduced. The efficiency and lifetime of the device adopting the compound A are significantly reduced, the voltage of the device adopting the compound B is increased by 0.16V compared with that before heat treatment, and the efficiency and lifetime of the device adopting the compound B are also significantly reduced.

Thermal Stability of Compounds

When the compounds are used in mass production of devices, the compounds need to be heated under evaporation conditions for a long period of time. If the thermal stability of the molecular structures of the compounds is poor under heated conditions, the purities of the compounds decrease under heated conditions over a long period of time, resulting in large differences in the performance of devices prepared in the early, middle and late stage of actual mass production.

The present application evaluates the stability of the molecular structure of nitrogen-containing compound of the present application under heated conditions over a long period of time during mass production evaporation by the following method:

Under high vacuum environment ($<10^{-6}$ Pa), and the heat-resistant experiments (heat-holding treatments) was performed for 200 hours for each of compounds 1-10 and the compounds A, B, and C, at the temperature corresponding to an evaporation rate of 5 Å per second. The stability of the nitrogen-containing compound of the present application under mass production conditions was judged by the purity drop value before and after the heat-resistant experiments.

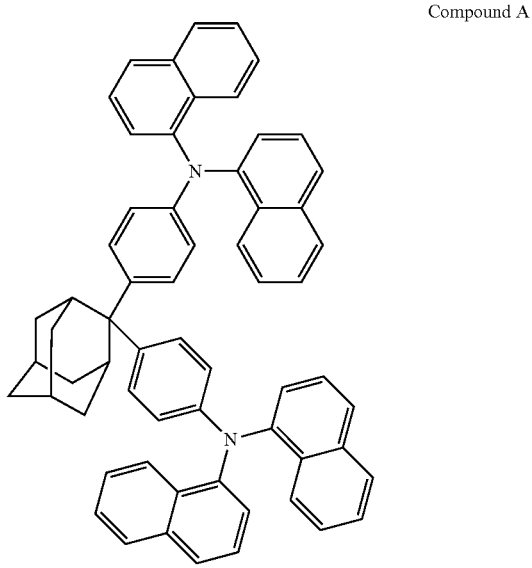

Compound A

Compound B

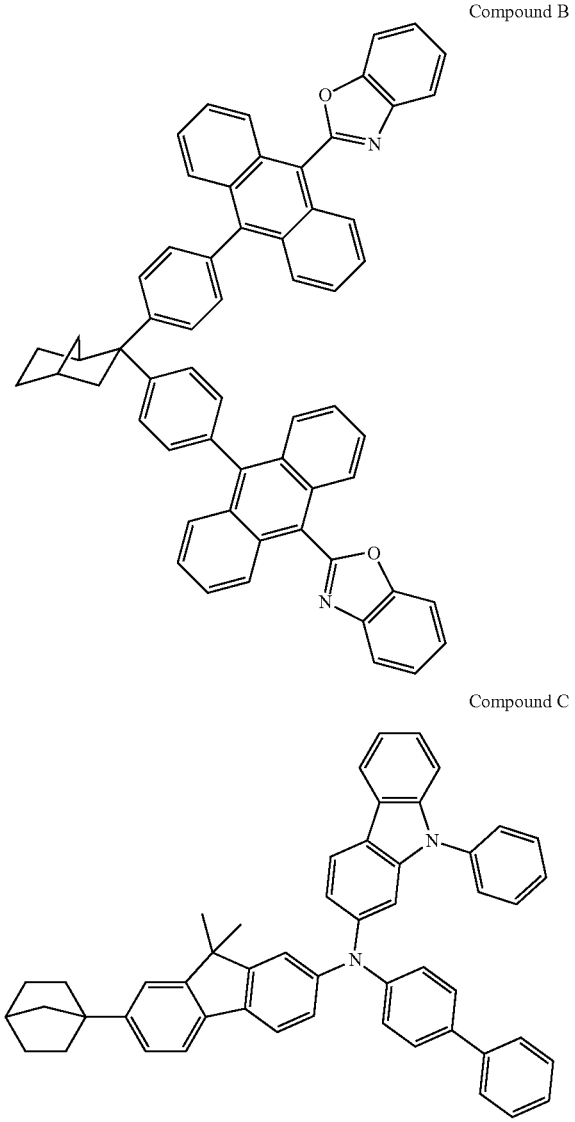

Compound C

The temperature and purity drop value results of the heat-resistant experiments of the nitrogen-containing compound are shown in Table 5:

TABLE 5

Test Temperature and Purity Drop Values of Nitrogen-Containing Compounds

| Compound | 5 Å/s evaporation temperature (° C.) | Purity Drop Value (HPLC, %) |
| --- | --- | --- |
| Compound 1 | 241 | 0.03 |
| Compound 2 | 229 | 0.05 |
| Compound 3 | 289 | 0.07 |
| Compound 4 | 252 | 0.02 |
| Compound 5 | 238 | 0.26 |
| Compound 6 | 275 | 0.39 |
| Compound 7 | 262 | 0.13 |
| Compound 8 | 288 | 0.42 |
| Compound 9 | 265 | 0.26 |
| Compound 10 | 289 | 0.29 |
| Compound A | 342 | 2.43 |
| Compound B | 360 | 3.89 |
| Compound C | 245 | 1.32 |

As can be seen from Table 5, the nitrogen-containing compounds of the present application all have purity drop values of less than 0.5%. The purity drop values were more than 1% for the compound A, compound B, and compound C. Accordingly, the thermal stability of the nitrogen-containing compounds of the present application is far superior to those of the compound A, compound B, and compound C.

When the purity drop value of the compound is more than 1%, the efficiency and lifetime of the device are significantly reduced; thus, such thermally unstable compounds can lead to large differences in the performance of devices prepared in the early, middle and late stage of actual mass production. In the present disclosure, the molecular weights of the compounds 1-10 are all small, so that the evaporation temperatures are relatively low, and the heat-resistant experiments demonstrate the purity drop values are less than 0.5%, and thus the nitrogen-containing compounds of the present application have excellent mass production thermal stability.

In the present disclosure, norbornyl is introduced between the branches of triarylamine, which can finely adjust the bonding angle and the degree of conjugation between the amine and each aryl group, thereby reducing the operating voltage of the organic electroluminescent device, improving the luminous efficiency, and improving the lifetime. The reason why the No. 2 position of norbornene is connected to the triarylamine in this application is because the No. 2 steric hindrance is small and it is easy to synthesize. Therefore, the organic electroluminescent device manufactured by using the compound of the present application has characteristics of low driving voltage, high luminous efficiency, and long lifetime.

Moreover, the nitrogen-containing compound of the present application employs norbornyl as a substituent group, is easier to synthesize than a compound using adamantyl or the like and has a lower raw material cost during synthesis, improves accessibility of a hole transport layer material, is more advantageous for large-scale application, and can alleviate the constraints on the scale of OLED and other industries due to the difficulty in preparing hole transport layer materials. More importantly, the nitrogen-containing compound of the present application employs norbornyl as the substituent group, which is easier to control the molecular weight than the compound using adamantyl, so as to avoid excessive evaporation temperatures caused by excessive molecular weight, so that the nitrogen-containing compound can have lower evaporation temperature, so as to achieve better mass production thermal stability.

What is claimed is:

1. A nitrogen-containing compound, having a structural formula represented by formula I:

formula I

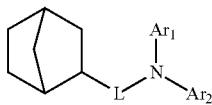

wherein L is a single bond;

wherein Ar₁ and Ar₂ are the same or different and are independently selected from a substituted or unsubstituted aryl having 6-31 carbon atoms, or a substituted or unsubstituted heteroaryl having 2-30 carbon atoms;

wherein substituents of L, Ar₁ and Ar₂ are independently selected from deuterium, nitro, hydroxy, alkyl, cycloalkyl, alkenyl, alkynyl, alkoxy, alkylthio, arylsilyl, aryl optionally substituted with 0, 1, 2, 3, 4, or 5 substituent(s) selected from deuterium, fluorine, cyano and methyl, and heteroaryl optionally substituted with 0, 1, 2, 3, 4, or 5 substituent(s) selected from deuterium, fluorine, cyano or methyl.

2. A nitrogen-containing compound, having a structural formula represented by formula I:

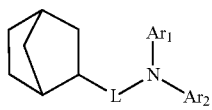

formula I wherein L is selected from a single bond, a substituted or unsubstituted arylene having 6-30 carbon atoms, or a substituted or unsubstituted heteroarylene having 1-30 carbon atoms;

wherein Ar₁ and Ar₂ are the same or different and are independently selected from a substituted or unsubstituted aryl having 6-31 carbon atoms, or a substituted or unsubstituted heteroaryl having 2-30 carbon atoms;

wherein substituents of L, Ar₁ and Ar₂ are independently selected from deuterium, nitro, hydroxy, alkyl, cycloalkyl, alkenyl, alkynyl, alkoxy, alkylthio, arylsilyl, aryl optionally substituted with 0, 1, 2, 3, 4, or 5 substituent(s) selected from deuterium, fluorine, cyano and methyl, and heteroaryl optionally substituted with 0, 1, 2, 3, 4, or 5 substituent(s) selected from deuterium, fluorine, cyano or methyl; and wherein the nitrogen-containing compound is selected from the group consisting of the following compounds:

1

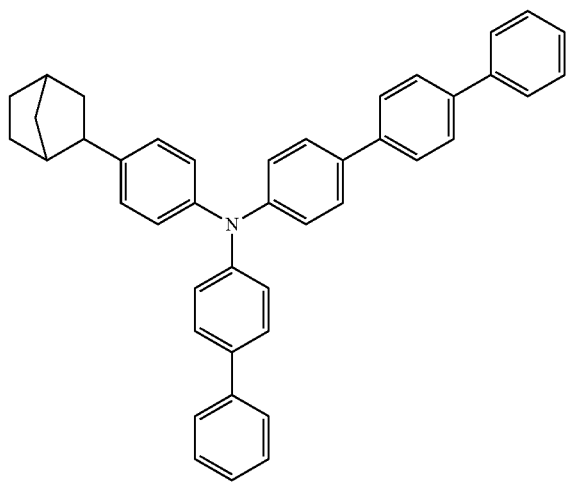

2

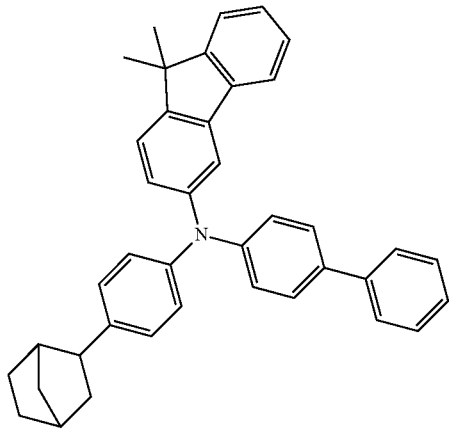

3

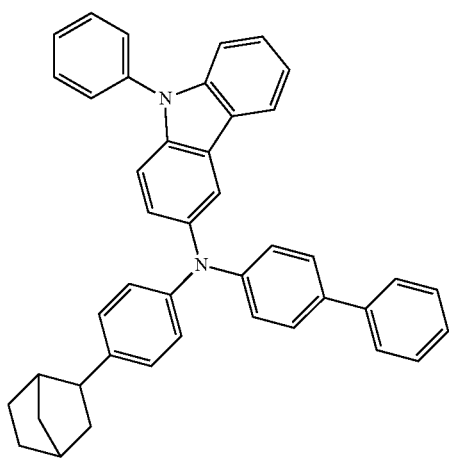

4

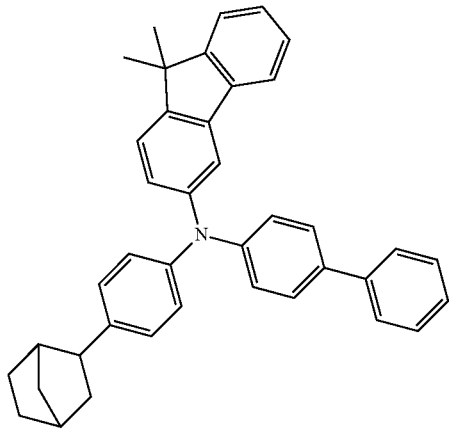

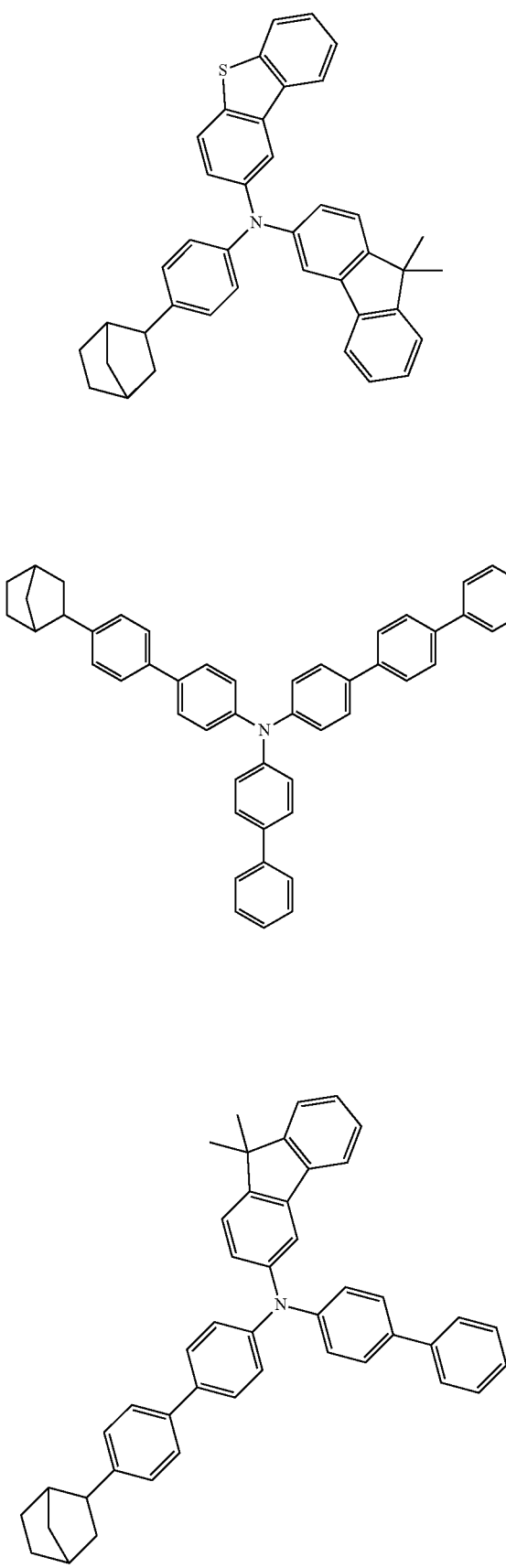
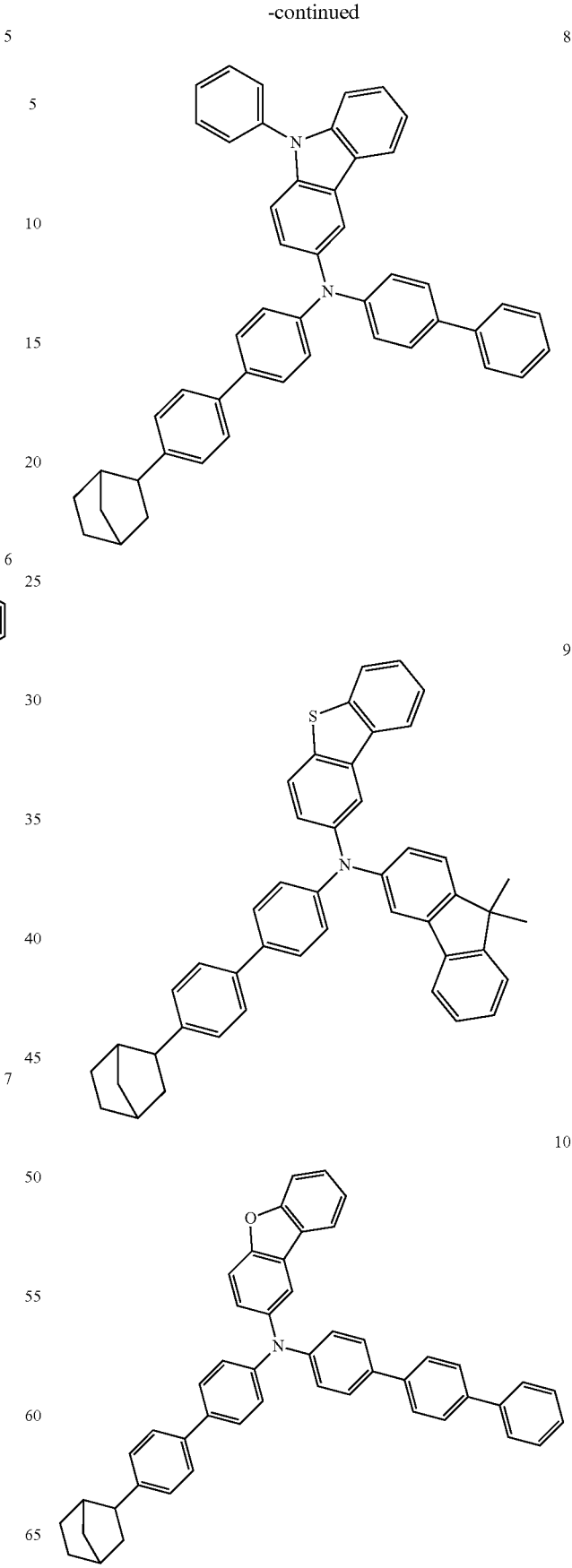

11
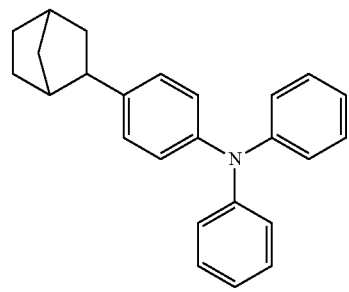
12
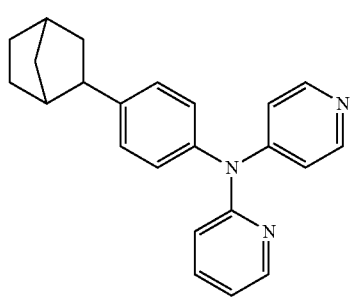
13
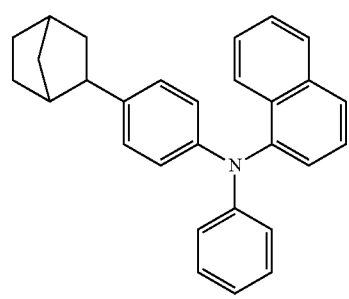
14
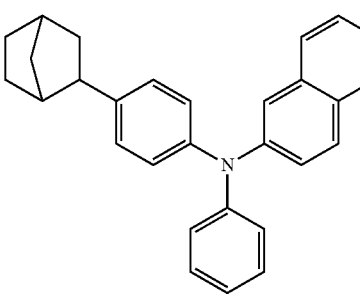
15
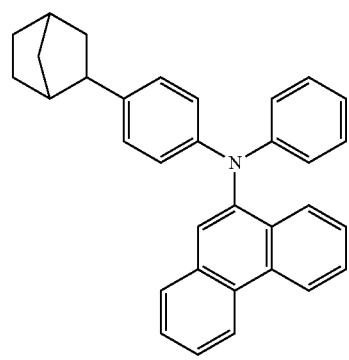
16
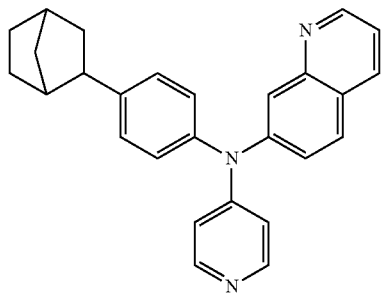
17
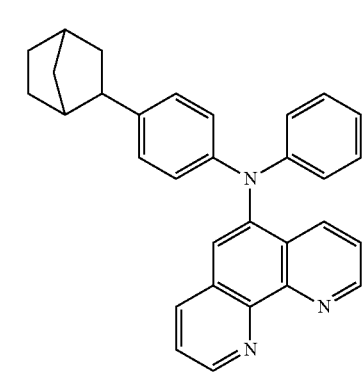
18
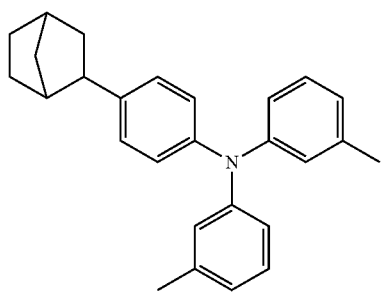
19
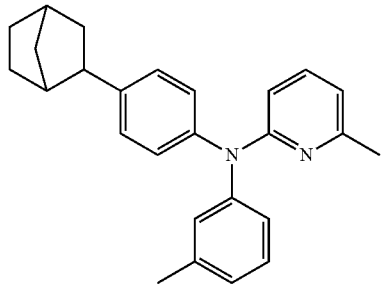
20
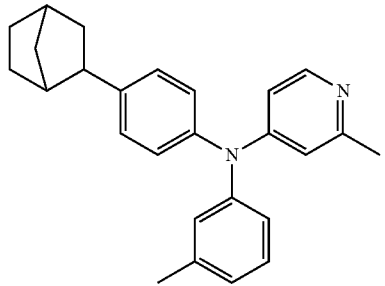

101
-continued
21
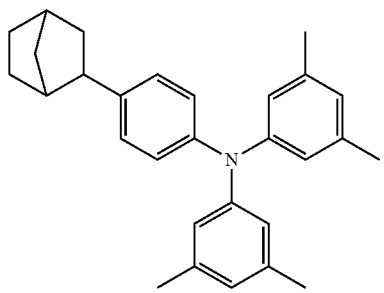
22
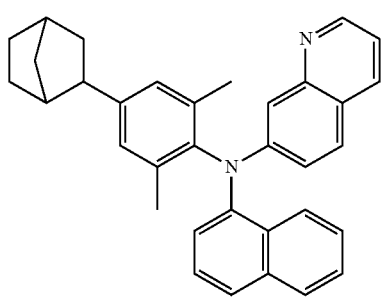
23
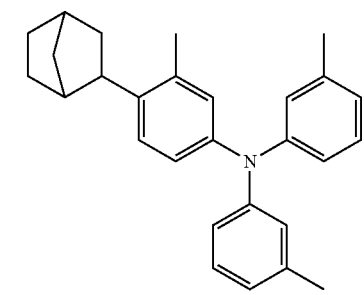
24
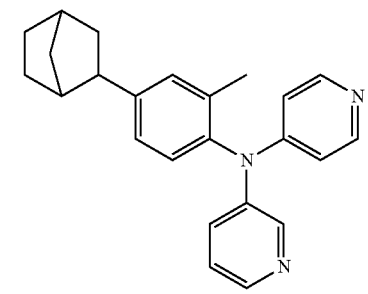
25
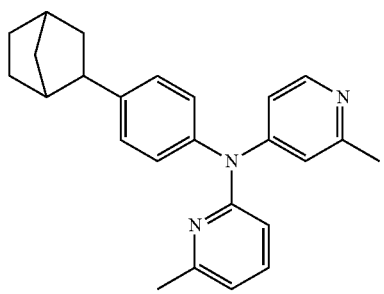
102
-continued
26
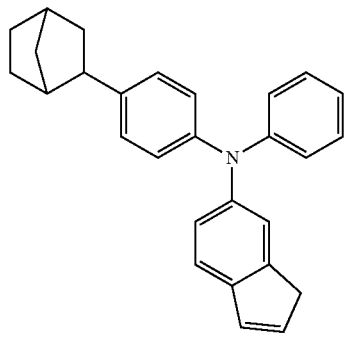
27
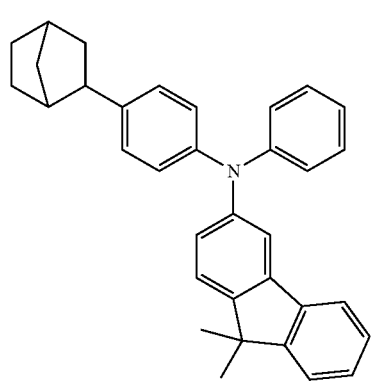
28
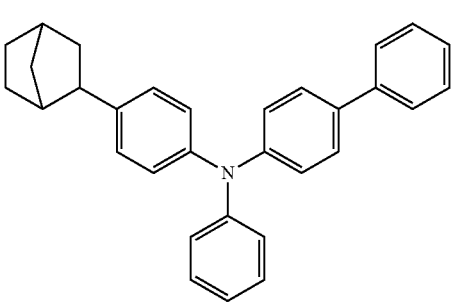
29
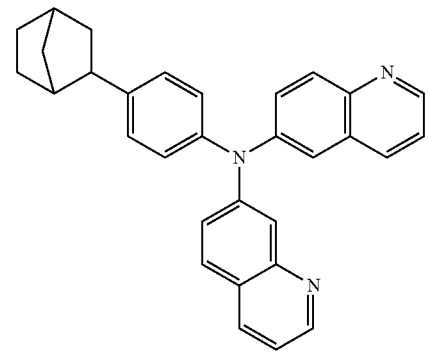

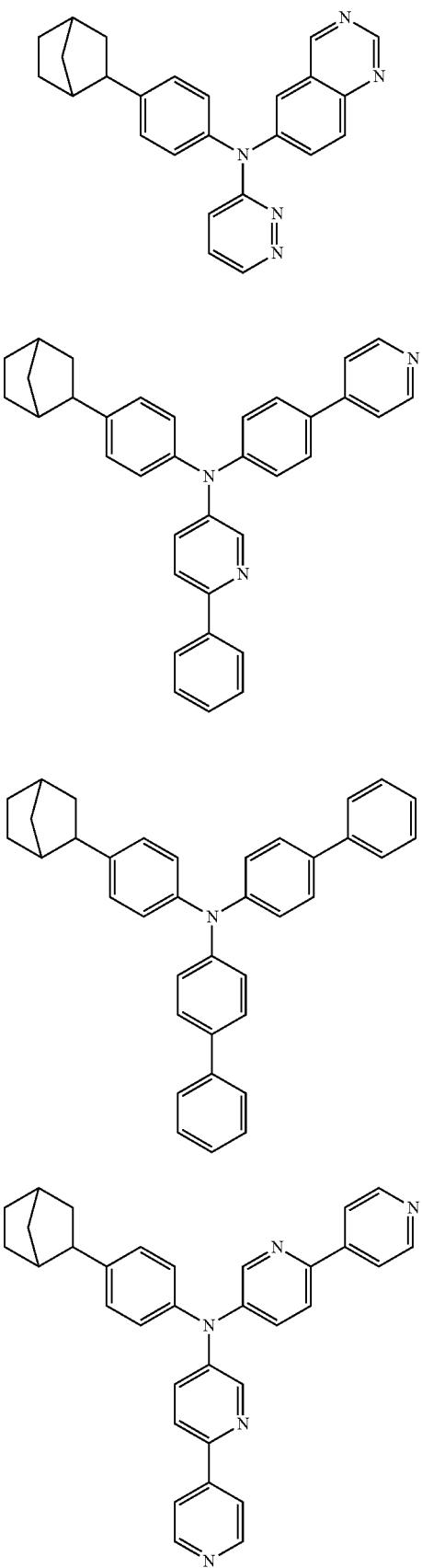
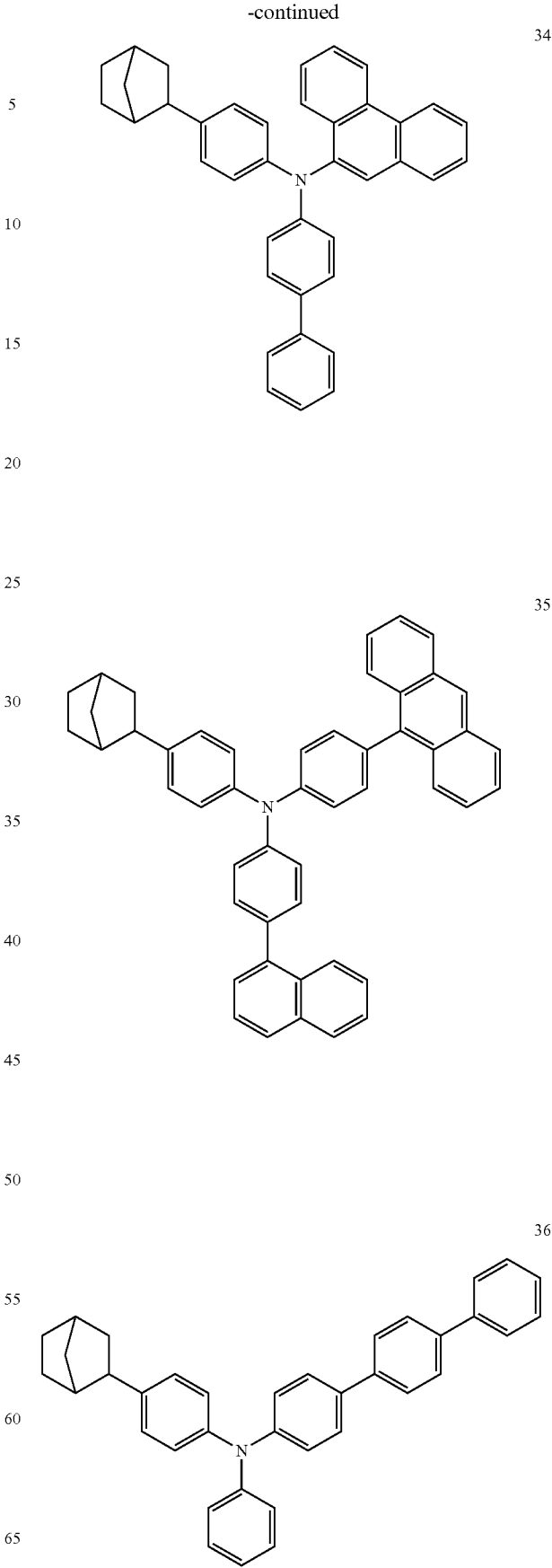

37
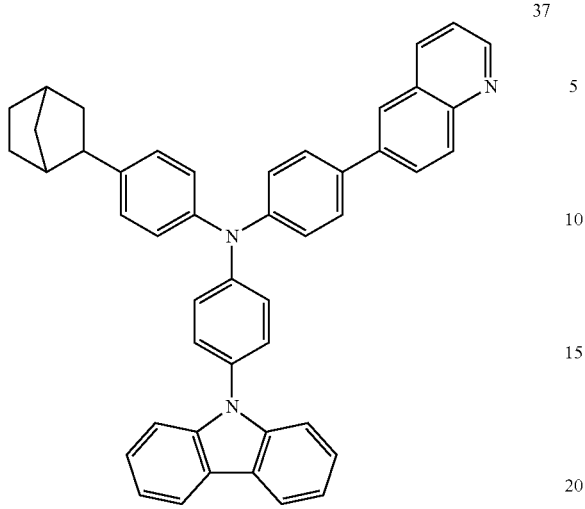
38
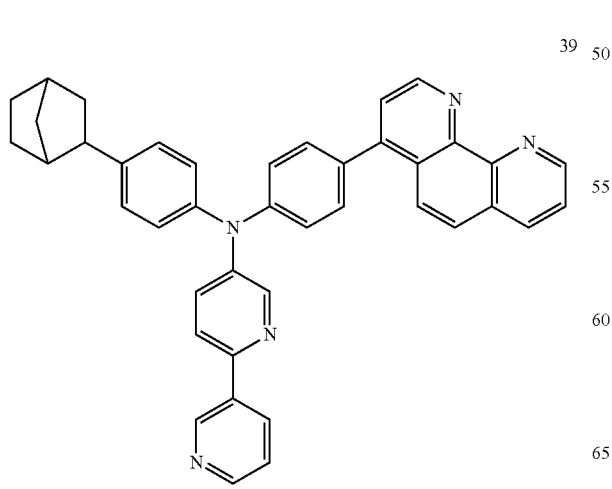
39
40
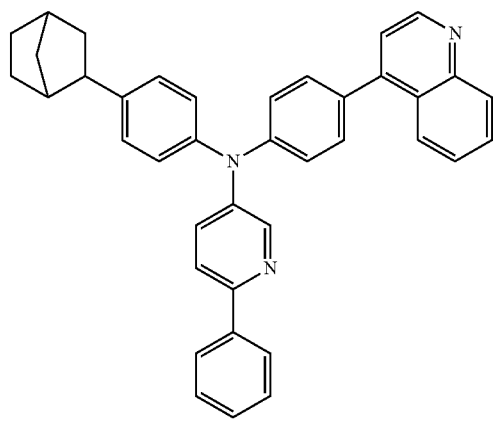
41
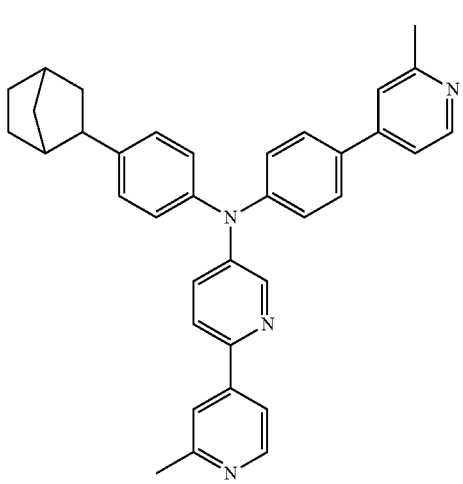
42
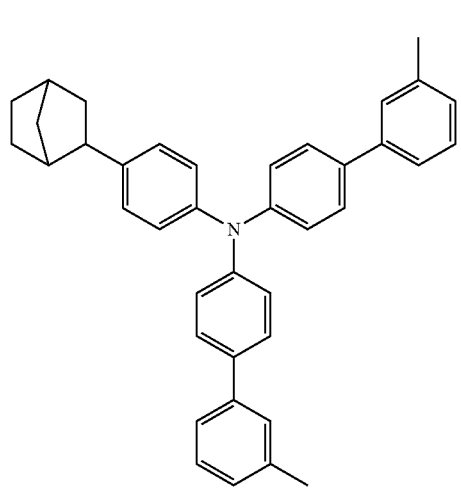

43
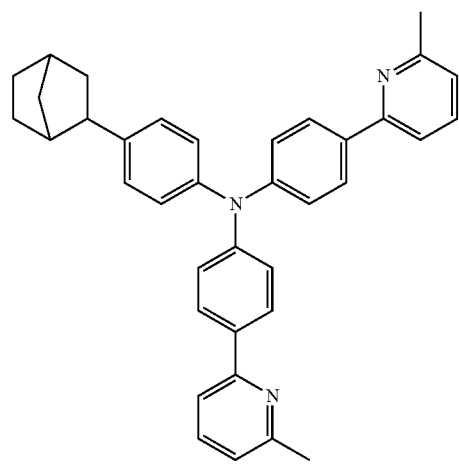
44
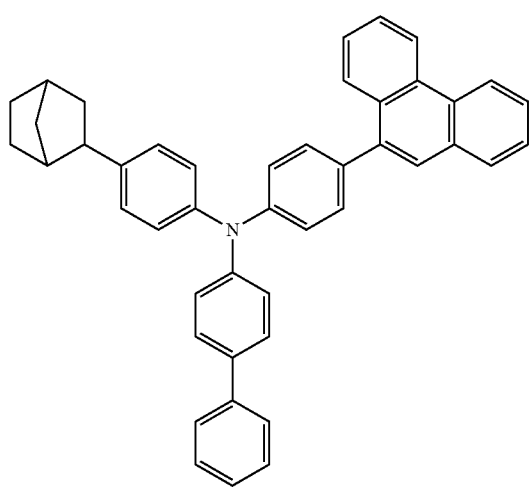
45
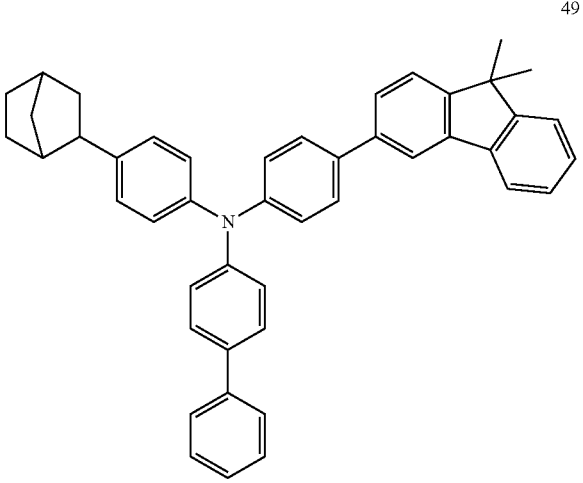
46
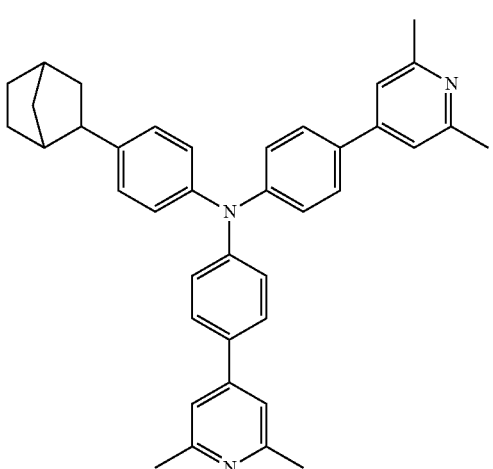
47
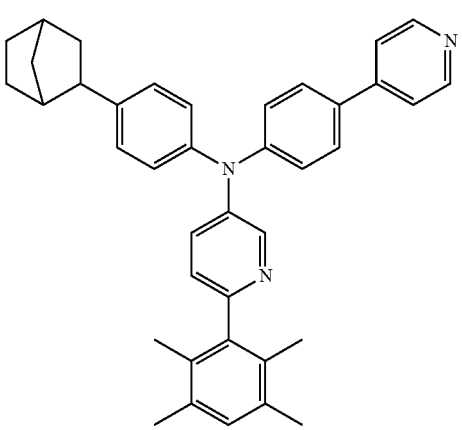
48
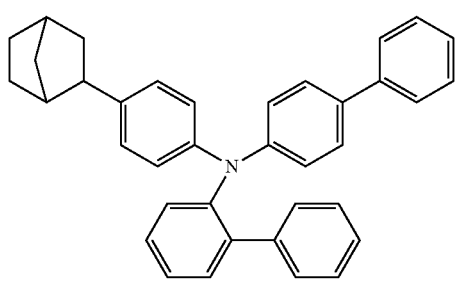
49

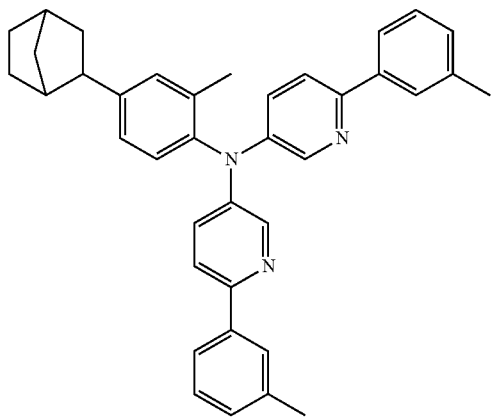
50
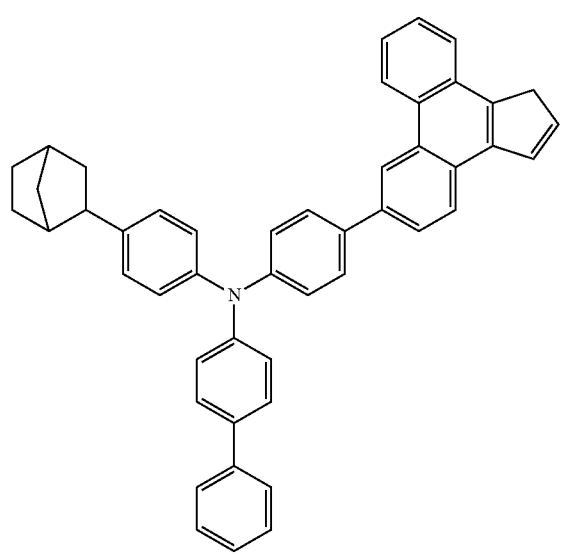
51
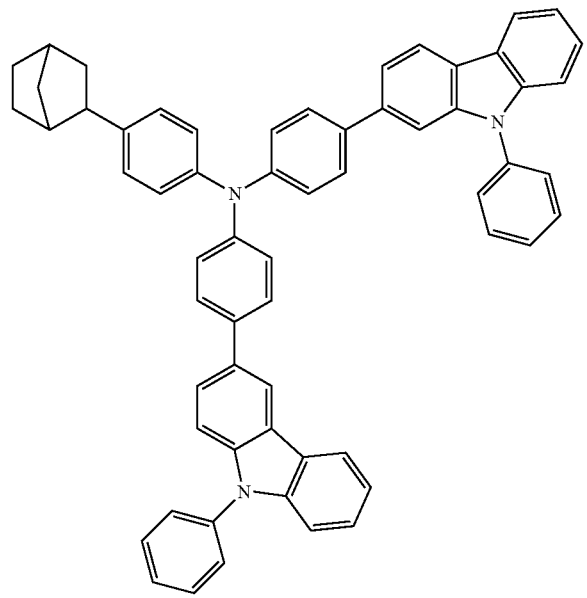
52
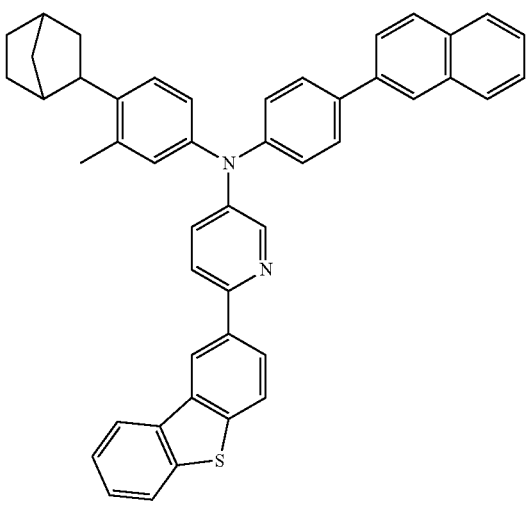
53
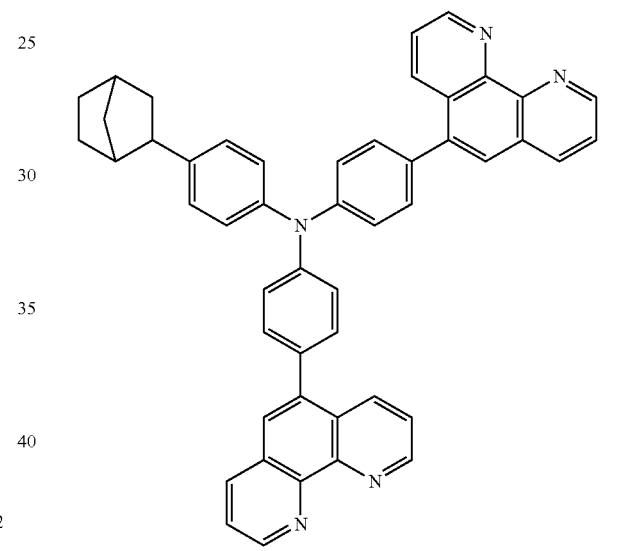
54
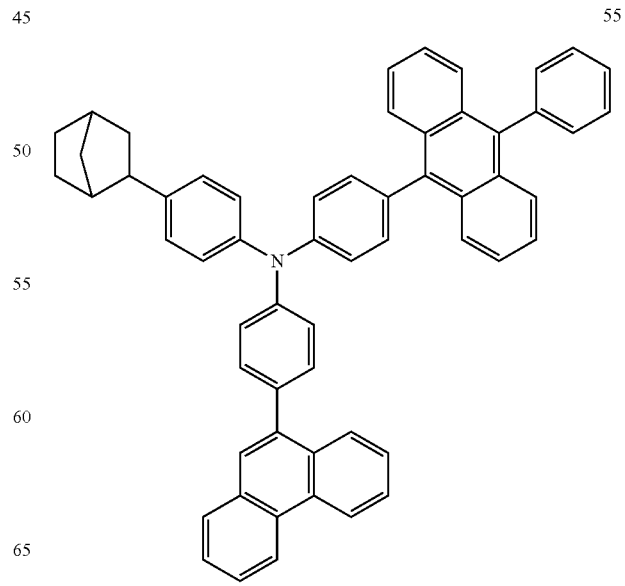
55

56
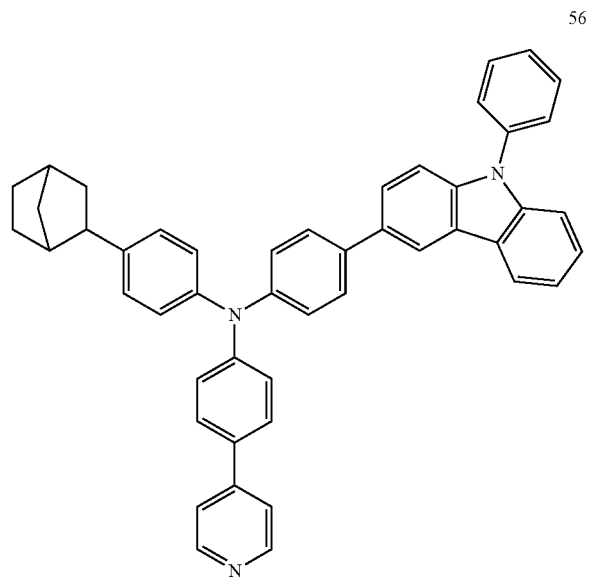
57
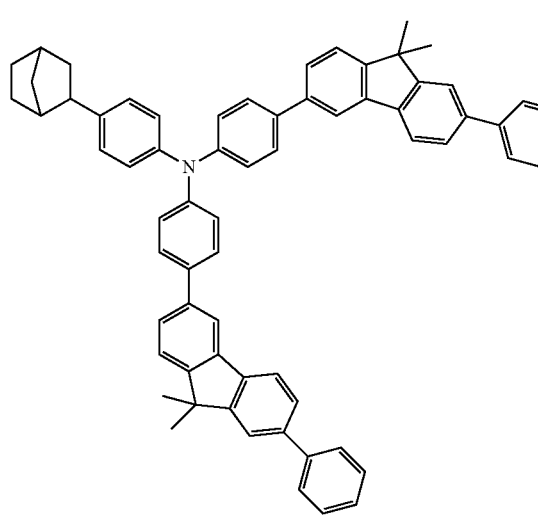
58
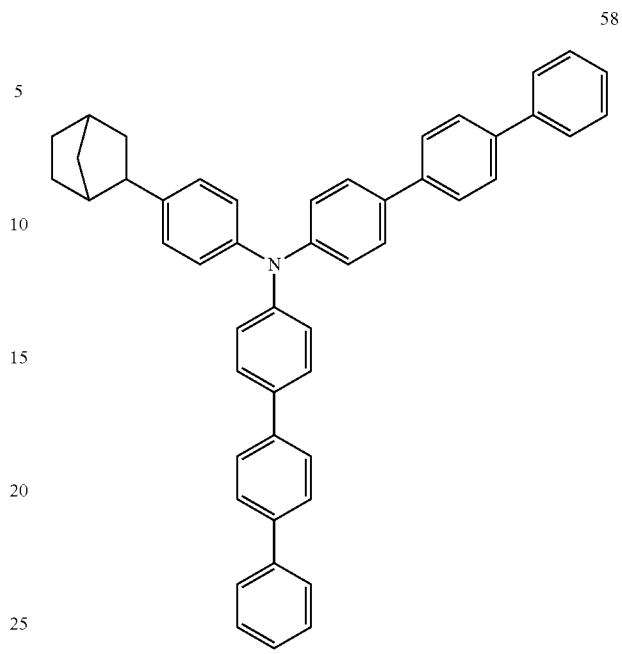
59
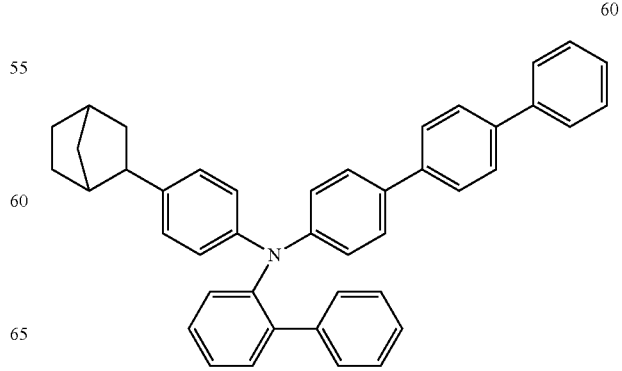
60

61
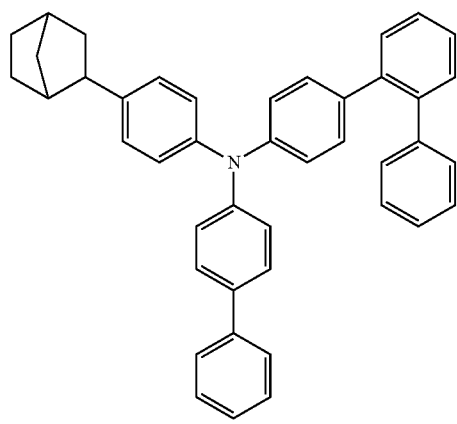
62
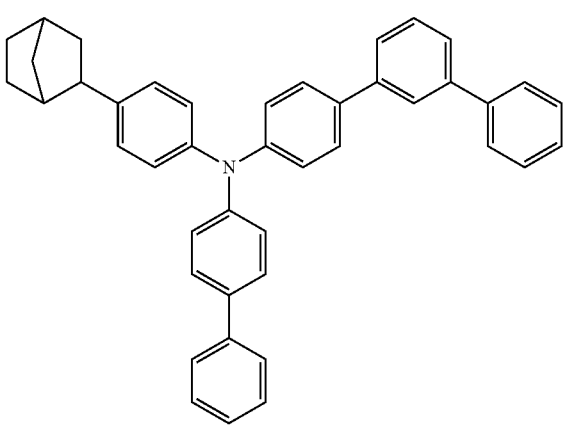
63
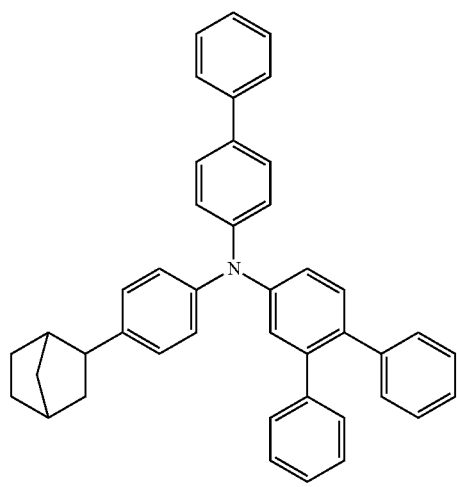
64
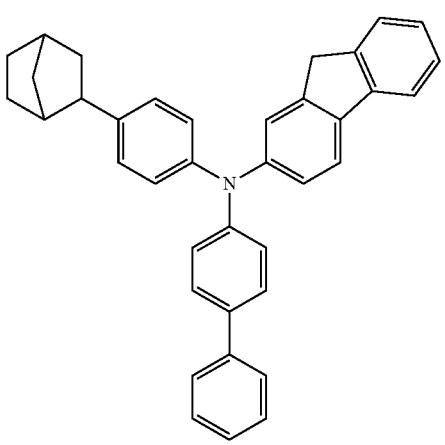
65
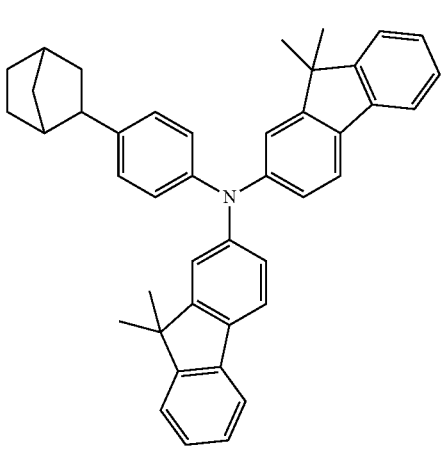
66
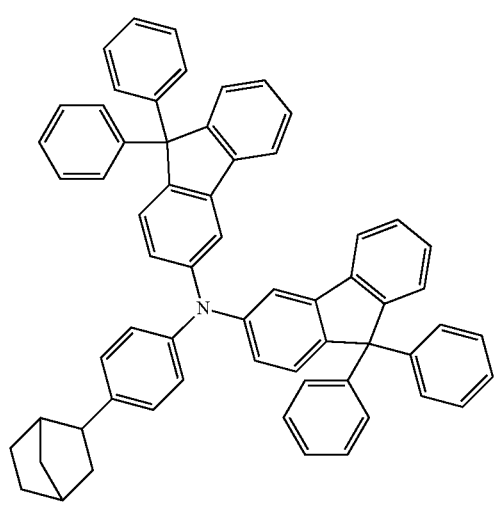

67
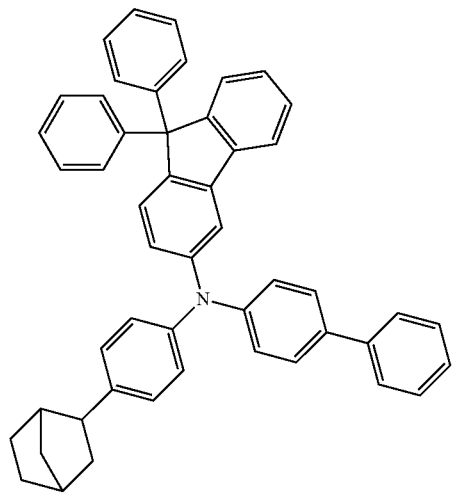
68
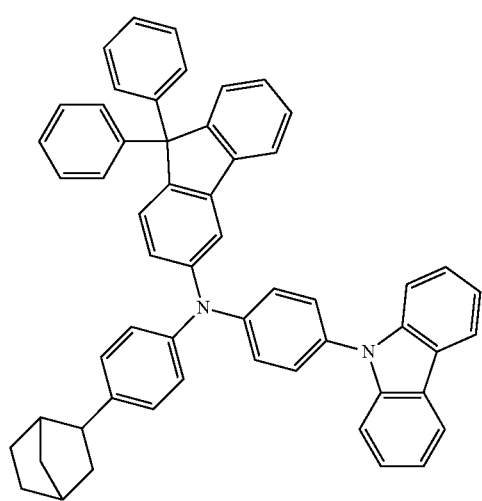
69
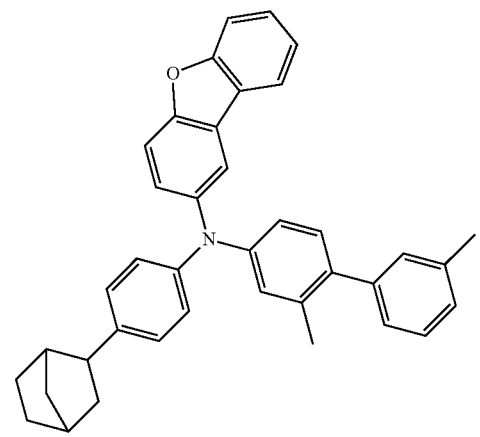
70
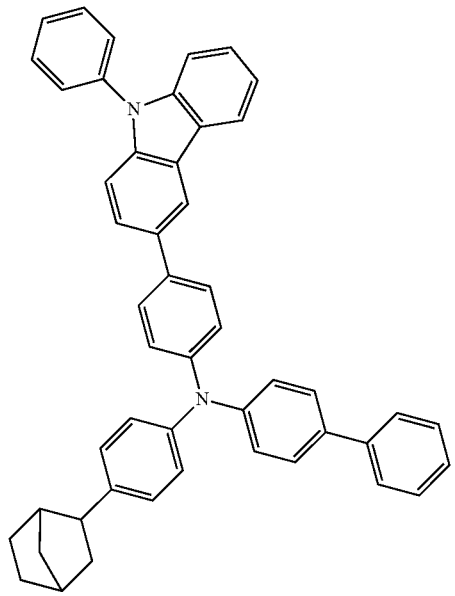
71
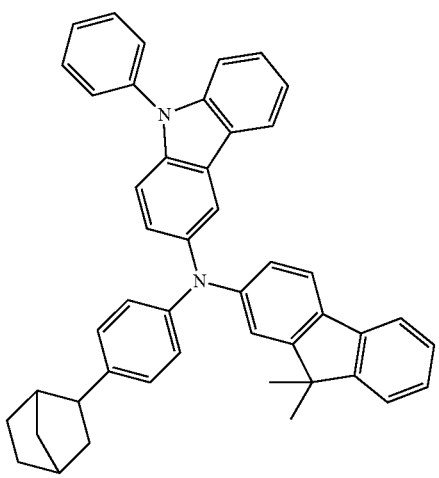

73
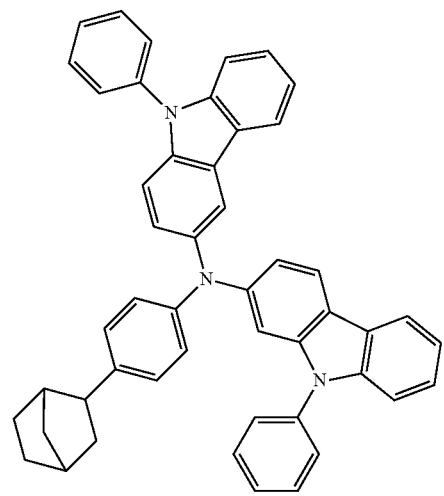
74
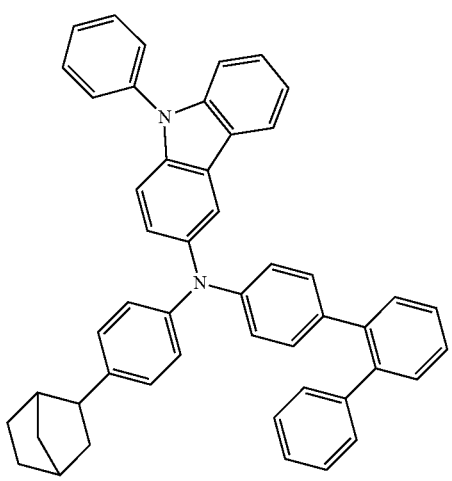
75
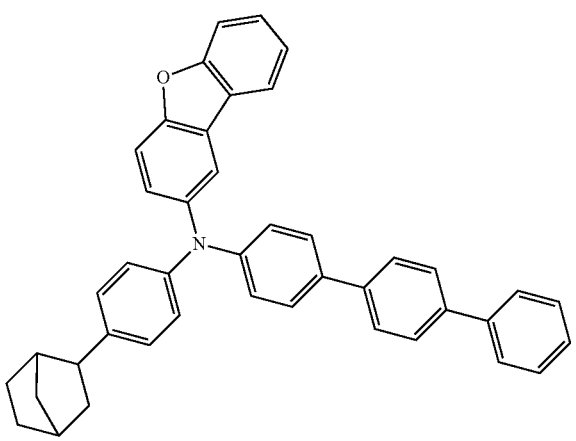
76
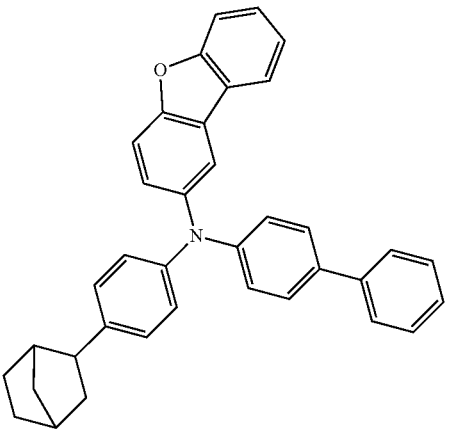
77
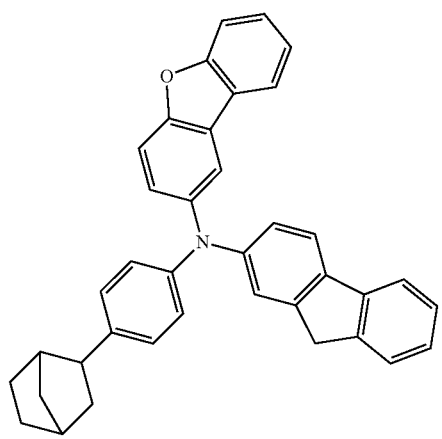
78
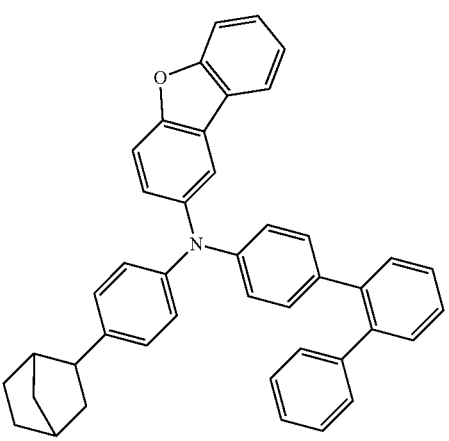
79
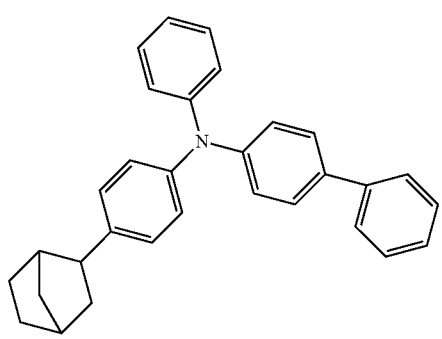

80
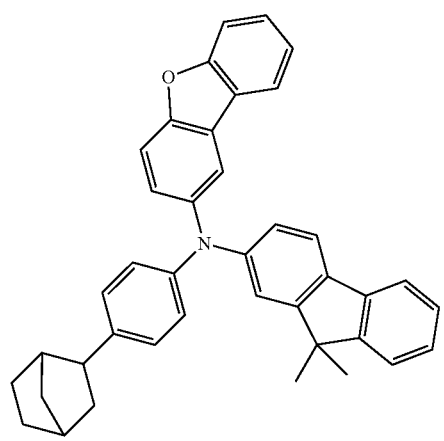
81
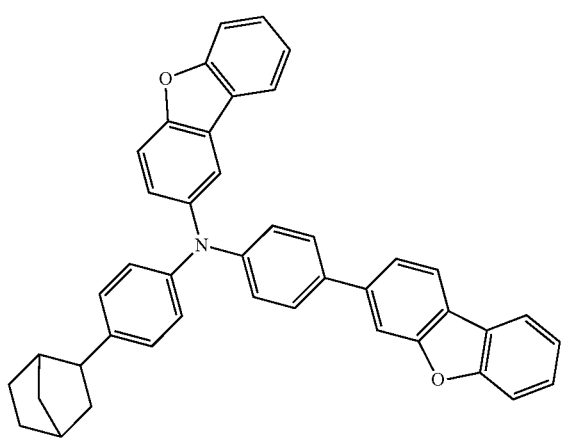
82
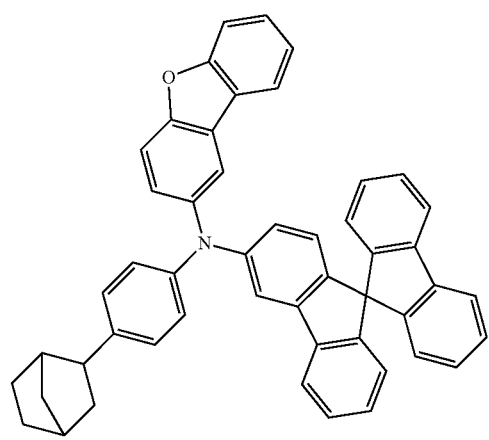
83
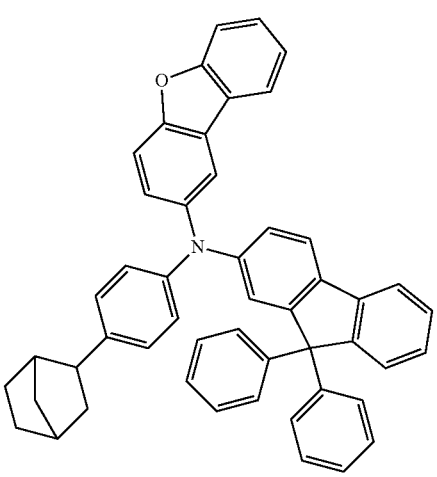
84
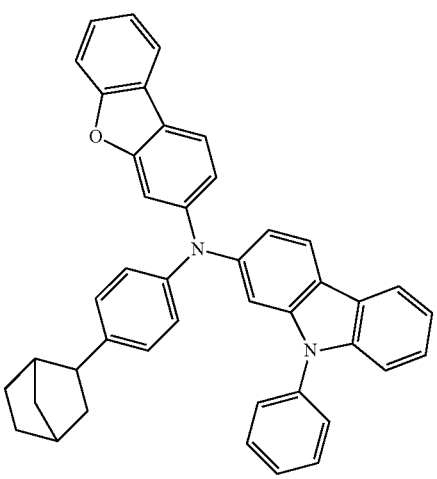
85
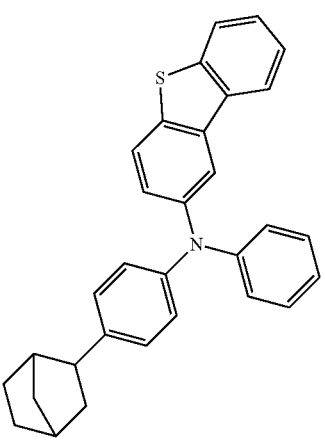

86
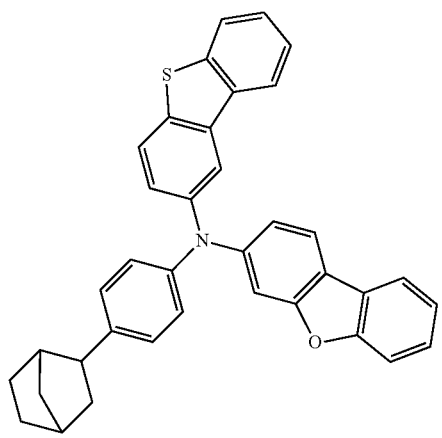
87
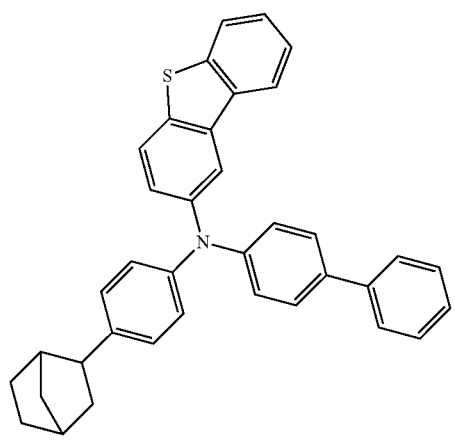
88
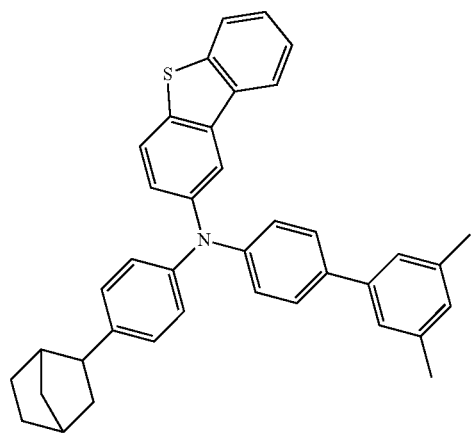
89
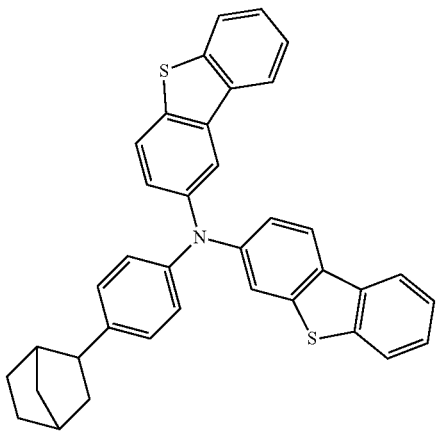
90
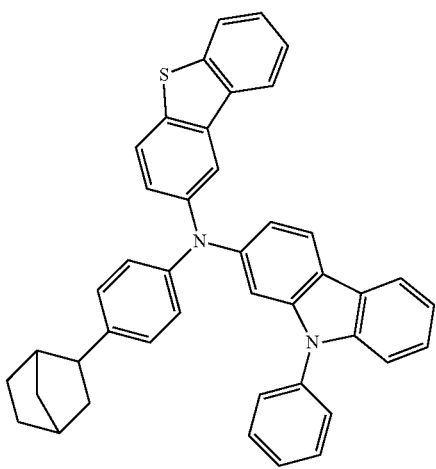
92
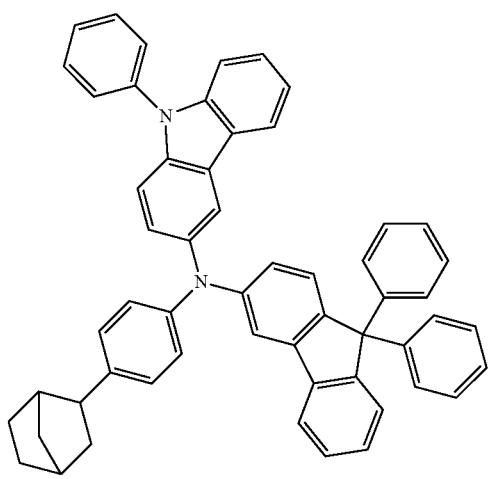

-continued
93
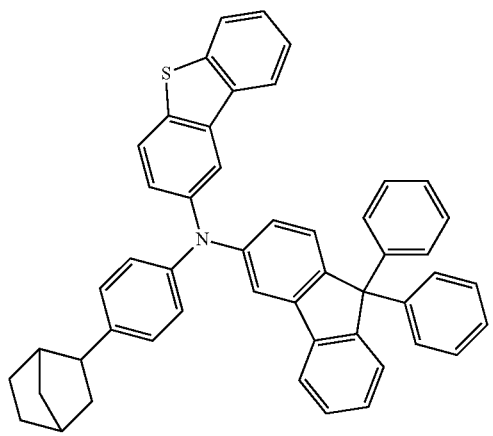
144
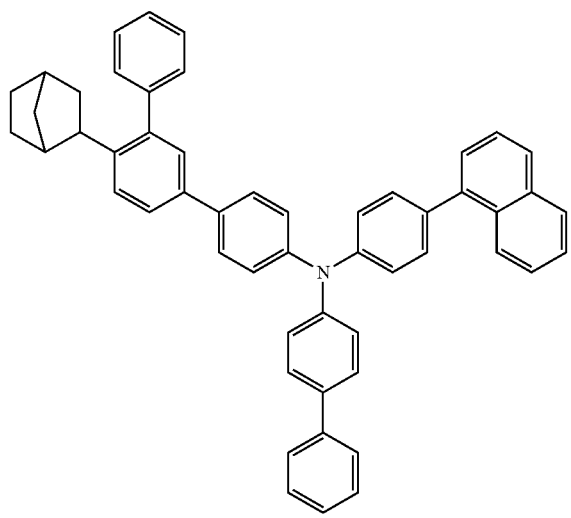
94
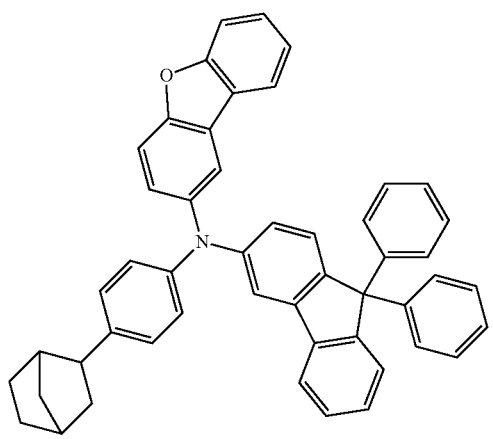
-continued
95
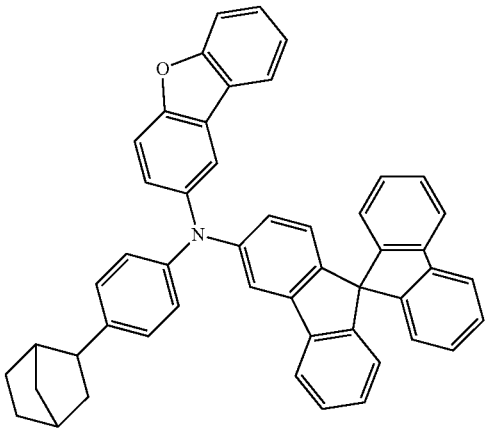
96
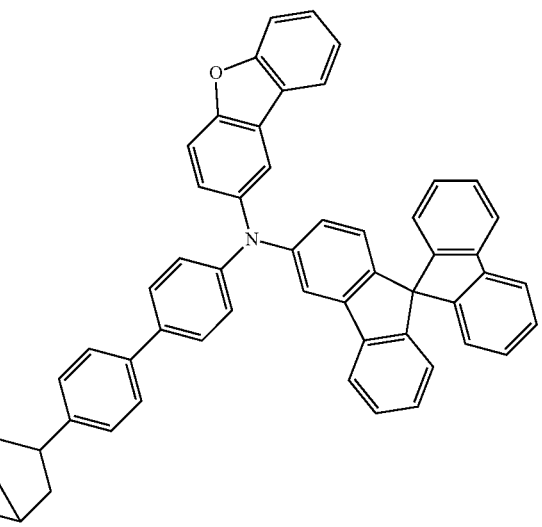
97

98
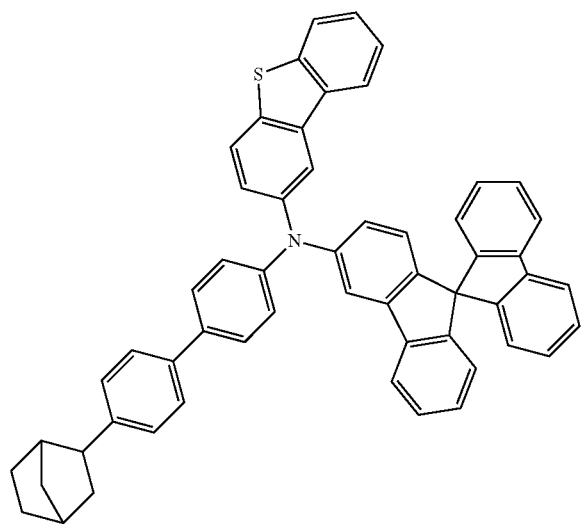
99
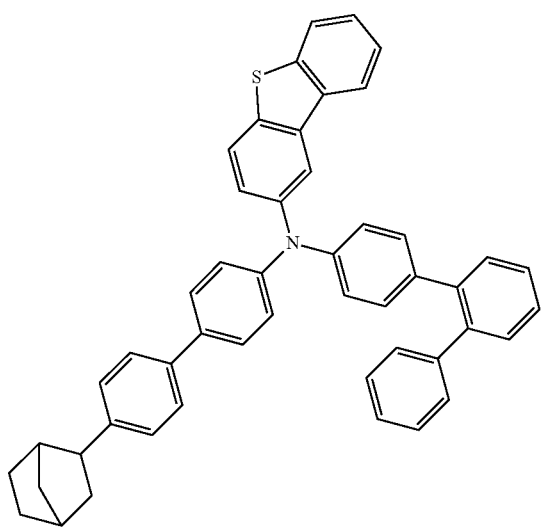
100
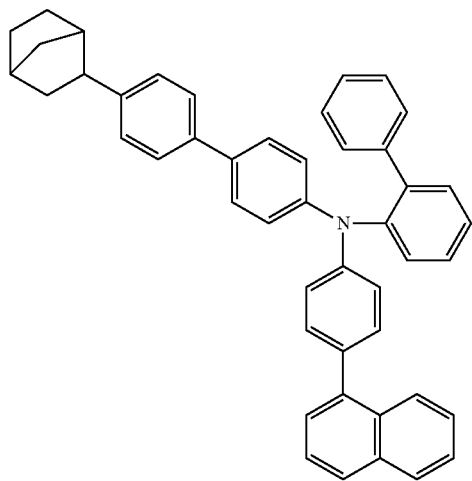
101
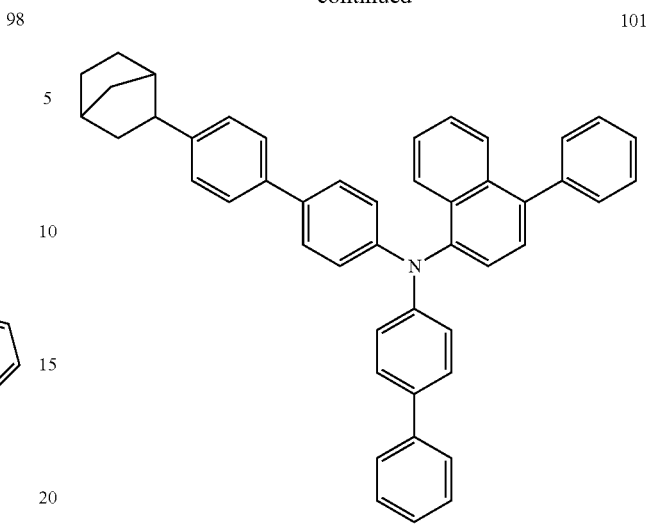
102
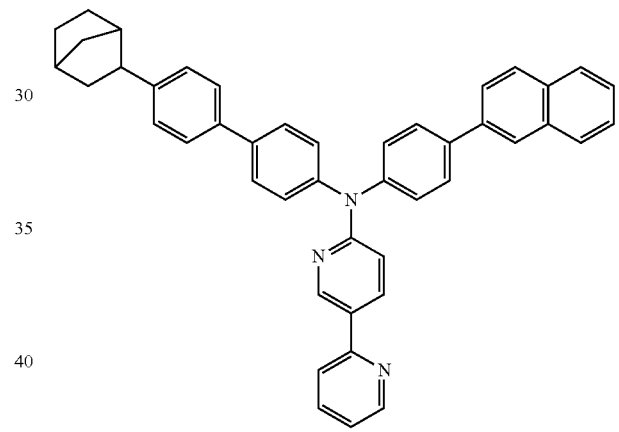
103
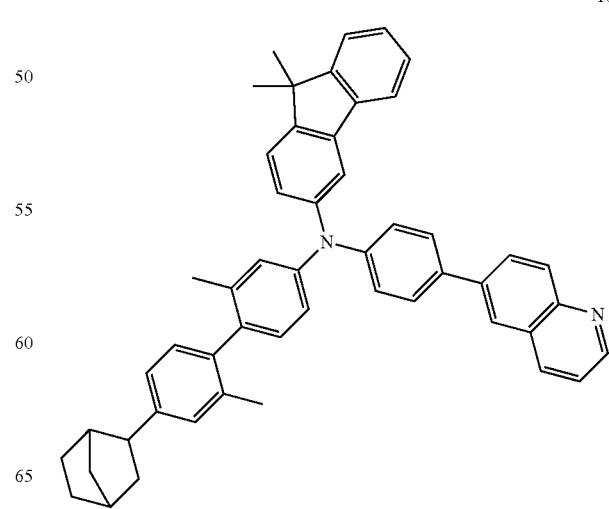

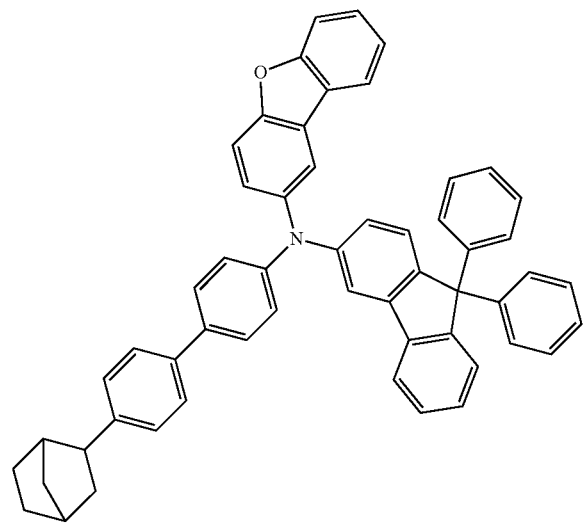
104
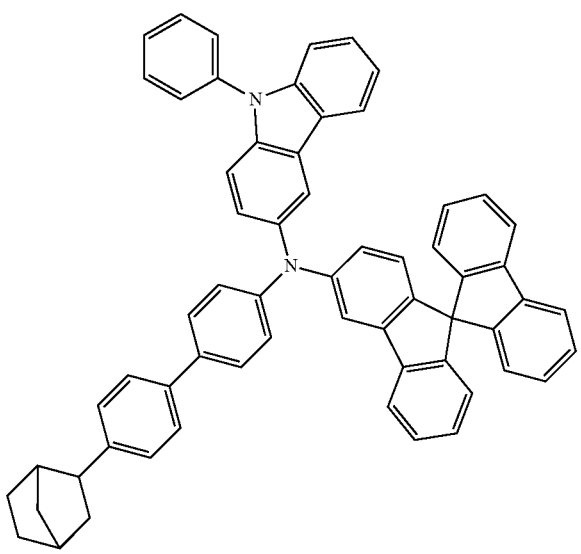
106
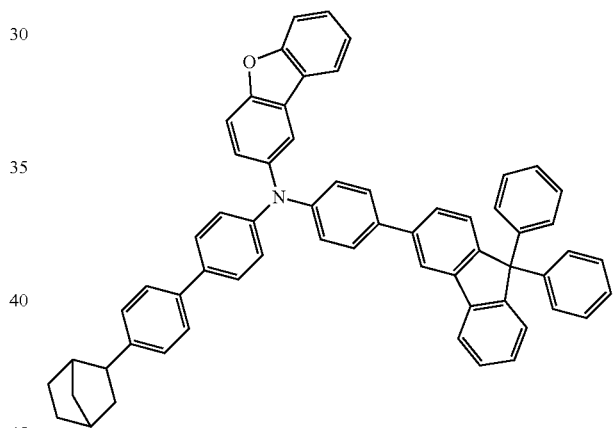
107
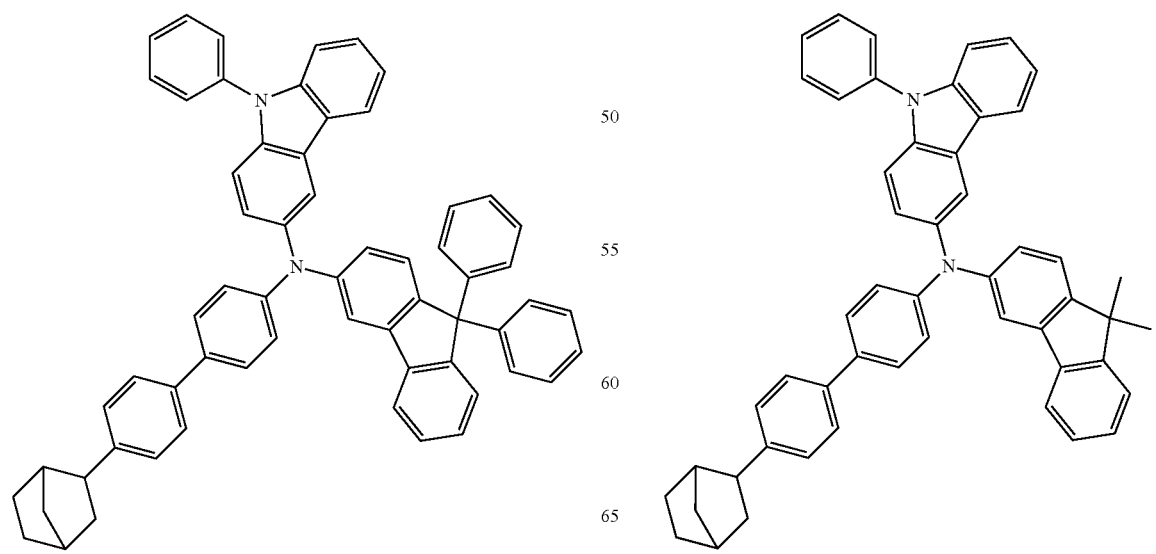
105
108

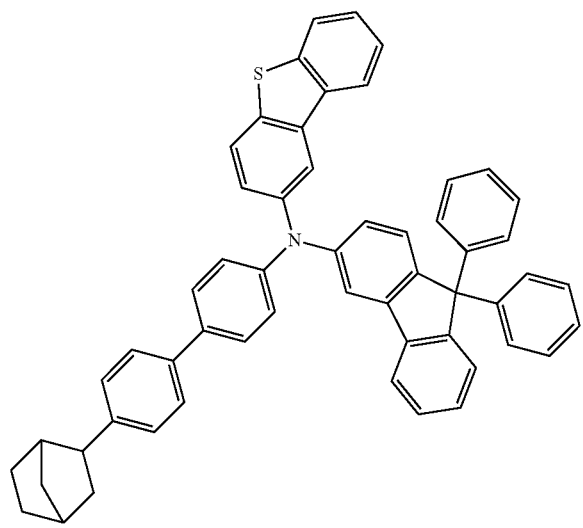
109
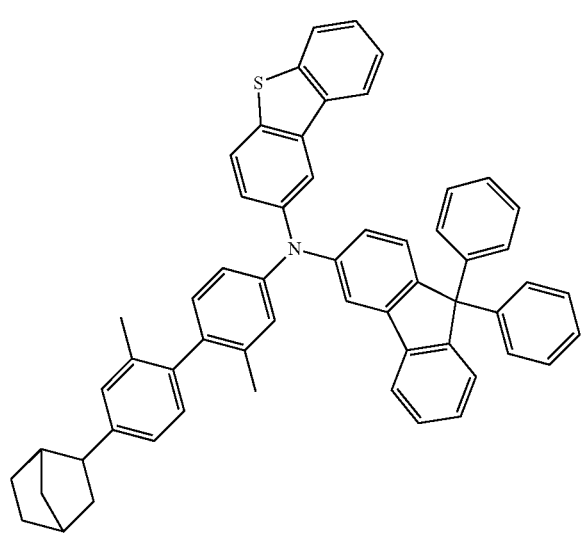
110
111
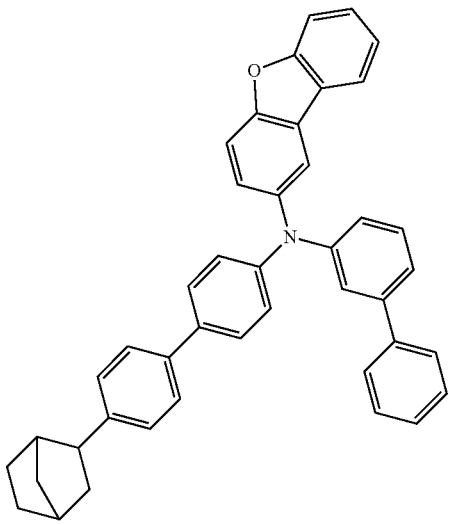
112
113
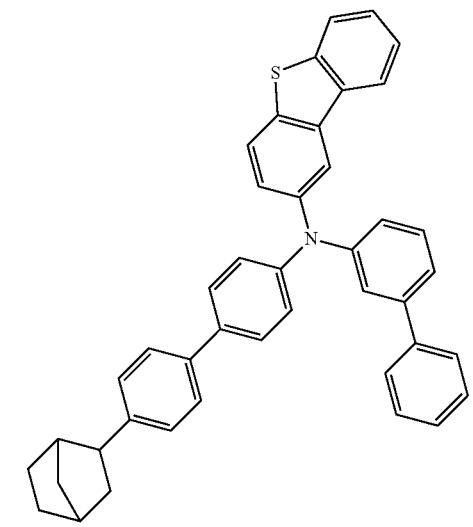
114

131
-continued
115
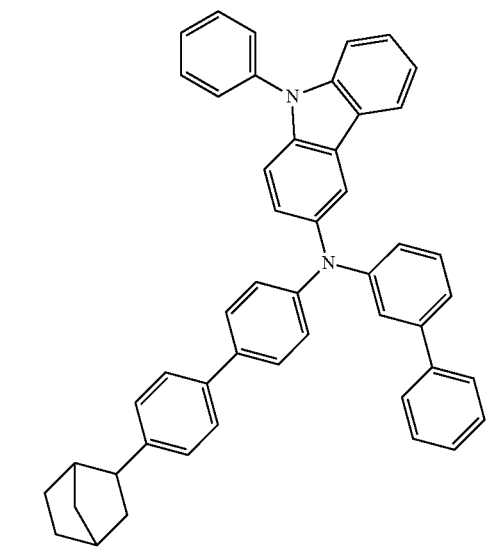
116
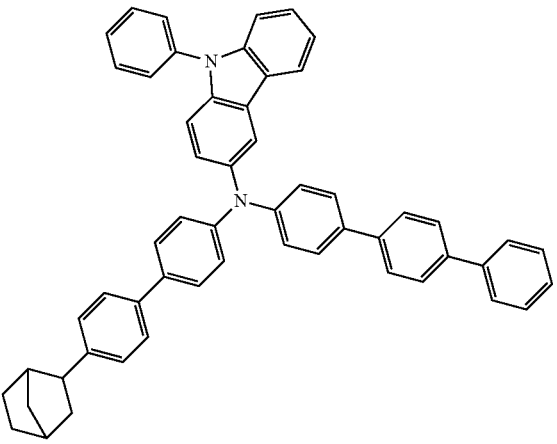
117
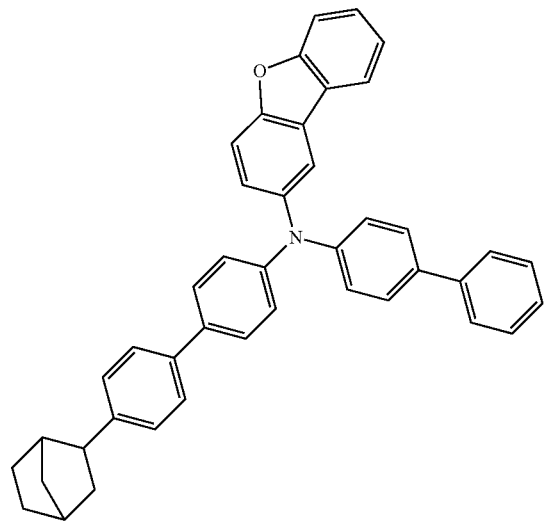
132
-continued
118
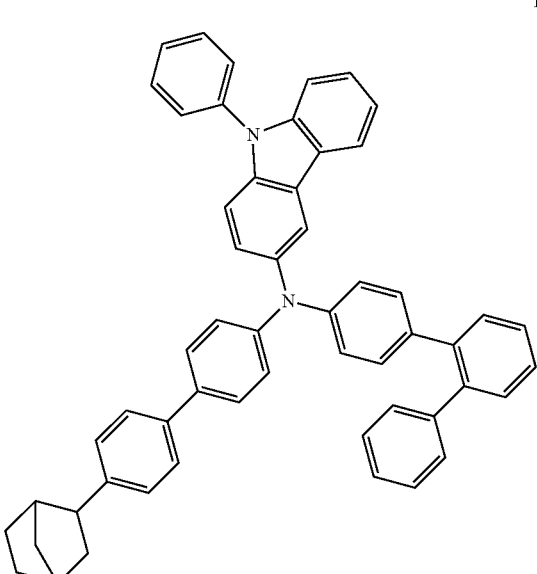
119
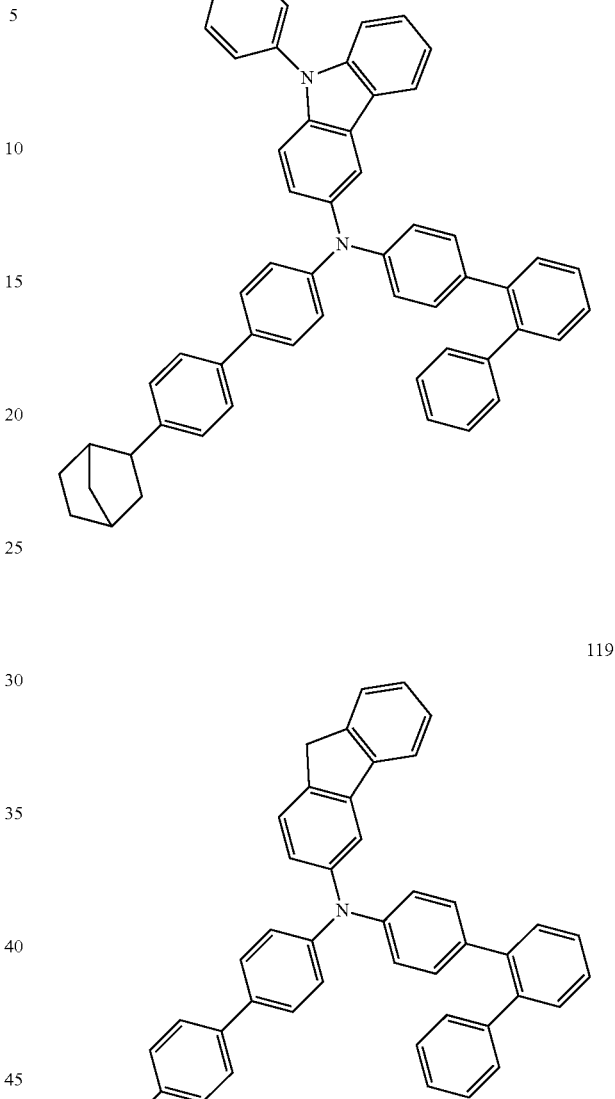
120
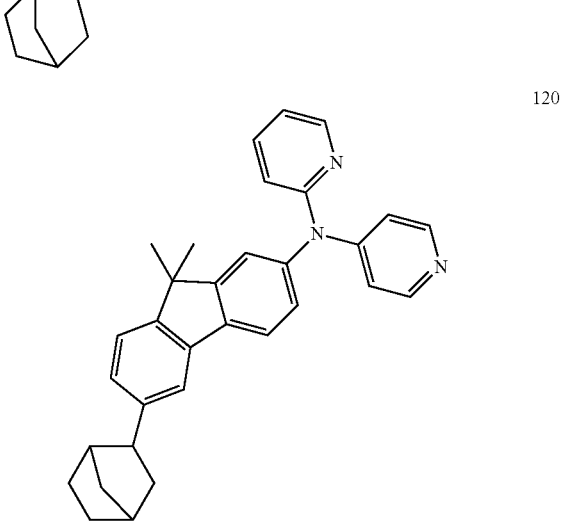

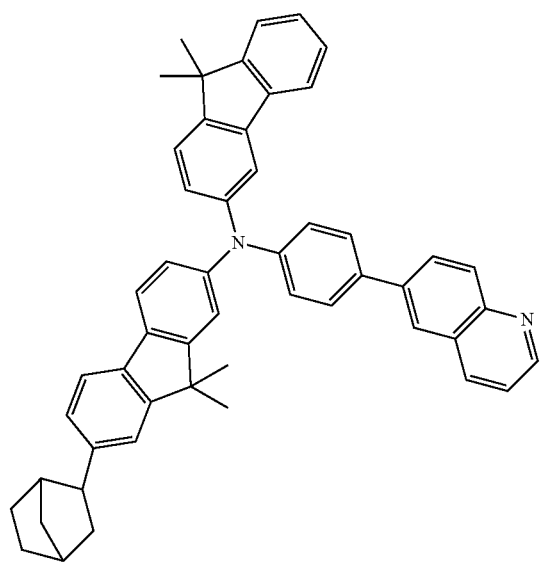

135
-continued
127
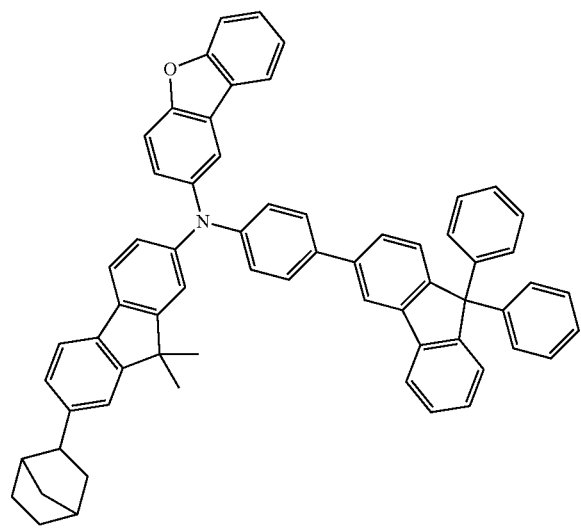
128
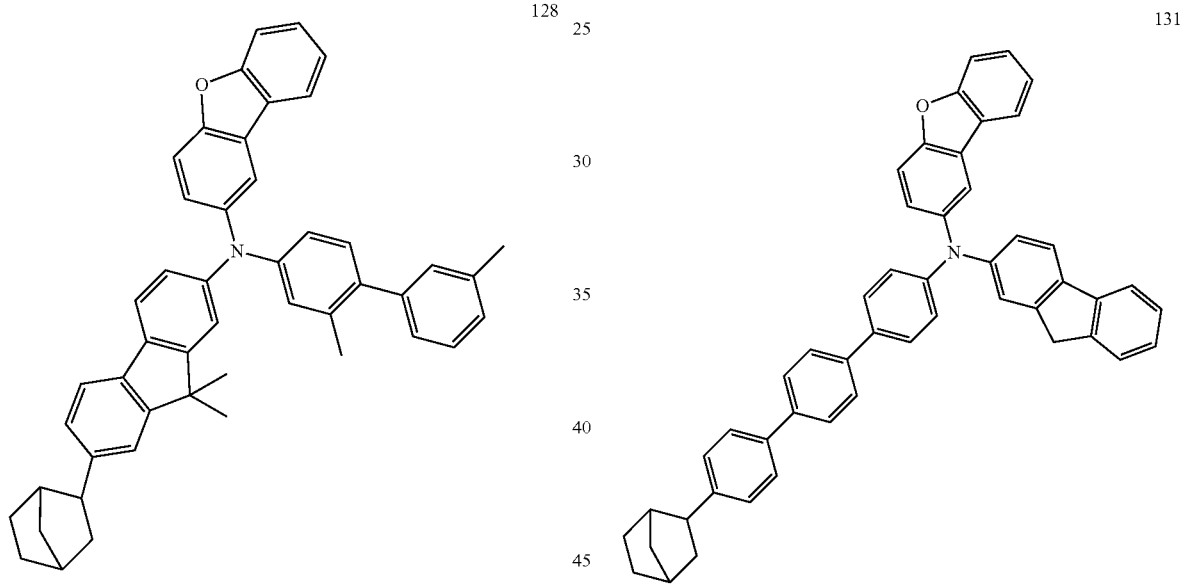
129
130
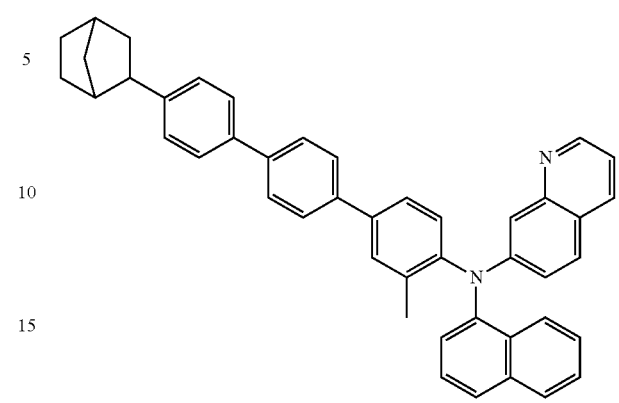
136
-continued
131
132
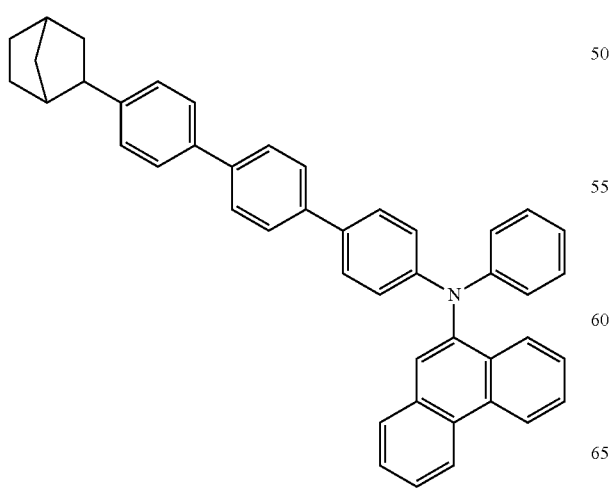

133
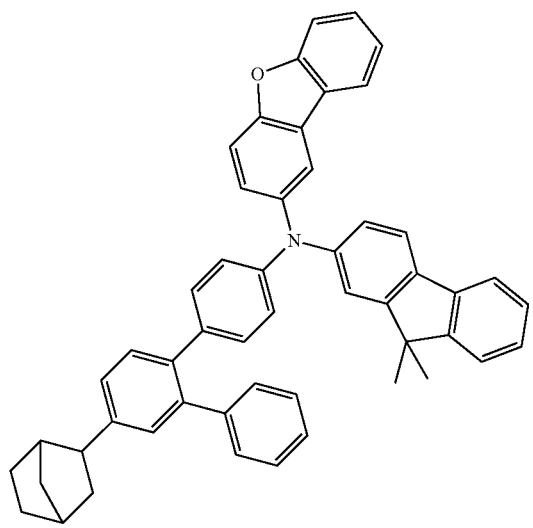
134
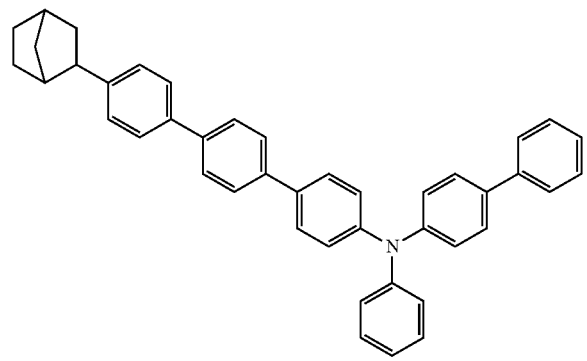
135
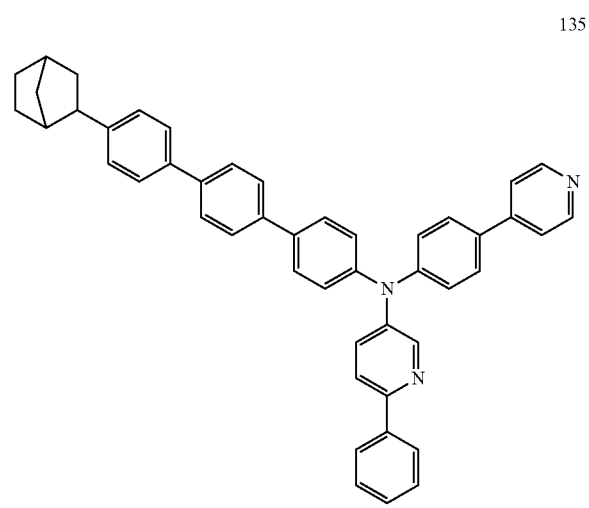
136
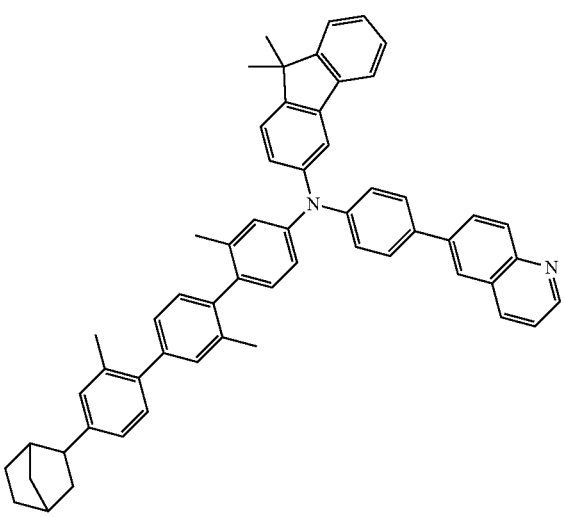
137
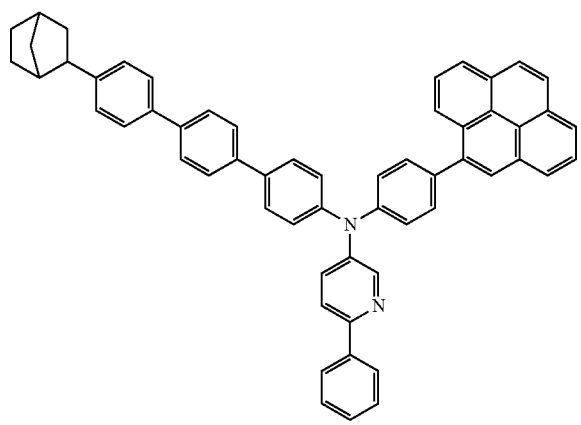
138
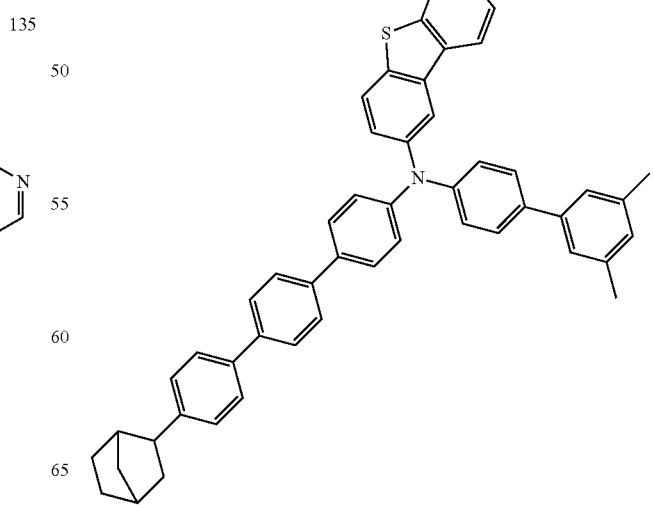

139
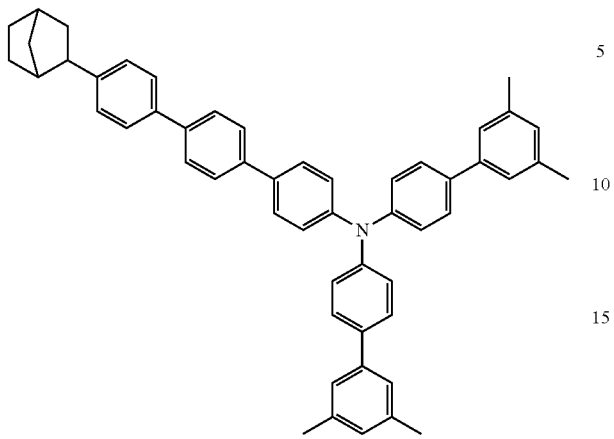
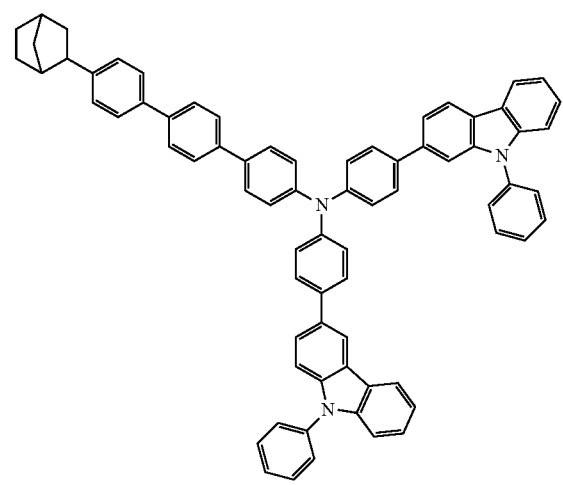
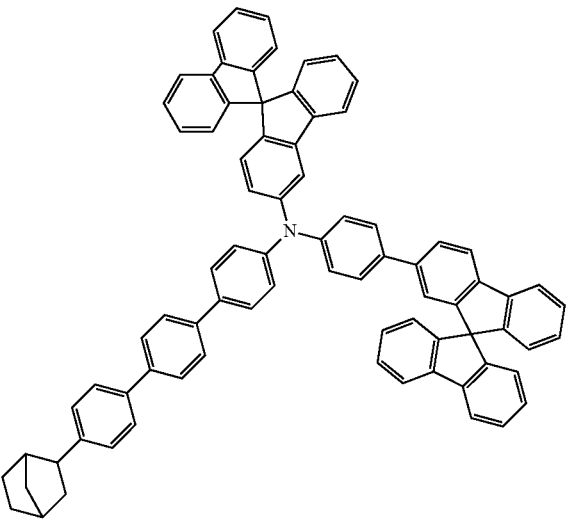
140
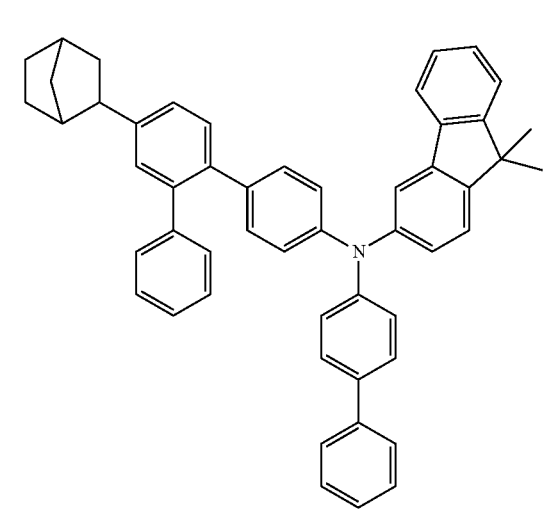
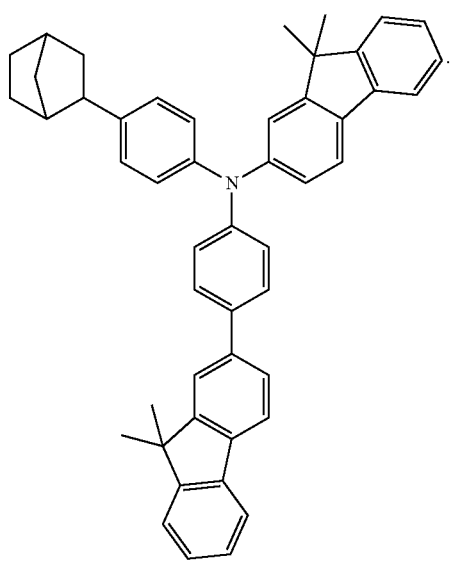

3. An electronic element, comprising:
an anode and a cathode which are oppositely disposed; and
a functional layer disposed between the anode and the cathode,
wherein the functional layer contains the nitrogen-containing compound according to claim 2.

4. The electronic element according to claim 3, wherein the functional layer comprises an electron blocking layer comprising the nitrogen-containing compound.

5. The electronic element according to claim 3, wherein the functional layer comprises a hole transport layer comprising the nitrogen-containing compound.

6. The electronic element according to claim 3, wherein the electronic element is an organic electroluminescent device or a solar cell.

7. An electronic device, comprising:
the electronic element according to claim 3.

8. An electronic element, comprising:
an anode and a cathode which are oppositely disposed; and
a functional layer disposed between the anode and the cathode,
wherein the functional layer contains the nitrogen-containing compound according to claim 1.

9. The electronic element according to claim 8, wherein the functional layer comprises an electron blocking layer comprising the nitrogen-containing compound.

10. The electronic element according to claim 8, wherein the functional layer comprises a hole transport layer comprising the nitrogen-containing compound.

11. The electronic element according to claim 8, wherein the electronic element is an organic electroluminescent device or a solar cell.

12. An electronic device, comprising:
the electronic element according to claim 8.

* * * * *